United States Patent
Tagawa et al.

(10) Patent No.: US 11,325,120 B2
(45) Date of Patent: May 10, 2022

(54) SPECIMEN TREATMENT CHIP, SPECIMEN TREATMENT APPARATUS, AND SPECIMEN TREATMENT METHOD

(71) Applicant: SYSMEX CORPORATION, Kobe (JP)

(72) Inventors: Ayato Tagawa, Kobe (JP); Tsuyoshi Nakano, Kobe (JP); Yasuko Kawamoto, Kobe (JP); Koya Yamawaki, Kobe (JP); Hiroaki Tobimatsu, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 182 days.

(21) Appl. No.: 15/947,006

(22) Filed: Apr. 6, 2018

(65) Prior Publication Data

US 2018/0221878 A1    Aug. 9, 2018

Related U.S. Application Data

(63) Continuation of application No. PCT/JP2016/080008, filed on Oct. 7, 2016.

(30) Foreign Application Priority Data

Oct. 9, 2015 (JP) .............................. JP2015-200767

(51) Int. Cl.
*B01L 3/00* (2006.01)
*B01L 9/00* (2006.01)
(Continued)

(52) U.S. Cl.
CPC ... *B01L 3/502715* (2013.01); *B01L 3/502784* (2013.01); *B01L 9/527* (2013.01);
(Continued)

(58) Field of Classification Search
CPC ............ B01L 3/00; B01L 9/00; C12Q 1/6851
(Continued)

(56) References Cited

U.S. PATENT DOCUMENTS 3,698,432 A * 10/1972 Kutz .................. F15B 13/0896
137/884
5,640,995 A * 6/1997 Packard .................... F15C 5/00
137/597
(Continued)

FOREIGN PATENT DOCUMENTS

CN      1502068 A    6/2004
CN    102036750 A    4/2011
(Continued)

OTHER PUBLICATIONS

Mohr, S. et al, Microfluidics and Nanofluidics 2007, 3, 611-621.*
(Continued)

*Primary Examiner* — Arlen Soderquist
(74) *Attorney, Agent, or Firm* — Crowell & Moring LLP

(57) ABSTRACT

This specimen treatment chip includes: a first fluid module having a first flow channel for performing a first treatment step on an object component in a specimen; a second fluid module having a second flow channel for performing a second treatment step on the object component subjected to the first treatment step; a substrate; and a connection flow channel for connecting the first fluid module and the second fluid module disposed on the substrate.

21 Claims, 30 Drawing Sheets

(51) Int. Cl.
*C12Q 1/68* (2018.01)
*G01N 37/00* (2006.01)
*C12M 1/00* (2006.01)
*G01N 35/08* (2006.01)
*C12M 1/34* (2006.01)
*C12Q 1/6851* (2018.01)
*B01L 7/00* (2006.01)

(52) U.S. Cl.
CPC ............... *C12M 1/00* (2013.01); *C12M 1/34* (2013.01); *C12Q 1/6851* (2013.01); *G01N 35/08* (2013.01); *G01N 37/00* (2013.01); *B01J 2219/00813* (2013.01); *B01L 7/52* (2013.01); *B01L 2200/027* (2013.01); *B01L 2200/028* (2013.01); *B01L 2200/16* (2013.01); *B01L 2300/087* (2013.01); *B01L 2300/0816* (2013.01); *B01L 2300/0883* (2013.01); *B01L 2400/0487* (2013.01)

(58) Field of Classification Search
USPC .................... 422/504; 436/165, 174
See application file for complete search history.

(56) References Cited

U.S. PATENT DOCUMENTS

| | | | | |
|---|---|---|---|---|
| 5,841,036 A * | 11/1998 | Mayeaux | ............... | G01N 35/08 73/863 |
| 5,955,028 A * | 9/1999 | Chow | ............... | B01L 3/502715 204/600 |
| 6,054,277 A * | 4/2000 | Furcht | ............... | B01L 3/5027 422/81 |
| 6,057,149 A * | 5/2000 | Burns | ............... | B01F 5/0085 422/109 |
| 6,086,740 A | 7/2000 | Kennedy | | |
| 6,368,562 B1 * | 4/2002 | Yao | ............... | B01F 5/0604 422/504 |
| 6,495,369 B1 * | 12/2002 | Kercso | ............... | G01N 35/028 204/451 |
| 6,517,234 B1 * | 2/2003 | Kopf-Sill | ............... | B01J 19/0093 366/340 |
| 6,536,477 B1 * | 3/2003 | O'Connor | ............... | B01L 3/5027 137/833 |
| 6,632,400 B1 * | 10/2003 | Brennen | ............... | B01L 3/502707 204/452 |
| 6,828,143 B1 * | 12/2004 | Bard | ............... | B01J 19/0093 422/129 |
| 7,192,557 B2 * | 3/2007 | Wu | ............... | B01L 3/50273 422/20 |
| 7,351,303 B2 * | 4/2008 | Liu | ............... | B01F 13/0059 156/290 |
| 7,569,127 B1 * | 8/2009 | Cho | ............... | B01L 3/502715 137/814 |
| 7,605,002 B2 * | 10/2009 | Summersgill | ............... | B01F 5/0646 422/606 |
| 7,955,840 B2 * | 6/2011 | Belgrader | ............... | B01L 7/525 422/138 |
| 10,173,217 B2 * | 1/2019 | Yamawaki | ............... | B01L 3/502784 |
| 2002/0124896 A1 | 9/2002 | O'Connor et al. | | |
| 2003/0012697 A1 * | 1/2003 | Hahn | ............... | B01F 5/0646 422/400 |
| 2003/0047225 A1 * | 3/2003 | Chuh | ............... | F15B 13/0817 137/884 |
| 2003/0064507 A1 * | 4/2003 | Gallagher | ............... | B82Y 30/00 435/287.2 |
| 2003/0173781 A1 * | 9/2003 | Dodgson | ............... | F16K 99/0011 285/397 |
| 2004/0045891 A1 * | 3/2004 | Gilbert | ............... | B01L 3/502738 210/321.65 |
| 2004/0115094 A1 * | 6/2004 | Gumbrecht | ............... | B01L 3/502715 422/400 |
| 2004/0163717 A1 * | 8/2004 | Gilleo | ............... | B81B 7/0061 137/565.29 |
| 2004/0228771 A1 * | 11/2004 | Zhou | ............... | B01L 9/527 422/503 |
| 2004/0245102 A1 * | 12/2004 | Gilbert | ............... | B01D 67/0062 204/451 |
| 2005/0028878 A1 * | 2/2005 | Reid, II | ............... | F16K 27/003 137/884 |
| 2005/0042149 A1 * | 2/2005 | Bard | ............... | B01J 19/0093 422/130 |
| 2005/0084424 A1 * | 4/2005 | Ganesan | ............... | B01L 3/502715 422/400 |
| 2005/0092662 A1 * | 5/2005 | Gilbert | ............... | B01L 3/50273 210/97 |
| 2005/0161669 A1 | 7/2005 | Jovanovich et al. | | |
| 2005/0255003 A1 * | 11/2005 | Summersgill | ............... | B01F 5/0646 422/606 |
| 2006/0035243 A1 * | 2/2006 | Wenz | ............... | B01L 3/50851 435/6.12 |
| 2006/0051248 A1 | 3/2006 | Cho et al. | | |
| 2006/0078475 A1 * | 4/2006 | Tai | ............... | B01L 9/527 422/400 |
| 2006/0108012 A1 * | 5/2006 | Barrow | ............... | B01L 3/502784 137/806 |
| 2006/0150385 A1 * | 7/2006 | Gilligan | ............... | B01F 5/0646 29/407.08 |
| 2006/0185746 A1 * | 8/2006 | Doyle | ............... | F16K 27/003 137/884 |
| 2006/0201866 A1 * | 9/2006 | Stankowski | ............... | B01D 29/606 210/235 |
| 2006/0205085 A1 * | 9/2006 | Handique | ............... | C12Q 1/6806 436/177 |
| 2006/0207891 A1 * | 9/2006 | Althaus | ............... | G01N 33/54373 205/787 |
| 2006/0257263 A1 | 11/2006 | Ito et al. | | |
| 2007/0036691 A1 * | 2/2007 | Lin | ............... | B01L 7/52 422/130 |
| 2008/0003142 A1 * | 1/2008 | Link | ............... | B01L 3/565 422/82.08 |
| 2008/0014576 A1 * | 1/2008 | Jovanovich | ............... | B01F 11/0071 435/5 |
| 2008/0017306 A1 * | 1/2008 | Liu | ............... | B01F 13/0059 156/297 |
| 2008/0107565 A1 * | 5/2008 | Vivienne | ............... | B01L 3/563 422/63 |
| 2009/0156966 A1 * | 6/2009 | Kontschieder | ............... | B01L 3/502715 600/584 |
| 2009/0170092 A1 * | 7/2009 | Landers | ............... | B01L 3/502746 435/6.13 |
| 2009/0236226 A1 * | 9/2009 | Yuen | ............... | B01J 19/0093 204/600 |
| 2010/0021345 A1 * | 1/2010 | Lohf | ............... | B01J 19/0093 422/68.1 |
| 2010/0154519 A1 * | 6/2010 | Fontana | ............... | H05K 3/30 73/53.01 |
| 2010/0184020 A1 | 7/2010 | Beer | | |
| 2010/0210008 A1 * | 8/2010 | Strand | ............... | G01N 30/6047 435/287.1 |
| 2010/0247380 A1 * | 9/2010 | Lohf | ............... | B01L 3/502715 422/68.1 |
| 2011/0092373 A1 * | 4/2011 | Colston, Jr. | ............... | B01F 3/0807 506/2 |
| 2011/0114190 A1 * | 5/2011 | Wen | ............... | B01L 3/0265 137/1 |
| 2012/0108721 A1 * | 5/2012 | Mazutis | ............... | B01F 3/0807 524/236 |
| 2012/0121480 A1 * | 5/2012 | Frenz | ............... | B01F 5/061 422/502 |
| 2012/0141999 A1 | 6/2012 | Park et al. | | |
| 2013/0203634 A1 | 8/2013 | Jovanovich et al. | | |
| 2015/0000777 A1 * | 1/2015 | Twelftree | ............... | F15B 13/0825 137/884 |
| 2016/0195501 A1 * | 7/2016 | Iovanni | ............... | G01N 30/88 700/282 |
| 2017/0259266 A1 * | 9/2017 | Yamawaki | ............... | B01L 3/502784 |
| 2017/0266654 A1 * | 9/2017 | Sanroma | ............... | B01L 3/502 |

(56) References Cited

U.S. PATENT DOCUMENTS

2018/0149566 A1* 5/2018 Nakano ............ B01L 3/502715
2018/0221881 A1* 8/2018 Tagawa ............ B01L 3/502784

FOREIGN PATENT DOCUMENTS

| | | |
|---|---|---|
| EP | 3216518 A1 | 9/2017 |
| EP | 3360953 A1 | 8/2018 |
| JP | H01-266376 A | 10/1989 |
| JP | 2001-194373 A | 7/2001 |
| JP | 2002-282682 A | 10/2002 |
| JP | 2003-177081 A | 6/2003 |
| JP | 2005-147940 A | 6/2005 |
| JP | 2006-527093 A | 11/2006 |
| JP | 2009-536313 A | 10/2009 |
| JP | 2009-282041 A | 12/2009 |
| JP | 2011-502605 A | 1/2011 |
| JP | 2013-188677 A | 9/2013 |
| JP | 2013-542051 A | 11/2013 |
| JP | 2013-253787 A | 12/2013 |
| JP | 2015-529829 A | 10/2015 |
| WO | 2007/133710 A2 | 11/2007 |
| WO | WO 2011/105507 A1 | 9/2011 |
| WO | WO 2012/011234 A1 | 1/2012 |
| WO | 2014/165559 A2 | 10/2014 |
| WO | 2015/141649 A1 | 9/2015 |

OTHER PUBLICATIONS

Reichert, A. et al, Journal of Bionic Engineering 2008, 5, 291-298.*
Tewhey, R. et al, Nature Biotechnology 2009, 27, 1025-1031 plus supplemental material.*
Zeng, Y. et al, Analytical Chemistry 2010, 82, 3183-3190.*
Kintses, B. et al, Current Opinion in Chemical Biology 2010, 14, 548-555.*
Liou, D.-S. et al, Microfluidics and Nanofluidics 2011, 10, 465-474.*
Hatch, A. C. et al, Lab on a Chip 2011, 11,3838-3845.*
Hayes, C. J. et al, Biomolecular Detection and Quantification 2015, 4, 22-32.*
Po Ki Yuen: "SmartBuild—A truly plug-n-play modular microfluidic system", Lab on a Chip, vol. 8, No. 8, Jan. 1, 2008, pp. 1374-1378, ISSN 1473-0197; Cited in the extended European search report dated Aug. 23, 2019 in a counterpart European patent application.
Yi-Fan Hsieh et al: "A Lego®-like swappable fluidic module for bio-chem applications", Sensors and Actuators B: Chemical, Elsevier B.V., NL, vol. 204, Aug. 10, 2014, pp. 489-496, ISSN 0925-4005; Cited in the extended European search report dated Aug. 23, 2019 in a counterpart European patent application.
P. F. Man et al: "Microfluidic Plastic Interconnects for Multi-bioanalysis Chip Modules", Visual Communications and Image Processing; Jan. 20, 2004-Jan. 20, 2004; San Jose, vol. 3224, Sep. 29, 1987, pp. 196-200, ISBN 978-1-62841-730-2; Cited in the extended European search report dated Aug. 23, 2019 in a counterpart European patent application.
The extended European search report dated Aug. 23, 2019 in a counterpart European patent application No. 16853770.2.
The Communication pursuant to Article 94(3) EPC dated Apr. 3, 2020 in a counterpart European patent application No. 16853770.2.
The Chinese Office Action dated May 20, 2020 in a counterpart Chinese patent application No. 201680059960.2.
The Chinese Office Action dated Mar. 17, 2021 in a counterpart Chinese patent application No. 201680059960.2.
The Decision of Refusal dated Sep. 3, 2021 in a counterpart Chinese patent application No. 201680059960.2.

* cited by examiner

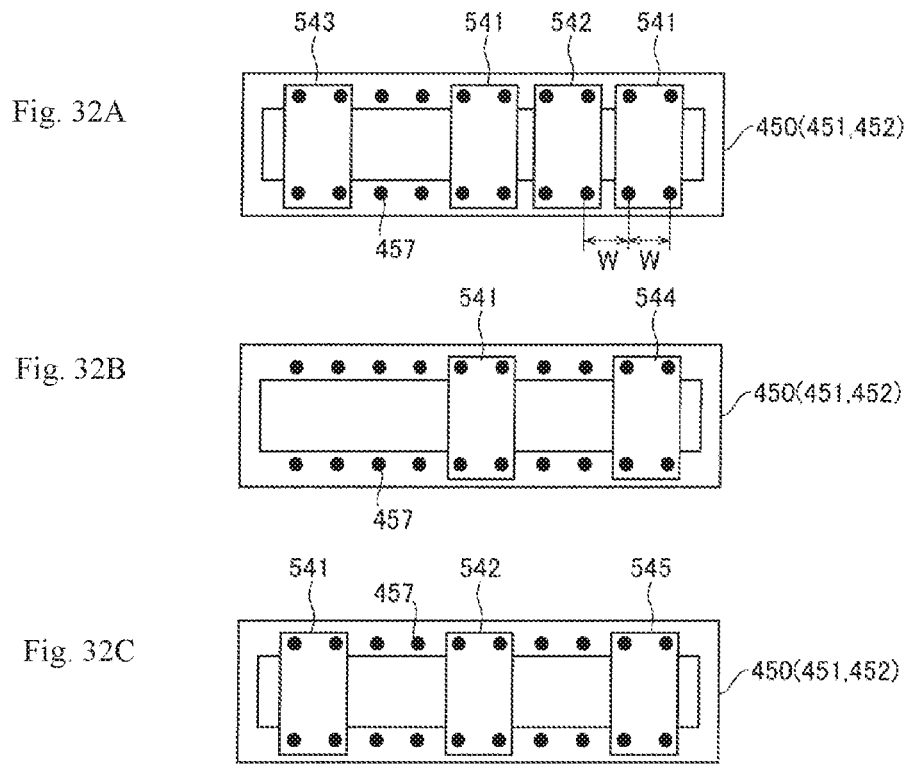
Fig. 32A
Fig. 32B
Fig. 32C
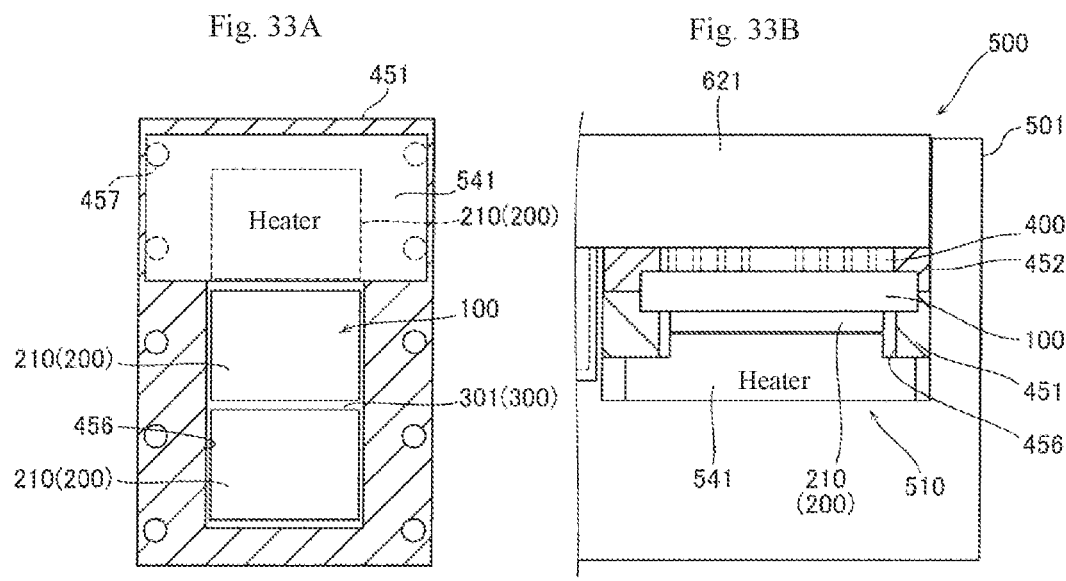
Fig. 33A
Fig. 33B

SPECIMEN TREATMENT CHIP, SPECIMEN TREATMENT APPARATUS, AND SPECIMEN TREATMENT METHOD

RELATED APPLICATIONS

This application is a continuation application of PCT/JP2016/080008 having an international filing date of Oct. 7, 2016, which claims priority to JP2015-200767 filed Oct. 9, 2015. The entire contents of these applications are incorporated herein by reference.

TECHNICAL FIELD

There is a technique for performing specimen treatment using a cartridge-type specimen treatment chip (e.g., refer to Patent Literature 1).

BACKGROUND ART

Patent Literature 1 described above discloses a technique for performing specimen treatment using a specimen treatment chip having a substrate and a plurality of microfluidic modules provided on the substrate. One microfluidic module includes a plurality of reservoirs used for specimen treatment, and flow channels connecting the respective reservoirs to each other. When a specimen containing an object component is provided to flow through one module provided with the plurality of reservoirs, specimen treatment including a plurality of treatment steps is performed. The various kinds of reagent supplied to the plurality of reservoirs and the specimen supplied through an induction pipe are mixed in the flow channels, and are fed to a drain reservoir.

CITATIONS LIST

Patent Literature 1: U.S. Pat. No. 6,086,740

SUMMARY OF INVENTION

Technical Problems

Unfortunately, when specimen treatment including a plurality of treatment steps is performed in a single module as in Patent Literature 1, it is difficult to achieve the specimen treatment such that each treatment step is performed at a place composed of a material suitable for each treatment step, for example. Unlike the case where a specimen and a reagent are mixed simply as in Patent Document 1, a specimen treatment chip applied to a specimen treatment involving various operations such as agitation of a mixed liquid, heating, cooling, magnetic collection, etc., has a flow channel with a complicated structure, so that it is difficult to form a flow channel structure suitable for all treatment steps in a single module. Thus, it is difficult to achieve specimen treatment including various treatment steps.

The present invention is directed to a specimen treatment chip provided in a specimen treatment apparatus to apply specimen treatment including a plurality of treatment steps to an object component in a specimen supplied by the specimen treatment apparatus, the specimen treatment chip being capable of easily achieving desired specimen treatment.

Solutions to Problems

A specimen treatment chip of a first aspect of the present invention is provided in a specimen treatment apparatus to apply specimen treatment including a plurality of treatment steps to an object component in a specimen supplied by the specimen treatment apparatus, and the specimen treatment chip includes: a first fluid module that is provided with a first flow channel for applying a first treatment step to an object component in a specimen supplied by the specimen treatment apparatus; a second fluid module that is provided separately from the first fluid module, and that is provided with a second flow channel for applying a second treatment step to the object component subjected to the first treatment step; a substrate that is provided on its front surface with the first fluid module and the second fluid module; and a connection flow channel for connecting the first fluid module provided on the substrate and the second fluid module provided on the substrate to each other to move the object component from the first flow channel to the second flow channel, wherein the substrate includes a connection port connected to the specimen treatment apparatus to inject an inspection liquid to be used in at least one of the plurality of treatment steps, and the connection port is connected to the flow channels of the respective fluid modules provided on the substrate.

A specimen treatment apparatus of a second aspect of the present invention is configured to treat an object component in a specimen using a specimen treatment chip, and includes: an installation unit that installs a specimen treatment chip having a plurality of fluid modules configured as separated components, and a substrate provided on its front surface with the plurality of fluid modules, to perform a plurality of treatment steps; a lid that is provided to be openable for a specimen treatment chip set in the installation unit, and that has a connector to be connected to a connection port provided in the substrate; a liquid feeder that supplies a specimen containing the object component and a reagent to a specimen treatment chip through the connector to feed liquid in the specimen treatment chip under pressure; and a control unit that controls the liquid feeder so as to supply the specimen and the reagent into the specimen treatment chip in the order of the plurality of treatment steps based on a combination of the plurality of fluid modules to feed the specimen and the reagent to each of the fluid modules.

A specimen treatment apparatus of a third aspect of the present invention is configured to treat an object component in a specimen using a specimen treatment chip, and includes: an installation unit for installing a specimen treatment chip in which a first fluid module for applying a first treatment step to an object component in a specimen, and a second fluid module provided separately from the first fluid module for applying a second treatment step to the object component subjected to the first treatment step, are installed on a front surface of a substrate; a lid that is provided to be openable for a specimen treatment chip set in the installation unit, and that has a connector to be connected to a connection port provided in the substrate; a liquid feeder that supplies a specimen containing an object component to a specimen treatment chip through the connector to feed the specimen; and a control unit that controls the liquid feeder so as to feed liquid in the specimen treatment chip to the first fluid module and the second fluid module in order through a connection flow channel.

A specimen treatment method according to a fourth aspect of the present invention is configured to treat an object component in a specimen using a specimen treatment chip, and includes performing a first treatment step of supplying a specimen containing an object component to a specimen treatment chip in which a first fluid module for applying a first treatment step to an object component in a specimen, and a second fluid module provided separately from the first fluid module for applying a second treatment step to the object component subjected to the first treatment step, are installed on a front surface of a substrate, through a connection port provided in the substrate, to feed the specimen in the specimen treatment chip to the first fluid module; and performing a second treatment step on the object component subjected to the first treatment step by feeding the object component in the first fluid module to the second fluid module through a connection flow channel.

A specimen treatment chip of a fifth aspect of the present invention is provided in a specimen treatment apparatus to apply specimen treatment including a plurality of treatment steps to an object component in a specimen supplied by the specimen treatment apparatus, and the specimen treatment chip includes: a first fluid module that is provided with a first flow channel for applying a first treatment step to an object component in a specimen supplied by the specimen treatment apparatus; a second fluid module that is provided separately from the first fluid module, and that is provided with a second flow channel for applying a second treatment step to the object component with the first treatment step applied; a substrate that is provided on its first surface with the first fluid module and the second fluid module, and that has a first through hole connecting to the first fluid module, and a second through hole connecting to the second fluid module; and a connection flow channel that is provided in a second surface opposite to the first surface of the substrate to connect the first through hole and the second through hole to each other to move the object component from the first flow channel to the second flow channel.

A specimen treatment chip of a sixth aspect of the present invention is provided in a specimen treatment apparatus to apply specimen treatment including a plurality of treatment steps to an object component in a specimen supplied by the specimen treatment apparatus, and the specimen treatment chip includes: a first fluid module that is provided with a first flow channel for applying a first treatment step of forming a droplet containing a mixed liquid of a nucleic acid as the object component, a reagent for an amplification reaction of a nucleic acid, and a carrier of a nucleic acid, in a dispersion medium, to an object component in a specimen supplied by the specimen treatment apparatus; a second fluid module that is provided separately from the first fluid module, and that is provided with a second flow channel for applying a second treatment step of amplifying a nucleic acid in the droplet formed in the first treatment step to the object component subjected to the first treatment step; a substrate that is provided on its front surface with the first fluid module and the second fluid module; and a connection flow channel for connecting the first fluid module and the second fluid module to each other to move the object component from the first flow channel to the second flow channel.

A specimen treatment method according to a seventh aspect of the present invention is configured to treat an object component in a specimen using a specimen treatment chip, and includes: performing a first treatment step of supplying a specimen containing an object component to a specimen treatment chip in which a first fluid module for applying a first treatment step to an object component in a specimen, and a second fluid module provided separately from the first fluid module for applying a second treatment step to the object component subjected to the first treatment step, are installed on a front surface of a substrate, and in which a connection flow channel connecting a first through hole of the substrate connecting to the first fluid module and a second through hole of the substrate connecting to the second fluid module is installed in a second surface of the substrate, opposite to the first surface, to feed the specimen in the specimen treatment chip to the first fluid module; and performing a second treatment step on the object component subjected to the first treatment step by feeding the object component in the first fluid module to the second fluid module through the connection flow channel.

A specimen treatment method according to an eighth aspect of the present invention is configured to treat an object component in a specimen using a specimen treatment chip, and includes: performing a first treatment step of supplying a specimen containing an object component to a specimen treatment chip in which a first fluid module for applying a first treatment step to an object component in a specimen, and a second fluid module provided separately from the first fluid module for applying a second treatment step to the object component subjected to the first treatment step, are installed on a front surface of a substrate, to feed the specimen in the specimen treatment chip to the first fluid module, thereby forming a droplet containing a mixed liquid of a nucleic acid as the object component, a reagent for an amplification reaction of a nucleic acid, and a carrier of a nucleic acid, in a dispersion medium; and performing a second treatment step of amplifying the nucleic acid in the droplet formed in the first treatment step on the object component subjected to the first treatment step by feeding the object component in the first fluid module to the second fluid module through a connection flow channel.

Advantageous Effects of Invention

It is possible to easily achieve desired specimen treatment in a specimen treatment chip installed in a specimen treatment apparatus to apply specimen treatment including a plurality of treatment steps to an object component in a specimen supplied by the specimen treatment apparatus.

BRIEF DESCRIPTION OF DRAWINGS

FIGS. 32A through 32C are schematic diagrams illustrating installation examples (A) to (C) of various units.

FIGS. 33A and 33B include a bottom view (A) illustrating a placement example of a heater unit in a fixture and a schematic sectional view (B) illustrating a placement example of a heater unit in an installation unit.

DETAILED DESCRIPTION OF THE PREFERRED EMBODIMENTS

Hereinafter, embodiments will be described with reference to the drawings.

[Overview of Specimen Treatment Chip]

Figure 1:
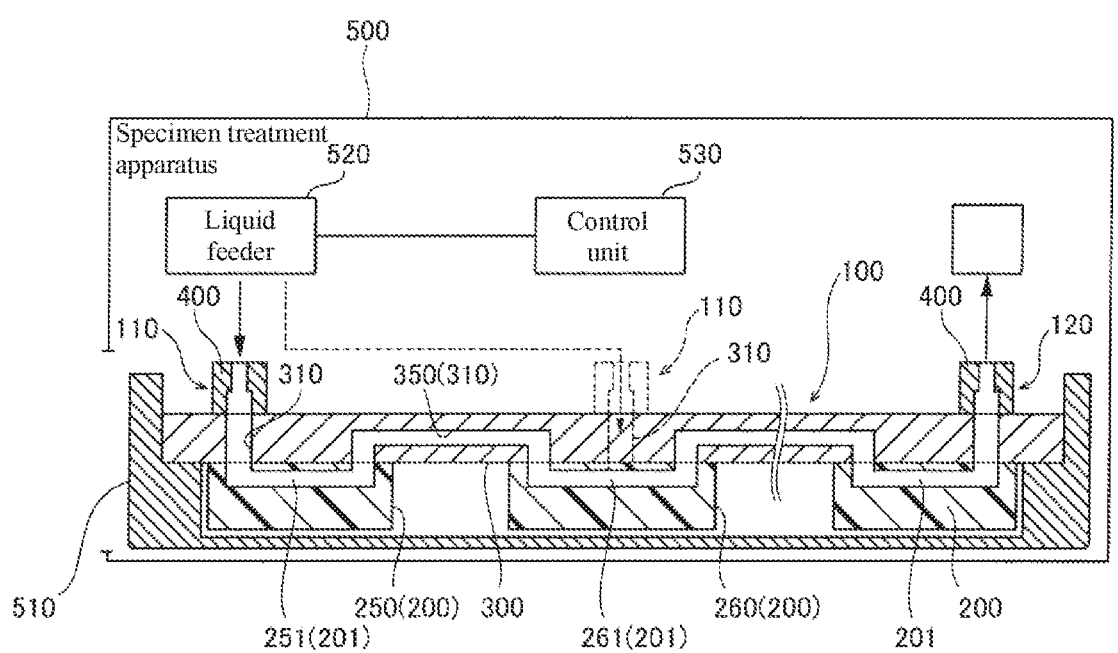
FIG. 1 is a diagram for illustrating an outline of a specimen treatment chip and a specimen treatment apparatus.

With reference to FIG. 1, an overview of a specimen treatment chip according to the present embodiment will be described.

A specimen treatment chip 100 according to the present embodiment is a chip installed in a specimen treatment apparatus 500 to perform specimen treatment including a plurality of treatment steps on an object component in a specimen supplied from the specimen treatment apparatus 500. The specimen treatment chip 100 is a specimen treatment chip of a cartridge type that is configured to be capable of receiving a specimen containing an object component, and that is set in the specimen treatment apparatus 500 to enable the specimen treatment apparatus 500 to perform specimen treatment. In addition, the specimen treatment chip 100 is a microfluidic chip including a fluid module 200 in which a fine flow channel for performing a desired treatment step is formed, as described later. The flow channel is a microchannel having a sectional dimension (width, height, and inner diameter) of 0.1 µm to 1000 µm, for example.

Into the specimen treatment chip 100, liquid such as body fluid or blood (whole blood, serum, or plasma) collected from a patient, or a specimen obtained by applying predetermined pretreatment to collected body fluid or blood, is injected. The object component includes a nucleic acid such as DNA (deoxyribonucleic acid), a cell, an intracellular substance, an antigen or an antibody, a protein, a peptide, and the like, for example. When the object component is a nucleic acid, for example, an extraction liquid in which nucleic acid is extracted from blood or the like by predetermined pretreatment is injected into the specimen treatment chip 100.

The specimen containing the object component injected into the specimen treatment chip 100 is fed into the specimen treatment chip 100 by the specimen treatment apparatus 500. In the course of feeding the specimen, the object component is treated in a plurality of steps in a predetermined order. As a result of the plurality of treatment steps, in the specimen treatment chip 100, a measurement sample suitable for analyzing a specimen, or a liquid sample suitable for a subsequent treatment step using another apparatus, is generated.

The specimen treatment chip 100 includes fluid modules 200 each having a flow channel 201 for performing at least one of the plurality of steps. The specimen treatment chip 100 also includes a substrate 300 on which the fluid modules 200 are disposed. In addition, the specimen treatment chip 100 includes a connection flow channel 350 for connecting the fluid module 200 disposed on the substrate 300 to move liquid between fluid modules.

On the substrate 300, a plurality of types of fluid module 200 for performing a plurality of processes are disposed in order of the plurality of steps. That is, the fluid modules 200 are disposed in series according to the order of the plurality of steps. The plurality of fluid modules 200 each are separately provided on the substrate 300. That is, the plurality of fluid modules 200 are not a plurality of element parts formed in a common member, but are formed as separate parts independent from each other. Each of the fluid modules 200 has a structure in which the flow channel 201 is formed in a block body formed of resin, glass, or the like, for example. In addition, the plurality of fluid modules 200 are installed on the substrate 300 while being separated from each other. Each of the fluid modules 200 is installed on the substrate 300 and connected through the connection flow channel 350, so that liquid can be fed between the fluid modules.

When the specimen is sequentially fed to the multiple kinds of fluid module 200, the treatment steps of the respective fluid modules 200 are performed. The kind of the fluid module 200 is distinguished by structure and function of the fluid module. The structure of the fluid module includes a shape of the flow channel and a material of the fluid module, for example. The function of the fluid module is provided so that the fluid module performs the treatment steps.

The treatment steps performed in the respective fluid modules 200 include the steps of: mixing a specimen and a reagent; reacting a specimen with a reagent; dispersing a specimen containing an object component in a form of fine droplets; breaking the dispersed droplets; separating unnecessary components contained in the specimen from the specimen to clean the unnecessary components; and the like.

Each treatment step may be any treatment as long as it is configured to apply a plurality of steps to a specimen containing an object component to generate a desired sample. The flow channel 201 of the fluid module 200 has a shape suitable for the corresponding one of the treatment steps. Thus, the fluid modules 200 different in a treatment step are different kinds of fluid module, having different function and structure.

The fluid module 200 can be configured so as to perform one step. This enables the fluid module 200 to be a single function module (single step module) dedicated to a step performed by the module. When the number of fluid modules 200 is provided as many as the number of kinds of treatment step that can be performed, various kinds of specimen treatment can be achieved by rearranging a placement order of multiple kinds of fluid module 200. In addition, when the fluid module 200 is configured to be a single-function module, the flow channel 201 of each of the fluid modules 200 can be formed in an optimum flow channel shape for a treatment step of the module, or the fluid module 200 can be formed of an optimum material.

The fluid module 200 may be configured to perform a plurality of steps that are a part of all the steps of the specimen treatment. For example, when two consecutive steps are closely involved, and implementation conditions of the steps, and the like, are similar, or when a plurality of steps can be collectively regarded as one step, it is preferable to form a flow channel 201 for performing the plurality of steps in one fluid module 200.

The flow channel 201 of the fluid module 200 may have any structure as long as it allows liquid injected from an inlet portion of the fluid module 200 to flow. The flow channel 201 has a shape suitable for treatment to be performed in the flow channel. The flow channel 201 is formed so as to have a flow channel width, a flow channel height or a flow channel depth, a flow channel length, and a volume, suitable for treatment to be performed in the flow channel. The flow channel 201 is composed of an elongated tubular passage or channel, for example. The channel can be formed in a linear shape, a curved shape, a zigzag shape, or the like. As described later, the flow channel 201 may have a shape (refer to FIG. 42) in which dimensions of the flow channel, such as width and height of the flow channel, change, a shape in which a part or all of the flow channel expands in a planar shape (refer to FIG. 48), a chamber shape (not illustrated) capable of storing inflowing liquid, or the like.

The specimen treatment chip 100 includes a first fluid module 250 having a first flow channel 251 for performing a first treatment step on an object component in a specimen supplied from the specimen treatment apparatus 500, and a second fluid module 260 having a second flow channel 261 for performing a second treatment step on the object component subjected to first treatment step. The first fluid module 250 and the second fluid module 260 are individually disposed on the substrate 300. The connection flow channel 350 is configured to connect the first fluid module 250 disposed on the substrate 300 and the second fluid module 260 disposed on the substrate 300 to move a specimen from the first flow channel 251 to the second flow channel 261.

The first fluid module 250 and the second fluid module 260 are achieved by a concept of two (a pair of) fluid modules 200 that are configured to feed a specimen to the second fluid module 260 from the first fluid module 250 through the connection flow channel 350, among the plurality of fluid modules 200 provided in the specimen treatment chip 100.

Thus, when the specimen treatment chip 100 includes only two fluid modules 200, an upstream fluid module 200 serves as the first fluid module 250 and a downstream fluid module 200 serves as the second fluid module 260. When the specimen treatment chip 100 includes a large number of fluid modules 200, and a pair of the fluid modules 200 connected by the connection flow channel 350 is paid attention to, among the fluid modules 200, an upstream fluid module 200 serves as the first fluid module 250, and a downstream fluid module 200 serves as the second fluid module 260. When the specimen treatment chip 100 includes three or more fluid modules 200, one fluid module 200 can serve as not only the first fluid module 250 with respect to an upstream fluid module, but also the second fluid module 260 with respect to a downstream fluid module.

The first fluid module 250 and the second fluid module 260 may be the same fluid module. That is, the first treatment step and the second treatment step may be the same treatment step. The first flow channel and the second flow channel may have the same shape. The first fluid module 250 and the second fluid module 260 may be formed of the same material.

The first fluid module 250 and the second fluid module 260 may be provided on the same surface of an upper surface or a lower surface of the substrate 300. The first fluid module 250 and the second fluid module 260 are not necessarily disposed adjacent to each other. When the first flow channel 251 and the second flow channel 261 are connected by the connection flow channel 350, another fluid module 200 may be disposed between the first fluid module 250 and the second fluid module 260, for example. In addition, the first fluid module 250 may be provided on the upper surface, and the second fluid module 260 may be provided on the lower surface of the substrate 300, for example.

The connection flow channel 350 may be provided separately from the first fluid module 250 and the second fluid module 260, and may be a flow channel that connects the first fluid module 250 and the second fluid module 260. That is, the connection flow channel 350 may be a pipe member, or a substrate flow channel 310 formed in the substrate 300, for example.

In a configuration example of FIG. 1, the fluid modules 200 on the substrate 300 are connected to each other through the substrate flow channel 310 provided in the substrate 300. In this configuration example, the connection flow channel 350 is integrally formed with the substrate 300. Accordingly, it is unnecessary to separately provide a connection flow channel composed of a pipe member or the like, so that structure of the specimen treatment chip 100 can be simplified.

The connection flow channel 350 may directly connect the first fluid module 250 and the second fluid module 260, or may connect the first fluid module 250 and the second fluid module 260 through a plurality of members such as a combination of the substrate flow channel 310 and a pipe member. FIGS. 2 to 5 each illustrate a connection example of the first fluid module 250 and the second fluid module 260 using the connection flow channel 350.

Figure 2:
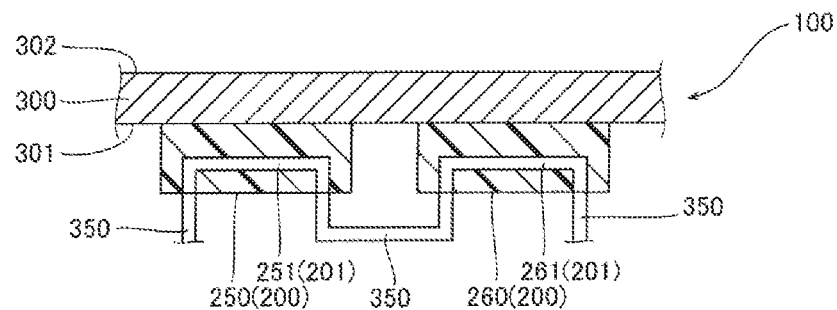
FIG. 2 illustrates a first connection example of a fluid module by a connection flow channel.

In the example of FIG. 2, the connection flow channel 350 directly connects the first flow channel 251 of the first fluid module 250 and the second flow channel 261 of the second fluid module 260 with a pipe member.

Figure 3:
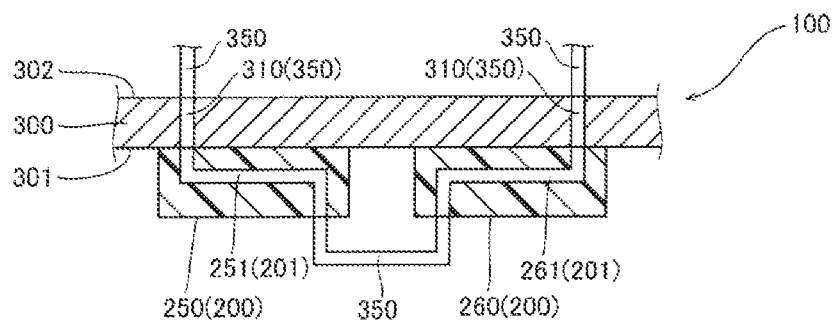
FIG. 3 illustrates a second connection example of a fluid module by a connection flow channel.

In the example of FIG. 3, the connection flow channel 350 for allowing a specimen to flow into the first fluid module 250 and the connection flow channel 350 for allowing a specimen to flow out from the second fluid module 260 are connected to the first flow channel 251 and the second flow channel 261, respectively, through the substrate flow channel 310 of the substrate 300.

Figure 4:
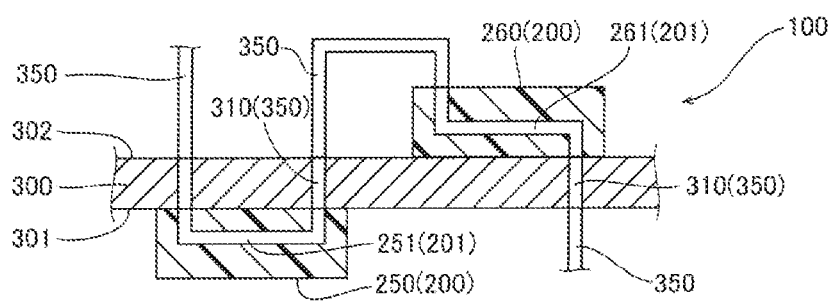
FIG. 4 illustrates a third connection example of a fluid module by a connection flow channel.

In the example of FIG. 4, the connection flow channel 350 includes a substrate flow channel 310 and a pipe member. The first fluid module 250 is disposed on a first surface 301 of the substrate 300 and the second fluid module 260 is disposed on a second surface 302 opposite to the first surface 301 of the substrate 300. The first flow channel 251 of the first fluid module 250 is connected to the second flow channel 261 of the second fluid module 260 through the connection flow channel 350 of the substrate 300. This enables both sides of the specimen treatment chip 100 to be used, so that the fluid modules 200 can be integrated to downsize the specimen treatment chip 100.

Figure 5:
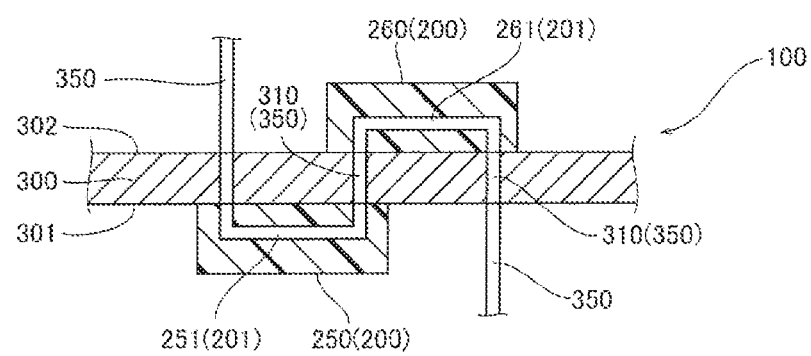
FIG. 5 illustrates a fourth connection example of a fluid module by a connection flow channel.

FIG. 5 illustrates a configuration example in which the substrate flow channel 310 serves as the connection flow channel 350. The first flow channel 251 of the first fluid module 250 on a lower surface side and the second flow channel 261 of the second fluid module 260 on an upper surface side are directly connected by the substrate flow channel 310. As described above, the substrate 300 may integrally include the connection flow channel 350 connected to the fluid module 200.

These configurations allow liquid to be fed to the respective fluid modules 200 through the connection flow channel 350 in accordance with the order of the plurality of steps.

As illustrated in FIG. 1, the substrate 300 can be provided with a port 110 for injecting an inspection liquid to be used in at least one of the plurality of treatment steps. There may be provided a port 110 for injecting a specimen containing an object component into the specimen treatment chip 100, and a port 120 for recovering liquid from the specimen treatment chip 100. As indicated by the broken line in FIG. 1, a port 110 for injecting liquid such as a reagent used in the corresponding one of steps into the specimen treatment chip 100 may be provided on the substrate 300, if necessary. These ports can also be formed in the connection flow channel 350.

The first fluid module 250 and the second fluid module 260 are configured so as to respectively feed liquid through the first flow channel 251 and the second flow channel 261 by using pressure supplied from the specimen treatment apparatus 500 through the port 110 for injecting a specimen. That is, the specimen treatment chip 100 is configured so as to operate in cooperation with the specimen treatment apparatus 500. This eliminates the need to provide a structure for feeding liquid to a specimen treatment chip 100 side, so that the specimen treatment chip 100 can be downsized.

In the present embodiment, the specimen treatment chip 100 is configured as described above to perform the plurality of treatment steps separately in the first fluid module 250 and the second fluid module 260, so that there is provided the connection flow channel 350 separately from the first fluid module 250 and the second fluid module 260 to connect them to each other. Thus, it is possible to easily achieve desired specimen treatment in the specimen treatment chip 100 installed in the specimen treatment apparatus 500 to apply specimen treatment including a plurality of treatment steps to a specimen in liquid supplied by the specimen treatment apparatus 500.

In addition, the first treatment step and the second treatment step are different from each other, for example. That is, the first fluid module 250 and the second fluid module 260 perform treatment steps different from each other. This configuration enables each of the first fluid module 250 and the second fluid module 260 to be optimized to a structure suitable for the treatment step to be performed by the corresponding one of the modules. In addition, when a plurality of kinds of fluid module 200 for performing various treatment steps is provided, the specimen treatment chip 100 is applicable to various kinds of specimen treatment by simply changing the kind of the fluid module 200 to be disposed on the substrate 300 and rearranging placement order of the fluid modules 200. Thus, even when the specimen treatment includes a plurality of steps, a structure suitable for each treatment step can be obtained to enable application to various kinds of specimen treatment to be facilitated.

[Overview of Specimen Treatment Apparatus]

Next, an overview of a specimen treatment apparatus according to the present embodiment will be described.

A specimen treatment apparatus 500 is configured to treat an object component in a specimen using a specimen treatment chip 100. Contents of specimen treatment are determined by a kind and placement of a first fluid module 210 installed in the specimen treatment chip 100. Thus, the specimen treatment apparatus 500 can perform different kinds of specimen treatment depending on the kind of the specimen treatment chip 100 to be used.

The specimen treatment apparatus 500 includes an installation unit 510 for installing the specimen treatment chip 100, a liquid feeder 520, and a control unit 530 for controlling the liquid feeder 520.

The installation unit 510 is formed in a shape corresponding to the specimen treatment chip 100 to support the specimen treatment chip 100. The installation unit 510 has a structure such that at least one of an upper side and a lower side of the specimen treatment chip 100 is opened to be connected to a flow channel of the specimen treatment chip 100 and to allow a treatment unit used for various treatment steps in the specimen treatment chip 100 to be installed. The installation unit 510 can have a recessed or frame-like structure as illustrated in FIG. 1, for example. In the present example, the installation unit 510 supports a substrate 300 in the specimen treatment chip 100.

The liquid feeder 520 has a function of supplying and feeding a specimen containing an object component to the specimen treatment chip 100. The liquid feeder 520 is composed of a combination of a pump and a valve, for example, and feeds a specimen in the specimen treatment chip 100 under pressure. The liquid feeder 520 may be configured so as to supply not only a specimen containing an object component but also various reagents to be used in the specimen treatment chip 100 to the specimen treatment chip 100, for example. The liquid feeder 520 is connected to a reservoir for storing a specimen containing an object component and a reservoir for storing various reagents to supply the specimen and the reagents, for example.

In addition, the liquid feeder 520 can advance liquid in the specimen treatment chip 100 according to the order of steps by supplying positive pressure, and can discharge the liquid from the specimen treatment chip 100. The liquid feeder 520 may feed and discharge the liquid of the specimen treatment chip 100 by supplying negative pressure.

The control unit 530 controls the liquid feeder 520 on the basis of a combination of a plurality of fluid modules 200 so as to supply a specimen and a reagent to the specimen treatment chip 100 in accordance with the order of the plurality of treatment steps to sequentially feed the specimen and the reagent to each of the fluid modules 200. More specifically, the control unit 530 controls the liquid feeder 520 such that the liquid in the specimen treatment chip 100 is fed to the flow channel 201 of each of the plurality of kinds of fluid module 200 through the connection flow channel 350 according to the order of the plurality of steps.

The liquid feeder 520 is controlled by controlling supply pressure of the liquid feeder 520 with a flow sensor or a pressure sensor provided in a liquid supply path, for example. When a metering pump, such as a syringe pump and a diaphragm pump, is used as the liquid feeder 520, a flow rate sensor is not necessarily required.

When treatment units used for various respective treatment steps are installed in the specimen treatment apparatus 500, the control unit 530 may control these treatment units. The units used for various treatment steps include a heater unit or a cooling unit for controlling temperature of liquid, a magnet unit for applying a magnetic force to the liquid, a camera unit for imaging the liquid, and a detection unit for detecting a specimen or a label in the liquid, for example. These treatment units are provided corresponding to at least one of the plurality of fluid modules 200, and are configured to operate when the corresponding fluid modules 200 perform the treatment steps.

In the present embodiment, such an apparatus configuration allows the control unit 530 to control the liquid feeder 520 so as to supply a specimen containing an object component to the specimen treatment chip 100 so that liquid in the specimen treatment chip 100 is fed into the flow channel 201 of each of the plurality of kinds of fluid module 200 through a substrate flow channel 310 of the substrate 300 according to the order of a plurality of steps. This allows the respective fluid modules 200 to sequentially perform treatment steps corresponding to a combination of the fluid modules 200.

In the present embodiment, treatment steps of an object component are allocated to a plurality of corresponding fluid modules 200, so that a specimen containing an object component is sequentially fed to each of the fluid modules 200 to enable each of the fluid modules 200 to sequentially perform the corresponding one of the plurality of steps. Thus, it is possible to easily achieve desired specimen treatment in the specimen treatment chip 100 installed in the specimen treatment apparatus 500 to apply specimen treatment including a plurality of treatment steps to an object component in a specimen supplied by the specimen treatment apparatus 500.

In addition, when a plurality of fluid modules 200 is provided for corresponding treatment steps to be performed by the respective fluid modules 200, the specimen treatment chip 100 and the specimen treatment apparatus 500 are applicable to various kinds of specimen treatment assay by simply changing the kind of the fluid module 200 to be disposed on the substrate 300 and rearranging placement order of the fluid modules 200. Thus, even when the specimen treatment using the specimen treatment chip 100 includes a plurality of steps, a structure suitable for each treatment step can be obtained to enable application to various kinds of specimen treatment to be facilitated.

[Configuration Example of Specimen Treatment Chip]

Figure 6:
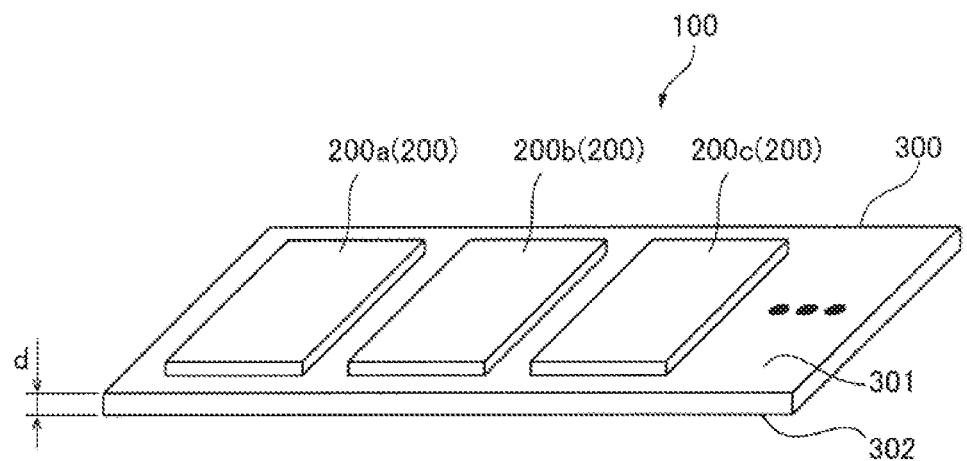
FIG. 6 is a perspective view illustrating a configuration example of a specimen treatment chip.

FIG. 6 illustrates a configuration example of the specimen treatment chip 100 according to the present embodiment. The specimen treatment chip 100 includes the plurality of fluid modules 200 and the substrate 300. On the substrate 300, a plurality of kinds of fluid module 200 having different respective functions is installed. In the example of FIG. 6, when a specimen containing an object component, a reagent, or the like, sequentially flows through fluid modules 200a, 200b, and 200c, an assay corresponding to a combinations of the plurality of kinds of fluid module is performed. Each of the fluid modules 200a, 200b, and 200c is a different kind of fluid module. When a combination of the fluid modules 200 installed on the substrate 300 is changed, various assays corresponding to combinations can be performed. There is no limitation on the number of fluid modules 200 installed on the substrate 300. The fluid module 200 may be different in shape for each kind.

Figure 7:
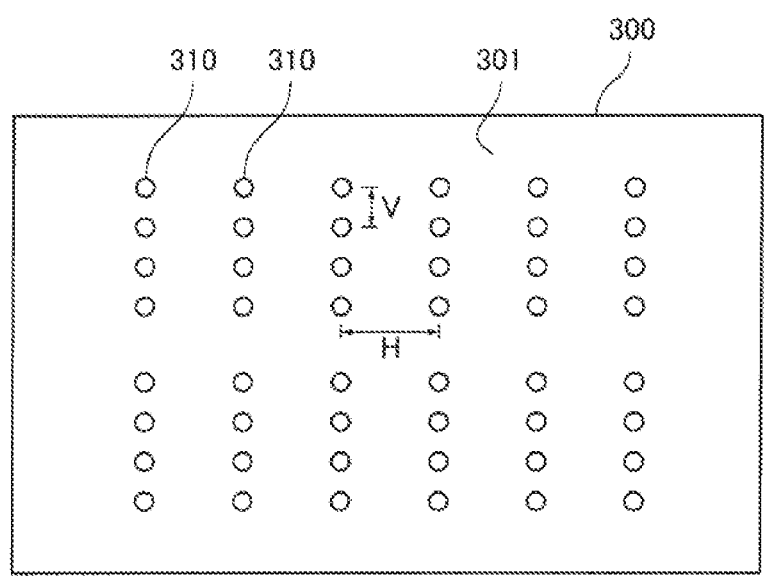
FIG. 7 is a plan view illustrating a configuration example of a substrate of a specimen treatment chip.

FIG. 7 illustrates a configuration example of the substrate 300. The substrate 300 has a plurality of substrate flow channels 310. The substrate 300 has the shape of a flat plate, and has a first surface 301 being a main surface, and a second surface 302. The second surface 302 is opposite to the first surface 301. While an upper surface of the substrate 300 serves as the first surface 301 in FIG. 6, a lower surface thereof may serve as the first surface 301. The substrate 300 is formed of a material having rigidity. For example, the substrate 300 is formed of glass. As a result, even when pressure of the liquid to be supplied to the fluid module 200 is increased according to a treatment step, sufficient pressure resistance performance can be secured for the substrate 300.

The substrate 300 has a thickness "d" of 1 mm or more and 5 mm or less, for example. This enables the substrate 300 to be formed to have a sufficiently large thickness as compared with a flow channel height (on the order of 10 μm to 500 μm) of the flow channel 201 formed in the fluid module 200. As a result, sufficient pressure resistance performance can be easily secured for the substrate 300.

The substrate flow channel 310 is a through hole passing through the substrate 300 in its thickness direction, for example. The substrate flow channel 310 is connected to the flow channel 201 of the fluid module 200, and can serve as a port 110 for supplying liquid and reagent into the specimen treatment chip 100 and a port 120 for recovering liquid from the inside of the specimen treatment chip 100. When the port 110 and the port 120 are provided on the substrate 300, it is possible to easily secure pressure resistance performance when liquid is supplied to the port 110 or the port 120. For example, the port 110 and the port 120 each are formed by a through hole in the example of FIG. 7, and are connected from one surface side of the substrate 300 to the flow channel 201 of the fluid module 200 disposed on the other surface side. This enables structure of the specimen treatment chip 100 to be simplified.

In the example of FIG. 7, the substrate 300 has two sets of substrate flow channels 310 of four rows by six columns. When a plurality of sets of substrate flow channels 310 is provided in the substrate 300, a plurality of columns of the fluid modules 200 for performing a series of treatment steps can be formed on the substrate 300. In this case, it is possible to perform the same or different treatment steps in parallel in one specimen treatment chip 100. The number of substrate flow channels 310 and the number of sets of substrate flow channels 310, provided in the substrate 300, are not limited to those in the example of FIG. 7. The substrate 300 may have one set of substrate flow channels 310 of eight rows by six columns.

The substrate flow channels 310 are disposed at a predetermined pitch, for example. In the example of FIG. 7, each of the substrate flow channels 310 is arranged at a pitch V in the vertical direction and a pitch H in the horizontal direction. In this case, the fluid module 200 can be disposed at an arbitrary position on a pitch unit basis on the substrate 300, and the flow channel 201 can be connected to an arbitrary substrate flow channel 310. Thus, even when a combination of the fluid modules 200 is changed, any combination and placement of the fluid modules 200 can be easily achieved on the substrate 300.

Figure 8:
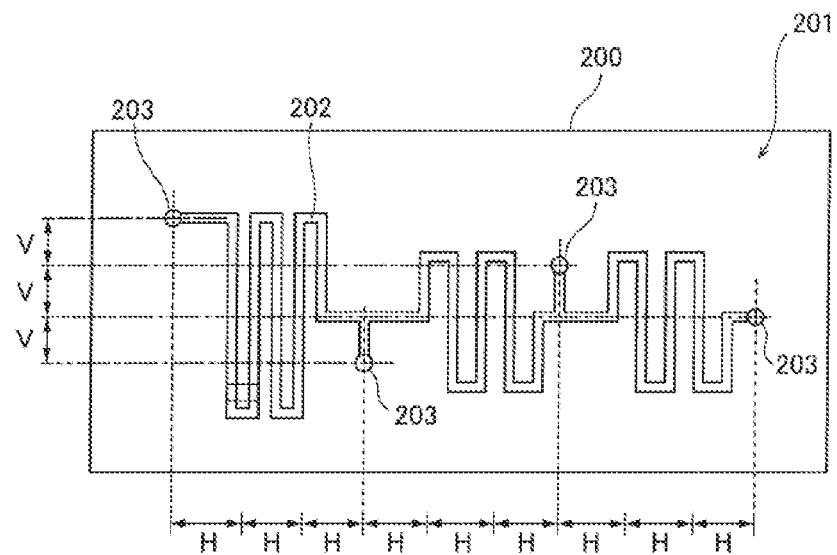
FIG. 8 is a plan view illustrating a configuration example of a fluid module.

FIG. 8 illustrates a configuration example of the fluid module 200. The flow channel 201 of the fluid module 200 includes a channel 202 through which liquid such as a specimen or a reagent flows, and connection portions 203. Each of the connection portions 203 is used to inject liquid into the channel 202, or to suck out liquid from the channel 202.

The connection portions 203 are disposed on the fluid module 200 so as to coincide with pitches of the substrate flow channels 310 of the substrate 300. That is, the connection portions 203 are disposed on the fluid module 200 at pitches that are integral multiples of the respective pitches V and H of the substrate flow channel 310 of the substrate 300. The channel 202 is disposed so as to connect between the corresponding connection portions 203 disposed at a predetermined pitch.

Figure 9:
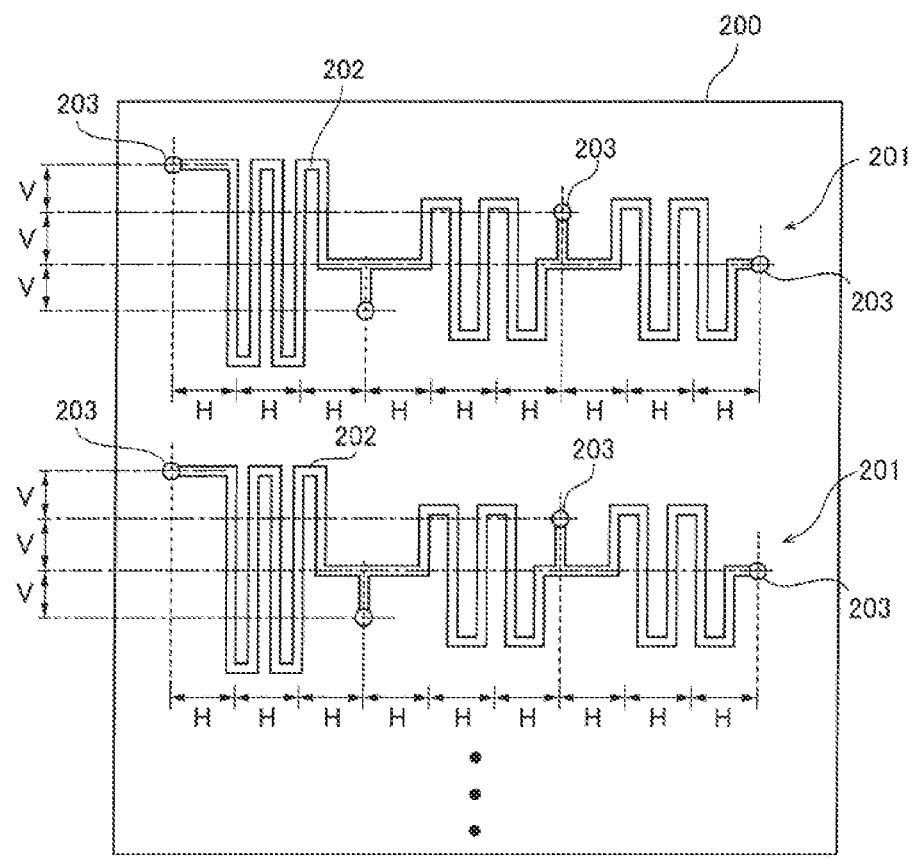
FIG. 9 is a plan view illustrating another configuration example of a fluid module.

As illustrated in FIG. 9, a plurality of sets of the connection portions 203 disposed at a predetermined pitch and the channel 202 may be disposed in the fluid module 200. In this case, it is possible to perform treatment steps to be performed in the fluid module 200 in the plurality of sets thereof in parallel, or to perform the treatment steps multiple times by causing liquid to flow sequentially to the flow channel 201 of each of the sets.

Figure 10:
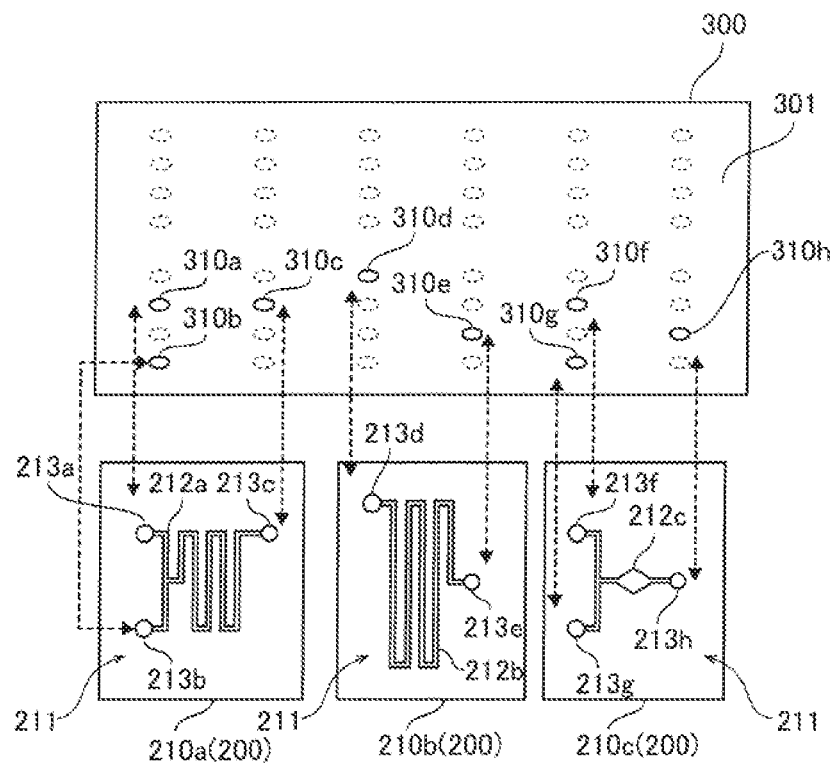
FIG. 10 is a schematic plan view illustrating an example of placement of fluid modules on a substrate.
Figure 11:
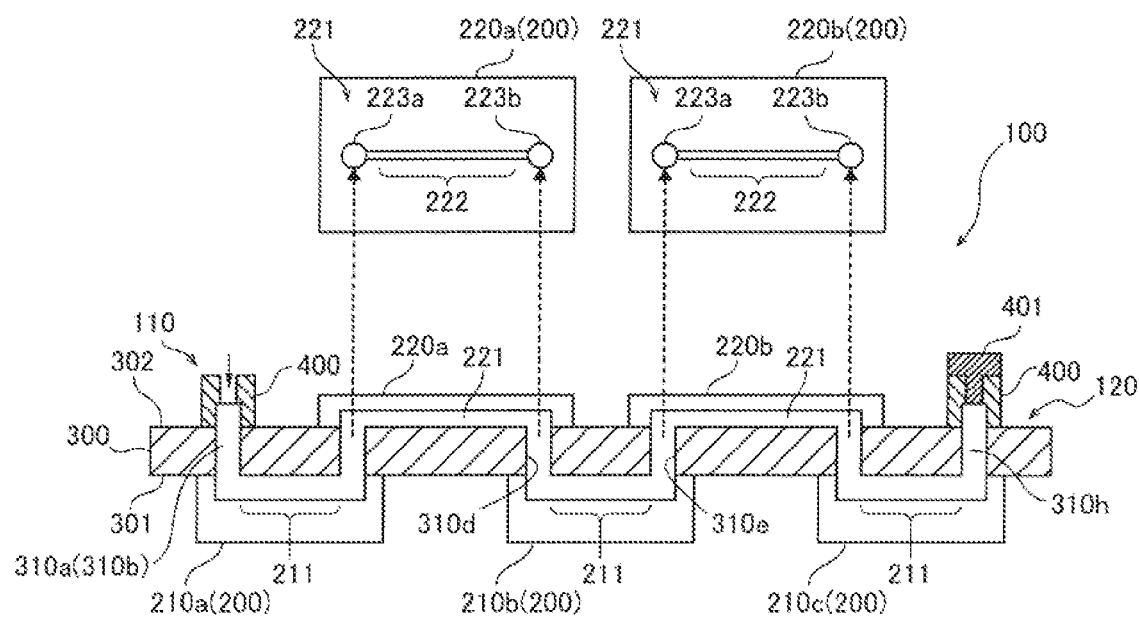
FIG. 11 is a schematic longitudinal sectional view illustrating an example of placement of a fluid module on a substrate.

FIGS. 10 and 11 each illustrate an example of placement of the fluid modules 200 on the substrate 300. In the example of FIG. 10, fluid modules 210a, 210b, and 210c are disposed on the first surface 301 of the substrate 300. As illustrated in FIG. 10, each of the fluid modules 210a to 210c has a different flow channel shape. That is, the first flow channel 251 of the first fluid module 250 and the second flow channel 261 of the second fluid module 260 each have a different shape. This enables a flow channel shape suitable for each of the first treatment step and the second treatment step to be achieved.

When the substrate flow channel 310 is formed as a through hole, connection among the fluid modules 210a to 210c can be configured as illustrated in FIG. 11.

In the configuration example of FIG. 11, the specimen treatment chip 100 further includes a fluid module 220. The fluid module 220 is disposed on a second surface 302 opposite to the first surface 301 of the substrate 300 on which the fluid module 210 is disposed. The fluid module 220 includes a flow channel 221. The flow channel 221 includes a channel 222 and a connection portion 223, and is a connection module having a function of connecting the fluid modules 210 to each other. Thus, hereinafter, the fluid module 220 is referred to as a connection module 220. The connection module 220 is not provided with a flow channel for performing treatment steps of an object component. That is, in the present example, the connection flow channel 350 includes not only the substrate flow channel 310 but also the connection module 220.

One (first fluid module 250) of the fluid modules 210 adjacent to each other on the substrate 300 is connected to the other of the fluid modules 210 (the second fluid module 260) through the corresponding substrate flow channel 310 and flow channel 221 of the connection module 220. This enables liquid from the fluid module 210 on an upstream side to once pass through the substrate 300 to be fed to the connection module 220 on an opposite surface, and to again pass through the substrate 300 to be fed to the fluid module 210 on a downstream side. As a result, the substrate flow channel 310 for feeding liquid between adjacent fluid modules 210 can be simplified in structure, so that the substrate 300 can be simplified in structure.

The connection module 220 can include a flow channel 221 for feeding liquid between two adjacent fluid modules 210 on the first surface 301 of the substrate 300. As described above, when the flow channel 221 for feeding liquid is provided in the connection module 220 in place of a flow channel for performing a predetermined step, the connection module 220 can be simplified in structure. As described later, a fluid module 200 including a flow channel for performing a step may be provided in place of the connection module 220.

As illustrated in FIG. 10, the substrate flow channel 310 of the substrate 300 may be through holes provided at positions corresponding to the plurality of first flow channels 211 disposed on the substrate 300. This enables shape of the substrate flow channel 310 to be simple as much as possible, so that the substrate 300 can be further simplified in structure.

The substrate flow channels 310 may be formed only at corresponding positions required for connection to various fluid modules 200 disposed on the substrate 300. In the example of FIG. 10, through holes are formed at respective positions of the substrate flow channels 310a to 310h indicated by solid lines, for example. The substrate flow channels 310 may be formed at a predetermined pitch on the entire substrate 300 as illustrated in FIG. 3.

Each fluid module 200 (the fluid module 210 and the connection module 220) is connected to the substrate 300 by solid phase bonding, for example. The solid phase bonding can use a method in which bonding surfaces are subjected to plasma treatment to form OH radicals and the bonding surfaces are bonded by hydrogen bonding, and a method such as vacuum pressure bonding, for example. The fluid module 200 and the substrate 300 can be firmly bonded by solid phase bonding. Even when pressure of liquid to be supplied to these fluid modules is increased according to a treatment step, sufficient pressure resistance performance can be secured for the substrate 300. The fluid module 200 may be connected to the substrate 300 by an adhesive or the like.

The substrate 300 may include a substrate flow channel 310 for injecting an inspection liquid to be used in at least one of a plurality of steps into the specimen treatment chip 100. The substrate flow channel 310 for injecting liquid is connected to at least one first flow channel 211 of the plurality of fluid modules 210 disposed on the substrate 300. This enables a specimen containing an object component, and a reagent, to be injected into the substrate 300 in place of a fluid module to be fed from the substrate 300 to the fluid module 210. The substrate 300 has a higher degree of freedom in structure than the fluid module in which a treatment step is performed, so that a material or a structure, securing pressure resistance performance, can be easily achieved, for example. Thus, when an inspection liquid is injected into the substrate 300 first, it is possible to stably supply liquid under sufficient pressure.

In the examples of FIGS. 10 and 11, each of the substrate flow channels 310a and 310b of the substrate 300 serves as the port 110 for injecting liquid. The substrate flow channel 310a and the substrate flow channel 310b are connected to a connection portion 213a and a connection portion 213b of the fluid module 210a, respectively. For example, a specimen containing an object component is injected into the fluid module 210a from the substrate flow channel 310a, and a reagent is injected into the fluid module 210a from the substrate flow channel 310b. In the example of FIG. 10, it is assumed that the object component is DNA, and the reagent is a reagent for amplifying DNA by polymerase chain reaction (PCR).

The specimen and the reagent are injected into the substrate flow channel 310 with a jig such as a connector 400. The jig such as the connector 400 is connected to an end portion of the substrate flow channel 310, on a side opposite to an end portion on a first flow channel 211 side. That is, the jig such as the connector 400 is installed on the second surface 302 opposite to the first surface 301 of the substrate 300 on which the fluid modules 210a to 210c are disposed.

When the substrate flow channel 310 is formed as a through hole, it is preferable to provide the substrate flow channel 310 for injecting an inspection liquid at a position different from a position at which the connection module 220 is disposed. This enables the connection module 220 and the jig to avoid interfering with each other when the jig such as the connector 400 is disposed.

The fluid module 210a has a function of mixing liquids injected through the substrate flow channels 310a and 310b, for example. The specimen and the reagent injected from the connection portions 213a and 213b, respectively, are mixed in the course of flowing through the channel 212a. The mixed liquid is discharged from the fluid module 210a through the connection portion 213c.

The liquid discharged from the fluid module 210a is injected into a connection portion 213d of the fluid module 210b through substrate flow channels 310c and 310d of the substrate 300. The substrate flow channels 310c and 310d of the substrate 300 are connected by a flow channel 221 of a connection module 220a.

The fluid module 210b performs a step of reacting an object component in an injected specimen with a reagent, for example. Below the fluid module 210b, a heater for forming a plurality of temperature zones is disposed, for example. Liquid injected into the channel 212b through the connection portion 213d sequentially passes through the plurality of temperature zones to be heated while the liquid flows through the channel 212b. DNA as an object component is amplified by being heated in the plurality of temperature zones to react with a reagent. The specimen containing the amplified object component is discharged from the fluid module 210b through a connection portion 213e.

The liquid discharged from the fluid module 210b is injected into a connection portion 213f of the fluid module 210c through substrate flow channels 310e and 310f of the substrate 300. The substrate flow channels 310e and 310f of the substrate 300 are connected by a connection module 220b.

The fluid module 210c performs a reaction step different from that of the fluid module 210b, for example. The reagent is injected from a connection portion 213g of the fluid module 210c, for example. In the example of FIG. 10, the reagent is a hybridization reagent that contains a marking substance that binds to DNA. The liquid injected from the connection portion 213f and the reagent injected from the connection portion 213g are mixed in the channel 212c. The liquid mixed in the channel 212c is heated by a heater that is disposed below the fluid module 210c and is controlled for temperature. In the heated mixed liquid, the marking substance in the reagent binds to DNA as an object component.

The liquid containing the DNA binding to the marking substance is discharged from the fluid module 210c through a connection portion 213h. The liquid containing the DNA binding to the marking substance is recovered from the substrate flow channel 310h of the substrate 300, for example. The DNA contained in the recovered liquid is detected by a device capable of detecting fluorescence of the marking substance, for example.

The DNA binding to the marking substance may be detected in the specimen treatment apparatus 500 on which the specimen treatment chip 100 is installed. In this case, the fluid module 210c is formed of a transparent material with low autofluorescence, for example. As a result, the fluid module 210c is configured such that fluorescence of the marking substance can be detected in the channel 212c.

(Another Configuration Example of Specimen Treatment Chip: Flow Channel Height)

Figure 12:
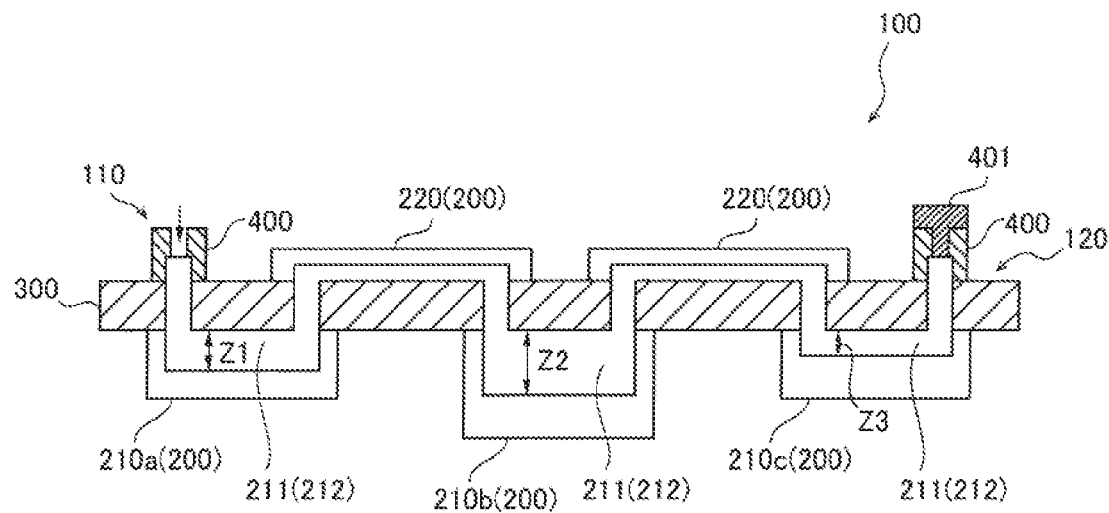
FIG. 12 is a longitudinal sectional view illustrating a first modification of a specimen treatment chip.

FIG. 12 illustrates a configuration example of a specimen treatment chip 100 in which a plurality of kinds of fluid module 210 different in height of a flow channel 211 is connected to a substrate 300.

In the example of FIG. 12, the flow channel 211 of each of the plurality of kinds of fluid module 210 has a different height Z in a thickness direction of the substrate 300. The height of the channel 211 is a height of a channel 212 in the channel 211.

A flow channel height of the flow channel 211 affects a flow rate of liquid flowing through the channel 212, assuming that a flow channel width is constant. For example, as the channel 212 decreases in height, a liquid flow rate increases. When function as well as use of the fluid module 210 is different, a suitable flow rate is also different. In the present embodiment, the fluid module 210 can be configured for each kind of step, so that the fluid module 210 can be formed by selecting a flow channel 211 with an appropriate height suitable for function and use of the fluid module 210.

Thus, in the example of FIG. 12, it is preferable that the flow channel 211 of each of the plurality of kinds of fluid module 210 has a height suitable for a step to be performed in the flow channel 211. This enables a channel 212 with a height suitable for its use and function to be provided for each of the kinds of fluid module 210, so that treatment efficiency in a step performed in the flow channel 211 can be improved.

As an example of the height Z of the flow channel 211, the specimen treatment chip 100 includes fluid modules 210a and 210c that respectively includes flow channels 211 with flow channel heights Z1 and Z3 each of which is 10 μm or more and 20 μm or less, and a fluid module 210b that includes a flow channel 211 with a flow channel height Z2 of 50 μm or more and 500 μm or less, for example.

When the fluid modules 210a and 210c each including the flow channel 211 with a height of about 10 μm to 20 μm are formed, the flow channel 211 is typically molded by a precision Si mold produced by photolithography and etching process. When a fluid module is molded with a Si mold, channels 212 of a flow channel 211 formed in the fluid module are molded to the same height. Thus, when a plurality of kinds of channel 212 each having a different function is formed in one fluid module, it is difficult to select a channel height suitable for a function, in a molding method using a Si mold. While it is possible to change a channel height in a fluid module by molding the fluid module with a machined mold, it is difficult to achieve accuracy of about 10 μm to 20 μm in height by molding with a machined mold. That is, in molding by a machined mold, it is difficult to mix a flow channel with a small flow channel height and a flow channel with a large flow channel height, as described above.

In contrast, when a fluid module 210 is provided for each kind of step as in the present embodiment, channels 212 with small flow channel heights Z1 and Z3, and a channel 212 with a large flow channel height Z2, can be prevented from being mixed in the same fluid module. As a result, it is possible to easily obtain a specimen treatment chip 100 with a different flow channel height for each treatment step by selecting a molding method suitable for a size of each flow channel. This improves accuracy of fluid control by the specimen treatment chip 100.

(Another Configuration Example of Specimen Treatment Chip: Constituent Material)

Figure 13:
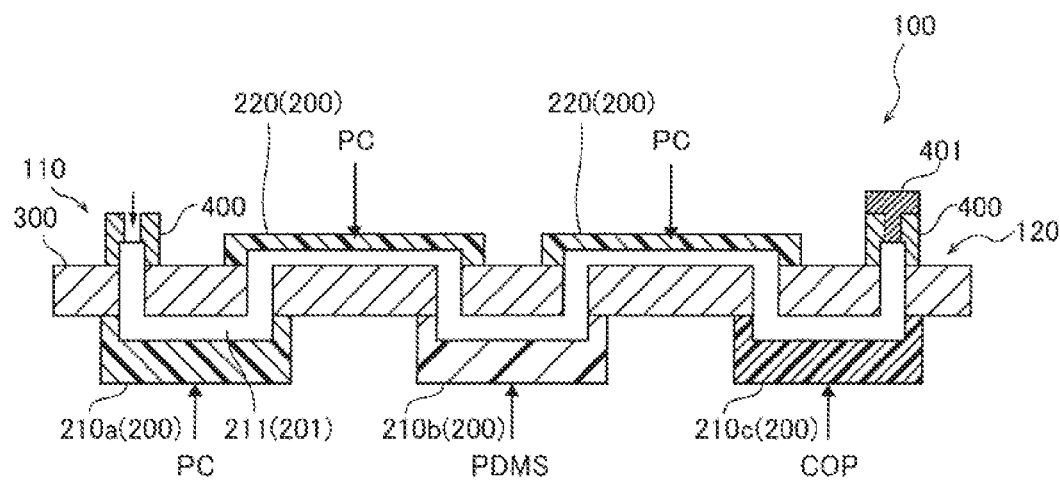
FIG. 13 is a longitudinal sectional view illustrating a second modification of a specimen treatment chip.

FIG. 13 illustrates a configuration example of a specimen treatment chip 100 in which a plurality of kinds of fluid module 200 different in material is connected to a substrate 300.

In the example of FIG. 13, each of the plurality of kinds of fluid module 200 is formed of a different material. The plurality of kinds of fluid module 200 each have a different function to perform a different treatment step, or are used for a different use. That is, a first fluid module 250 for performing a first treatment step and a second fluid module 260 for performing a second treatment step are formed of materials different from each other. In the present embodiment, a fluid module 200 can be configured for each kind of step, so that the fluid module 200 can be formed by selecting a material suitable for function and use of the fluid module 200.

Thus, in the example of FIG. 13, it is preferable that each of the plurality of kinds of fluid module 200 is formed of a material suitable for a step (a first treatment step, or a second treatment step) to be performed in each flow channel 201. As a result, the fluid module 200 is formed of a material suitable for its use and function for each kind of fluid module 200, so that performance of the fluid module 200 suitable for use and function required can be improved for each kind of fluid module 200.

In the example of FIG. 13, a material of each fluid module is as follows: polycarbonate (PC) for a fluid module 210a; polydimethylsiloxane (PDMS) for a fluid module 210b; cycloolefin polymer (COP) for a fluid module 210c; and polycarbonate (PC) for a fluid module 220.

A material constituting a fluid module is not limited to the materials described above. Correspondence between examples of function and use of a fluid module and examples of preferred material is as follows (A) to (E) below.

(A) A fluid module that controls temperature of liquid with a heater or the like:

A material with heat resistance (e.g., polycarbonate (PC), and the like)

(B) A fluid module that uses oil for forming an emulsion, or the like:

A material with hydrophobicity or a material subjected to fluorination treatment (e.g., polydimethylsiloxane (PDMS), polymethyl methacrylate resin (PMMA), or the like)

(C) A fluid module using a chemical agent:

A material with chemical resistance (e.g., polycarbonate, polystyrene (PS), or the like)

(D) A fluid module used for fluorescence detection:

A material with low autofluorescence (e.g., cycloolefin copolymer (COC), or cycloolefin polymer (COP))

(E) A fluid module requiring high wettability:

A material subjected to hydrophilic treatment (e.g., glass, polycarbonate, or the like)

(Another Configuration Example of Specimen Treatment Chip: Quality Control Function)

Figure 14:
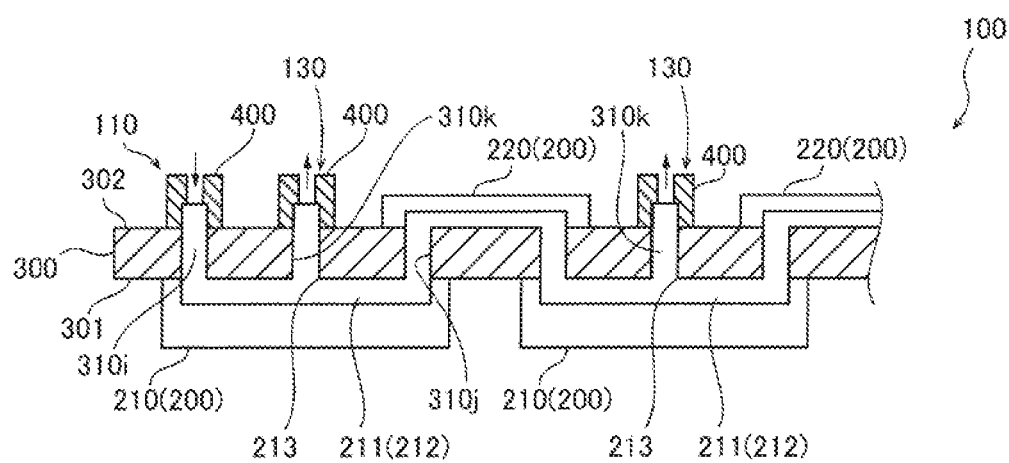
FIG. 14 is a longitudinal sectional view illustrating a third modification of a specimen treatment chip.

FIG. 14 illustrates an example of a specimen treatment chip 100 to which a quality control function is added.

In the example of FIG. 14, a substrate 300 includes a substrate flow channel 310k for recovering liquid from the specimen treatment chip 100 for quality monitoring of the specimen treatment chip 100. The substrate flow channel 310k for recovering liquid is connected to at least one flow channel 211 of a plurality of fluid modules 210 disposed on the substrate 300.

In the example of FIG. 14, the substrate 300 includes a substrate flow channel 310i serving as a liquid injection port 110, a substrate flow channel 310j connecting a flow channel 211 of the fluid module 210 and a second flow channel 221 of the fluid module 220, and a substrate flow channel 310k serving as a port 130 for recovering liquid. The port 130 has a function of recovering a liquid from a specimen treatment chip for quality monitoring of the specimen treatment chip, and is disposed at a position in the middle of the liquid flow channel formed by the plurality of fluid modules 200. The port 130 for recovering a liquid is connected at its first surface 301 side to a liquid recovering connection portion 213 of the flow channel 211.

As a result, it is possible to verify whether the fluid module 210 functions properly by inspecting liquid recovered from the recovering connection portion 213 provided in the flow channel 211 through the substrate flow channel 310k. This makes it possible to easily evaluate performance of each fluid module 210 in the specimen treatment chip 100. As a result, even when a plurality of kinds of fluid module 210 is provided, structure of each fluid module 210 can be easily optimized.

The liquid is recovered from the fluid module 210 through a connector 400 that is connected to at its second surface 302 side to a position corresponding to the substrate flow channel 310k for recovery. When the substrate flow channel 310k is composed of a through hole passing through the substrate 300 in its thickness direction, it is preferable that the substrate flow channel 310k for recovering liquid is provided at a position different from a position at which the fluid module 220 is disposed. This prevents the connector 400 and the fluid module 220 from interfering with each other when the connector 400 is connected to the substrate flow channel 310k.

The recovered liquid is checked whether a desired reaction (e.g., a reaction between a specimen and a reagent) is achieved in the liquid flowing through the fluid module 210, for example. The inspection of the recovered liquid may be performed manually by an operator, or may be automatically performed by a specimen treatment apparatus 500. When it is unnecessary to recover the liquid, such as during normal use of the specimen treatment chip 100, the connector 400 is plugged with a plug 401 (refer to FIG. 12, etc.) or the like.

(Another Configuration Example of Specimen Treatment Chip: Example of Using Both Sides of Substrate)

Figure 15:
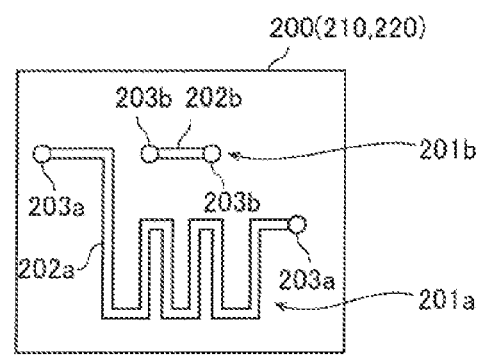
FIG. 15 is a plan view illustrating a fluid module in a fourth modification of a specimen treatment chip.
Figure 16:
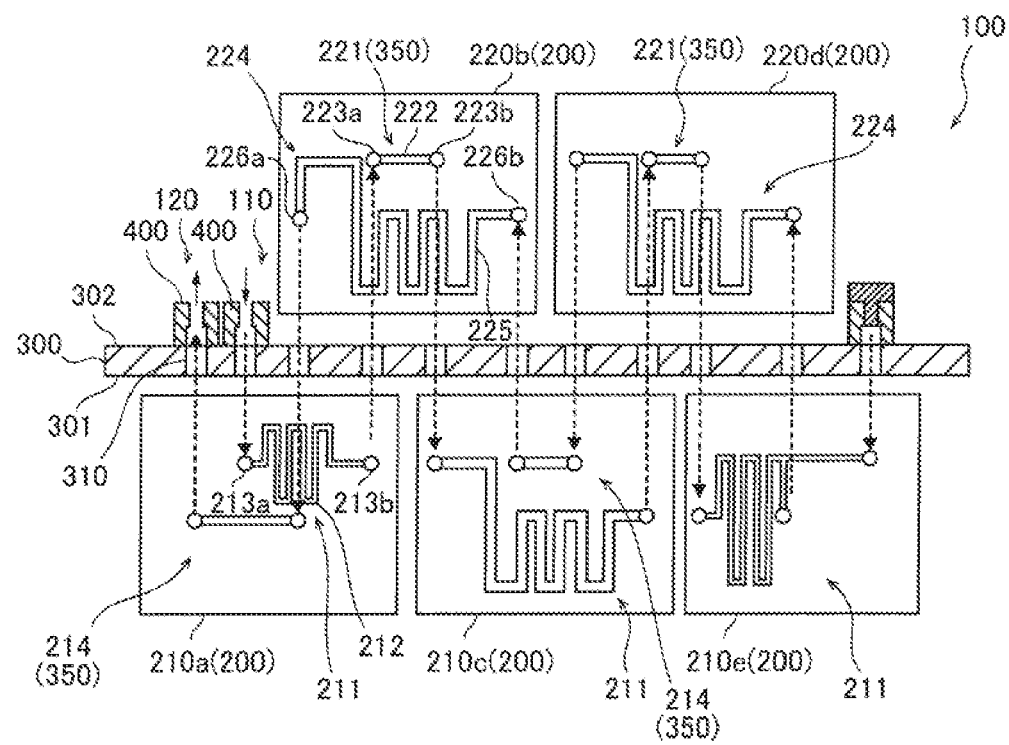
FIG. 16 is a longitudinal sectional view illustrating the fourth modification of a specimen treatment chip.
Figure 17A:
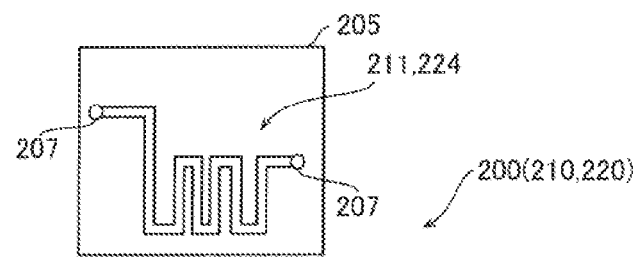
FIGS. 17A through 17C include a plan view (A) of a first layer of a fluid module, a plan view (B) of a second layer, and a longitudinal sectional view (C) of a fluid module in a fifth modification of a specimen treatment chip.
Figure 17B:
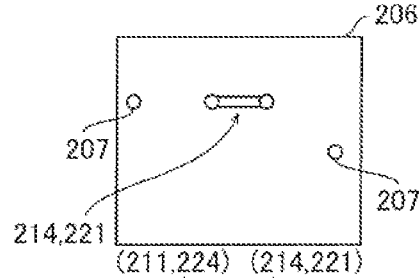
Figure 17C:
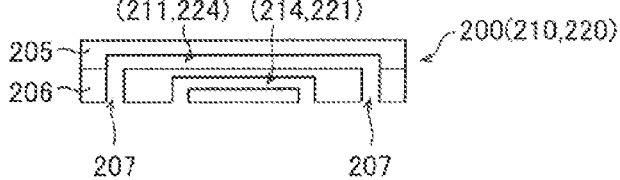

FIGS. 15 to 17 each illustrate a configuration example of a specimen treatment chip 100 in which a fluid module 200 is installed on both sides of a substrate 300.

The fluid module 200 illustrated in FIG. 15 includes a channel 202a for achieving a predetermined function such as a reaction with a specimen or a reagent, a channel 202b for connecting between fluid modules to feed liquid, and connection portions 203a and 203b provided in the channels 202a and 202b, respectively. As described above, the single fluid module 200 may be provided with a flow channel 201a for performing a treatment step, and a connection flow channel 201b for feeding liquid.

When this configuration is applied to a first fluid module 250 and a second fluid module 260, a first flow channel 251 (flow channel 201a) is connected to a second flow channel 261 (flow channel 201a) through at least one of the connection flow channels 201b of the first fluid module 250 and the connection flow channels 201b of the second fluid module 260.

FIG. 16 illustrates a more specific configuration example of the specimen treatment chip 100 composed of fluid modules 200.

In the example of FIG. 16, the specimen treatment chip 100 includes fluid modules 210a, 210c and 210e disposed on a first surface 301 of the substrate 300, and fluid modules 220b and 220d disposed on a second surface 302 thereof.

The fluid modules 210a and 210c each include a flow channel 211 for performing at least one of a plurality of steps, and a flow channel 214 for feeding liquid between adjacent fluid modules 220 on the second surface 302 of the substrate 300. The flow channel 214 is a connection flow channel 350 dedicated to feeding liquid without a function of performing a treatment step.

The fluid modules 220b and 220d each include a flow channel 221 for feeding liquid between adjacent fluid modules 210 on the first surface 301 of the substrate 300, and a flow channel 224 for performing at least one of a plurality of steps. The flow channel 221 is a connection flow channel 350 dedicated to feeding a liquid without a function of performing a treatment step.

In the present example, the flow channel 214 for feeding liquid between the adjacent fluid modules 220 and the flow channel 221 for feeding liquid between the adjacent fluid modules 210 are each configured as a flow channel dedicated to feeding liquid, in which a treatment step is not performed.

Each fluid module is connected to another fluid module through a substrate flow channel 310 provided in the substrate 300. That is, each of the flow channels 211 of the respective adjacent fluid modules 210 on the first surface 301 of the substrate 300 is connected to the flow channel 221 of the fluid module 220 through the substrate flow channel 310. Each of the flow channels 224 of the respective adjacent fluid modules 220 on the second surface 302 of the substrate 300 is connected to the flow channel 214 of the fluid module 210 through the substrate flow channel 310.

With reference to FIG. 16, a flow of liquid, such as a specimen and a reagent, in the specimen treatment chip 100 will be described. In the course of flowing through each of the fluid modules 200 disposed in the specimen treatment chip 100, liquid, such as an object component in a specimen and a reagent, causes a desired reaction.

Liquid, such as a specimen and a reagent, is injected into the fluid module 210a from a connector 400. The liquid injected from the connector 400 flows into a channel 212 of the flow channel 211 through a connection portion 213a. The liquid flowing through the channel 212 is fed from a connection portion 213b to a fluid module 220b.

The liquid fed from the fluid module 210a is fed to the flow channel 221 of the fluid module 220b through a connection portion 223a. The fed liquid flows into a channel 222 for communicating with fluid modules. The liquid flowing into the channel 222 is fed from a connection portion 223b to the fluid module 210c.

In addition, liquid flowing into the flow channel 224 from a connection portion 226b of the fluid module 220b flows through a channel 225, and is fed from a connection portion 226a to the flow channel 214 of the fluid module 210a, for example.

With such a configuration, liquid injected into the specimen treatment chip 100 is fed to the fluid module 210a, the fluid module 220b, the fluid module 210c, the fluid module 220d, the fluid module 210e, the fluid module 220d, the fluid module 210c, the fluid module 220b, and the fluid module 210a, in this order. In a forward path from the fluid module 210a to the fluid module 210e, the injected liquid alternately passes through the flow channel 211 and the flow channel 221 of each fluid module. In a return path toward the fluid module 210a, turning back at the fluid module 210e, the liquid alternately passes through the flow channel 214 and the flow channel 224 of each fluid module.

In the present configuration example, each of the fluid module 210 on a first surface 301 side of the substrate 300 and the fluid module 220 on a second surface 302 side thereof can perform a treatment step included in each of a plurality of steps. This enables the specimen treatment chip 100 to be downsized as compared with a configuration in which the treatment steps are performed only in the fluid module 210.

Some treatment steps need to secure a sufficient flow channel area (or flow channel length) in the fluid module, so that the fluid module is provided at its both ends with respective connection portions in that case. Thus, when the fluid module is configured only with the flow channels (the flow channel 211 and the flow channel 224) for performing the steps, end portions of the respective fluid modules are connected to each other by the substrate flow channel 310, thereby increasing the specimen treatment chip 100 in length as a whole. In contrast, when the flow channels (the flow channel 211 and the flow channel 224) for performing the steps and the connection flow channels (the flow channel 214 and the flow channel 221) for feeding liquid between the fluid modules are configured so as to be connected to each other between the fluid module 210 and the fluid module 220, it is possible to adjust a connection position on the flow channels (the flow channel 214 and the flow channel 221) each for feeding liquid between the fluid modules. That is, as illustrated in FIG. 16, the fluid module 210 and the fluid module 220 can be disposed so as to be increased in their regions overlapping with each other in the thickness direction of the substrate 300. As a result, the specimen treatment chip 100 can be downsized by integrating the fluid module 210 and the fluid module 220.

In FIG. 16, the flow channel 211 for performing a treatment step and the connection flow channel 214 for feeding liquid between the fluid modules are formed in the same layer in the fluid module 210. In addition, the flow channel 224 for performing a treatment step and the connection flow channel 221 for feeding liquid between the fluid modules are formed in the same layer in the fluid module 220. That is, the respective flow channels are formed on the same plane.

<Multilayer Structure>

As illustrated in the example of FIG. 17, a plurality of layers is provided in a fluid module 200 (a fluid module 210, a fluid module 220), and flow channels (a first flow channel and a second flow channel) for performing a treatment process, and a connection flow channel for feeding liquid between fluid modules may be formed in different respective layers in the same fluid module.

That is, in the example of FIG. 17, the fluid module 200 (the fluid module 210 and the fluid module 220) includes a first layer 205 in which the flow channels (the first flow channel and the second flow channel) for performing a step is formed, and a second layer 206 in which the connection flow channel for feeding liquid between fluid modules is formed. In the example of FIG. 17, the flow channels (the flow channel 211 and the flow channel 224) for performing a step is provided in the first layer 205 of the fluid module 200, and the connection flow channels (the flow channel 221 and the flow channel 214) for feeding liquid between fluid modules are provided in the second layer 206 of the fluid module 200. The first layer 205 and the second layer 206 are stacked in the thickness direction of the substrate 300. The connection portion 207 of the first layer 205 is formed so as to pass through the second layer 206. In this case, the first layer 205 and the second layer 206 are separately formed, and the respective layers are joined to each other to form the fluid module 200 with a multilayer structure, for example.

With such a configuration, only the flow channel for performing a step can be formed in the first layer 205, so that a flow channel area (or a flow channel length) of the flow channels (the flow channel 211 and the flow channel 224) for performing a step can be more easily secured as compared with the case where each of the flow channels is formed in the same plane.

<Modification of Channel Shape>

Figure 18:
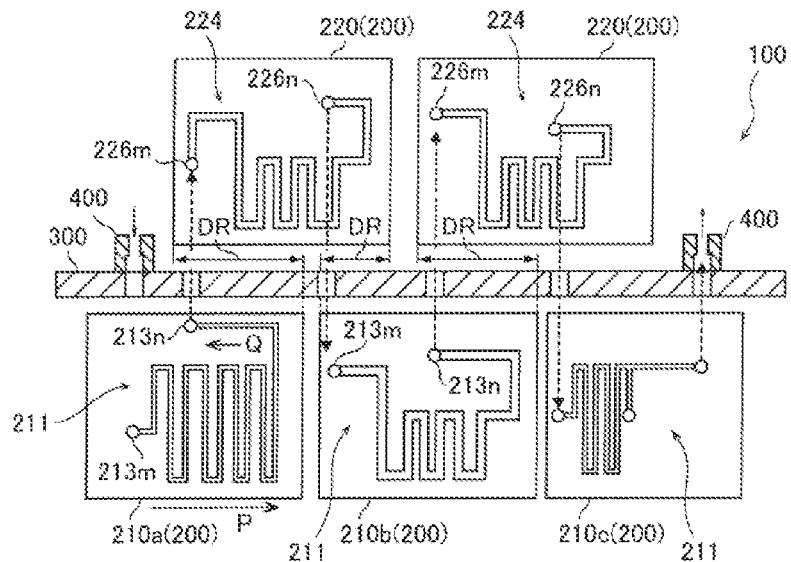
FIG. 18 is a longitudinal sectional view illustrating a sixth modification of a specimen treatment chip.

FIG. 18 illustrates another configuration example of the specimen treatment chip 100 that performs both-side treatment.

In the example of FIG. 18, each fluid module 200 has no connection flow channel (the flow channel 214 and the flow channel 221 in FIG. 16) for feeding liquid between fluid modules. Each fluid module 200 includes only the flow channel (the flow channel 211 or the flow channel 224) for performing a step.

The fluid module 210 includes a flow channel 211 for performing at least one of a plurality of steps. The fluid module 220 includes a flow channel 224 for performing at least one of a plurality of steps. Thus, the configuration example of FIG. 18 also enables the specimen treatment chip 100 to be downsized as compared with a configuration in which a treatment step is performed only in the fluid module 210.

Meanwhile, in the example of FIG. 18, the fluid module 210 includes no flow channel (the flow channel 214, refer to FIG. 16) for feeding liquid between fluid modules. The fluid module 220 includes no flow channel (the flow channel 221, refer to FIG. 16) for feeding liquid between fluid modules.

In the example of FIG. 18, at least one of the flow channel 211 of the fluid module 210 and the flow channel 224 of the fluid module 220 has a shape routed in a Q direction opposite to a P direction from one connection portion 213m (226m) of the flow channel toward the other connection portion 213n (226n).

That is, the other connection portion 213n (226n) serving as an outlet of each fluid module is provided at a position at which the channel 212 (225) is routed in the Q direction opposite to the P direction. As a result, it is possible to increase a region DR where fluid modules (e.g., the fluid module 210a and the fluid module 220b) disposed on mutually opposite surfaces overlapping with each other while a flow channel area (or a flow channel length) of the channel 212 (225) of each fluid module is secured. That is, even when only the flow channel for performing a treatment step is provided in each fluid module, an area for mounting each fluid module on the substrate 300 can be reduced. It is possible to mount more fluid modules on the substrate 300 by reducing a mounting area of the fluid module.

[Configuration Example of Specimen Treatment Apparatus]

Figure 19:
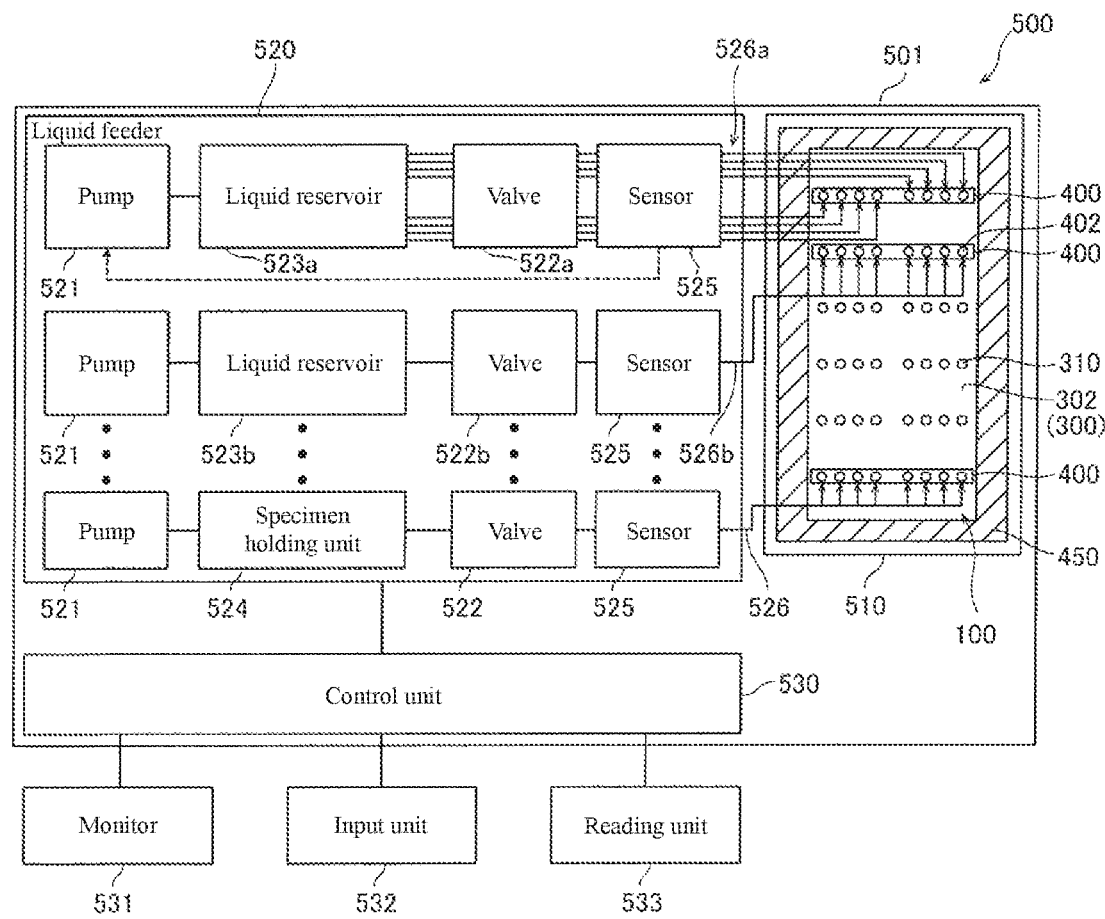
FIG. 19 is a block diagram illustrating a configuration example of a specimen treatment apparatus.

FIG. 19 illustrates a configuration example of the specimen treatment apparatus 500. The specimen treatment apparatus 500 has functions such as liquid injection into the specimen treatment chip 100, liquid recovery from the specimen treatment chip 100, detection of a reaction occurring in the specimen treatment chip 100, and the like.

In the configuration example of FIG. 19, a liquid feeder 520 includes a pump 521 that controls pressure for driving liquid, and a valve 522 that opens and closes a supply path of pressure to the liquid. The liquid feeder 520 further includes a liquid reservoir 523 for containing liquid to be injected into the specimen treatment chip 100, and a specimen holding unit 524. In addition, the liquid feeder 520 includes a flow rate sensor 525 for measuring a flow rate of liquid flowing in the specimen treatment chip.

The pump 521, the liquid reservoir 523, the valve 522, and the flow rate sensor 525 are connected in order by a liquid feeding pipe 526. The specimen treatment apparatus 500 injects liquid into the specimen treatment chip 100 and recovers liquid from the specimen treatment chip 100 through the connector 400 by using the pump 521, the liquid reservoir 523, and the valve 522. In the example of FIG. 19, one set of the pump 521, the liquid reservoir 523, and the valve 522 correspond to a predetermined connector 400. For example, the specimen treatment apparatus 500 has the same number of sets of the pump 521, the liquid reservoir 523, and the valve 522 as the number of the connectors 400 connectable to the specimen treatment chip 100 (or the number of rows of ports). However, at least one liquid reservoir 523 is configured as the specimen holding unit 524 that holds a specimen.

For example, a plurality of liquid reservoirs 523 and a plurality of valves 522 may be connected to one pump 521. The valve 522 switches a route to enable a plurality of kinds of liquid and reagent to be supplied to the specimen treatment chip 100 by the common pump 521.

The pump 521 applies pressure to the liquid reservoir 523 and the specimen holding unit 524. When the pump 521 applies positive pressure to the liquid reservoir 523, liquid is fed from the liquid reservoir 523. When the pump 521 applies negative pressure to the liquid reservoir 523, liquid flows into the liquid reservoir 523 from the specimen treatment chip 100. The pump 521 is a pressure pump that supplies air pressure, for example. Besides this, a syringe pump, a diaphragm pump, or the like can be used as the pump 521.

The control unit 530 can individually control operation of each pump 521. The control unit 530 individually controls each pump 521 to enable control of feeding liquid, suitable for a combination of the fluid modules 200 mounted on the specimen treatment chip 100.

In the configuration of FIG. 19, the flow rate sensor 525 detects a flow rate (e.g., a unit is μL/min) of liquid flowing through the liquid feeding pipe 526. The flow rate sensor 525 feeds back a detection result of the flow rate to the pump 521. The pump 521 controls pressure in response to feedback from the flow rate sensor 525.

The flow rate sensor 525 may transmit feedback to the control unit 530. The control unit 530 controls pressure of the liquid feeder 520 for feeding liquid, in accordance with a flow rate measured by the flow rate sensor 525. This makes it possible to accurately control supply pressure when a specimen containing an object component or a reagent is supplied to the specimen treatment chip 100.

The connector 400 is provided on a lid 621, described later, of the specimen treatment apparatus 500. The connector 400 is connected to the liquid feeding pipe 526. In the connector 400, liquid such as a specimen is fed to the specimen treatment chip 100 through the connector 400. In addition, liquid is recovered from the specimen treatment chip 100 through the connector 400.

The specimen treatment chip 100 is set in the installation unit 510. For example, the specimen treatment chip 100 is held such that the second surface 302 of the substrate 300 faces upward, and the substrate flow channel 310 is connected at its end portion on a second surface 302 side to the connector 400.

The specimen treatment chip 100 may include a fixture 450 for installation in the installation unit 510. The fixture 450 may be detachable from the installation unit 510, or may be fixed to the installation unit 510.

In addition, the specimen treatment apparatus 500 can include a monitor 531, an input unit 532, a reading unit 533, and the like. The control unit 530 causes the monitor 531 to display a predetermined display screen corresponding to operation of the specimen treatment apparatus 500. The specimen treatment apparatus 500 may be connected to an external computer (not illustrated) to display a screen in a monitor of the computer. The input unit 532 is composed of a keyboard and the like, for example, and has a function of receiving information input. The reading unit 533 is composed of a code reader for a bar code, a two-dimensional code, or the like, and a tag reader for an RFID tag, or the like, and has a function of reading out information given to the specimen treatment chip 100. The reading unit 533 can also read out information such as a specimen container (not illustrated) for containing a specimen containing an object component.

(Configuration Example of Valve)

Figure 20:
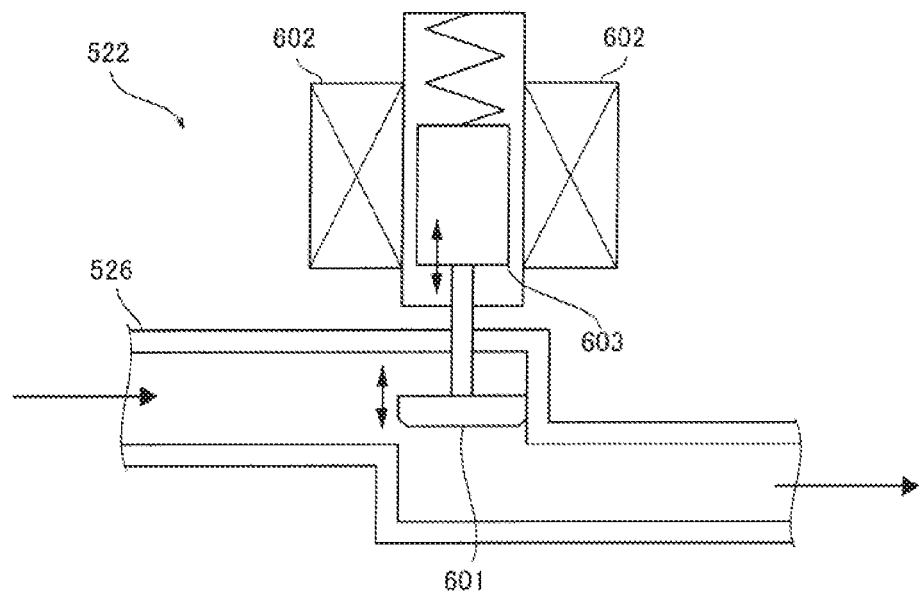
FIG. 20 is a sectional view illustrating a configuration example of a valve.

FIG. 20 illustrates a configuration example of the valve 522. The valve 522 controls an outflow of liquid from the liquid reservoir 523 and an inflow of the liquid into the liquid reservoir 523 by using a valve 601.

The valve 522 is an electromagnetic valve, for example. The valve 522 includes a coil 602. The coil 602 moves a plunger 603 between an open position and a closed position by using a magnetic field generated by electric current flowing through the coil 602. The control unit 530 controls electric current flowing through the coil 602. The valve 601 opens and closes the liquid feeding pipe 526 in accordance with a movement of the plunger 603.

As in the example of FIG. 19, a plurality of valves 522 is disposed in the specimen treatment apparatus 500. The control unit 530 is capable of individually controlling opening and closing of each valve 522.

The control unit 530 controls opening and closing of each valve 522 of the liquid feeder 520 on the basis of a combination of the fluid modules 200. This enables control of feeding liquid, suitable for a combination of the fluid modules 200 mounted on the specimen treatment chip 100, through the valve 522. Then, a plurality of kinds of liquid and reagent can be easily supplied to the specimen treatment chip 100 at a desired timing by simply controlling opening and closing timing of each valve 522.

The control unit 530 controls timing of opening of the valve 522 on the basis of an elapsed time from an injection of liquid into the specimen treatment chip 100, or the amount of an injection of the liquid into the specimen treatment chip 100, for example. This makes it possible to accurately control the amount of supply of liquid into the specimen treatment chip 100 on the basis of an elapsed time under a constant flow rate and the injection amount of the liquid. As a result, quantitative supply of various kinds of liquid suitable for a combination of the fluid modules 200 mounted on the specimen treatment chip 100 becomes possible. The control unit 530 may determine timing of opening of each valve 522 on the basis of a result of image analysis of a flow of the liquid in the specimen treatment chip 100, for example.

(Configuration Example of Liquid Feeding Pipe)

For example, the specimen treatment apparatus 500 includes the number of liquid feeding pipes 526*a* corresponding to the number of holes 402 of the connector 400, as illustrated between a liquid reservoir 523*a* and a valve 522*a* as well as between the valve 522*a* and the connector 400. In the example of FIG. 19, eight liquid feeding pipes 526*a* are disposed between the liquid reservoir 523*a* and the valve 522*a* as well as between the valve 522*a* and the connector 400. In this case, the valve 522*a* is disposed for each of the eight liquid feeding pipes 526*a*.

For example, the specimen treatment apparatus 500 may include a liquid feeding pipe 526*b* branching to the holes 402 of the connector 400, as illustrated between the liquid reservoir 523*b* and the valve 522*b* as well as between the valve 522*b* and the connector 400. In the example of FIG. 19, one liquid feeding pipe 526*b* is disposed between the liquid reservoir 523*b* and the valve 522*b*, and the liquid feeding pipe 526*b* branches to each of the holes 402 of the connector 400.

(Configuration Example of Liquid Reservoir and Specimen Holding Unit)

Figure 21:
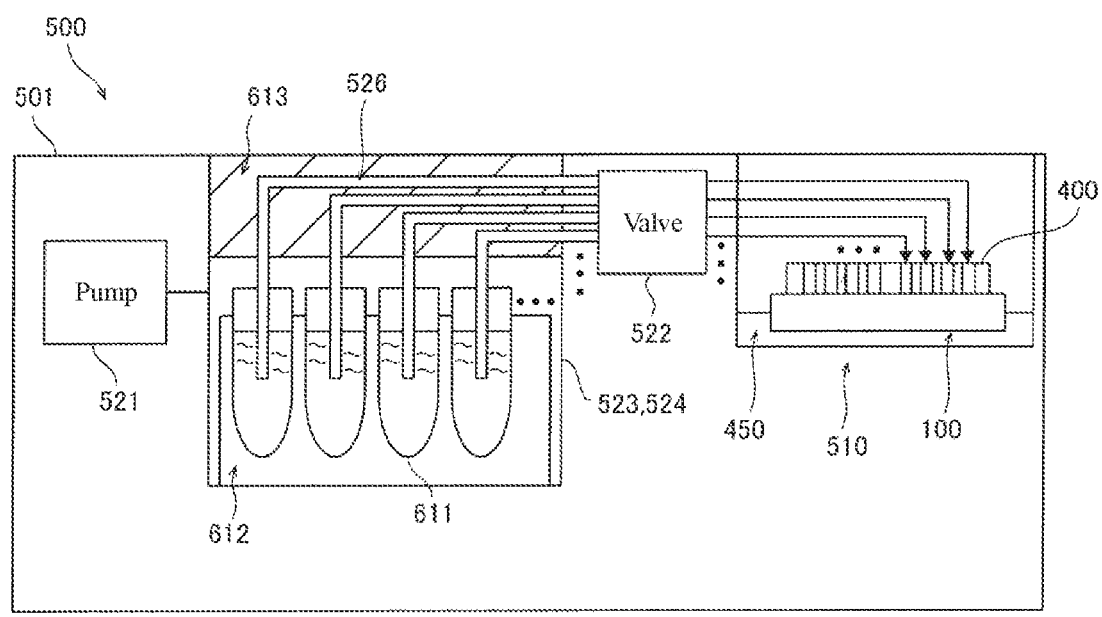
FIG. 21 is a longitudinal sectional view illustrating a configuration example of a liquid reservoir.

FIG. 21 illustrates a configuration example of the liquid reservoir 523 and the specimen holding unit 524.

Liquid containers 611 each such as for a specimen and a reagent are disposed in a container installation unit 612 of the liquid reservoir 523 or the specimen holding unit 524. As illustrated in FIG. 21, a plurality of the container installation units 612 may be disposed, or the single container installation unit 612 may be disposed.

The liquid reservoir 523 and the specimen holding unit 524 are hermetically sealed by a lid 613. The lid 613 is provided with the liquid feeding pipes 526. When the liquid reservoir 523 is sealed with the lid 613, the liquid feeding pipes 526 are inserted into the corresponding containers 611 for a specimen or a reagent. The liquid feeding pipes 526 provided in the lid 613 are connected to the specimen treatment chip 100 through the valve 522. The pump 521 adjusts pressure in the liquid reservoir 523 sealed with the lid 613. When the pressure in the liquid reservoir 523 is increased to open the valve 522, liquid in each of the containers 611 is supplied to a specimen treatment chip 100 side.

A kind of liquid to be contained in each liquid reservoir 523 varies depending on a combination of the fluid modules 200 and an assay method. The control unit 530 determines a liquid reservoir 523 in which a liquid is to be contained and a kind of liquid to be contained in the liquid reservoir 523, on the basis of the combination of the fluid modules 200, for example, and notifies the determined liquid reservoir 523 and kind of liquid to be contained. For example, the notification can be achieved by a method such as for displaying the liquid reservoir 523 in which liquid is to be contained, and the kind of liquid to be contained in the reservoir 523, in the monitor 531 of the specimen treatment apparatus 500 or a monitor (not illustrated) of a computer connected to the specimen treatment apparatus 500. This enables erroneous operation by a user to be prevented.

Figure 22:
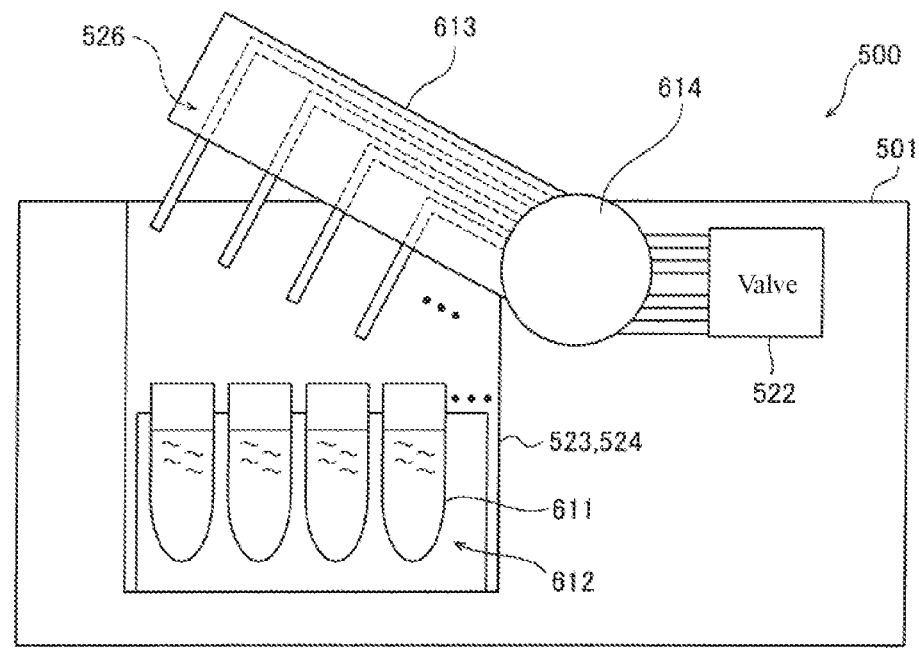
FIG. 22 is a longitudinal sectional view illustrating a first configuration example of a lid for a liquid reservoir.
Figure 23:
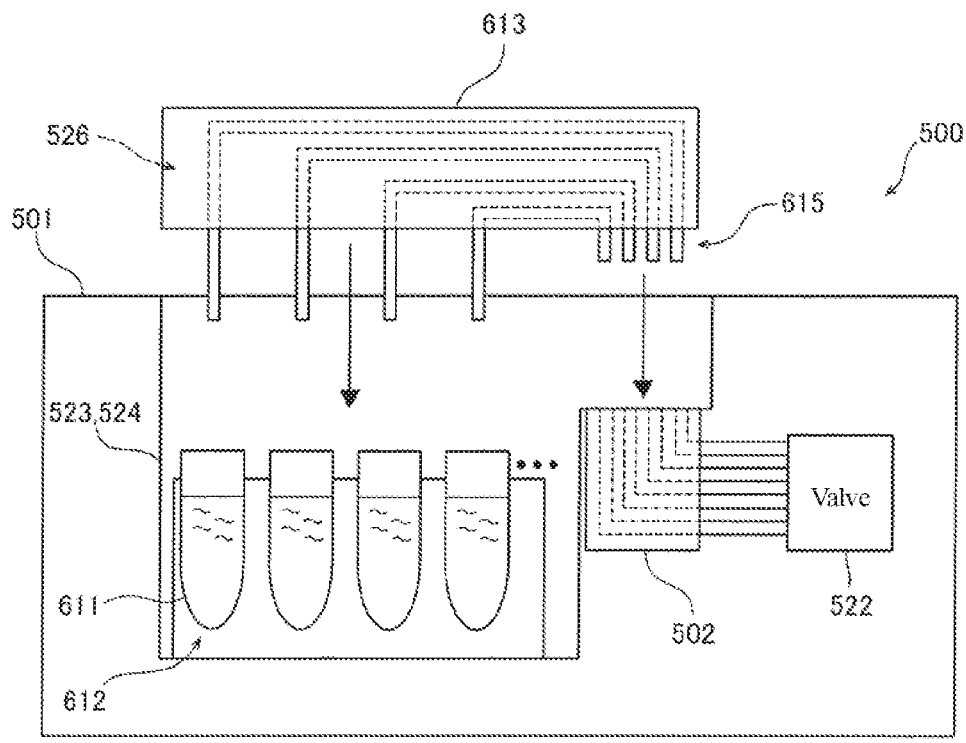
FIG. 23 is a longitudinal sectional view illustrating a second configuration example of a lid for a liquid reservoir.

FIGS. 22 and 23 each illustrate a configuration example of the lid 613 for a liquid reservoir.

The lid 613 illustrated in FIG. 22 is connected to a specimen treatment apparatus main body 501 with a hinge 614. The lid 613 is moved by rotation of the hinge 614 to be able to open and close the inside of the liquid reservoir 523 or the specimen holding unit 524. At least some of the liquid feeding pipes 526 provided in the lid 613 are each composed of a rubber tube or the like to be deformable in response to opening and closing of the lid 613.

The lid 613 illustrated in FIG. 23 is detachable from the specimen treatment apparatus main body 501. When the lid 613 is attached to the specimen treatment apparatus main body 501, the connector 615 of the lid 613 and the connector 502 on a specimen treatment apparatus 500 side are connected to each other, and then the liquid feeding pipes 526 between the lid 613 and the valve 522 are connected.

The lid 613 is detachable from the specimen treatment apparatus 500, maintenance of the liquid feeding pipe 526 can be performed only by replacing the lid 613 when the liquid feeding pipe 526 is deteriorated due to contamination or the like.

(Configuration Example of Lid of Installation Unit)

Figure 24:
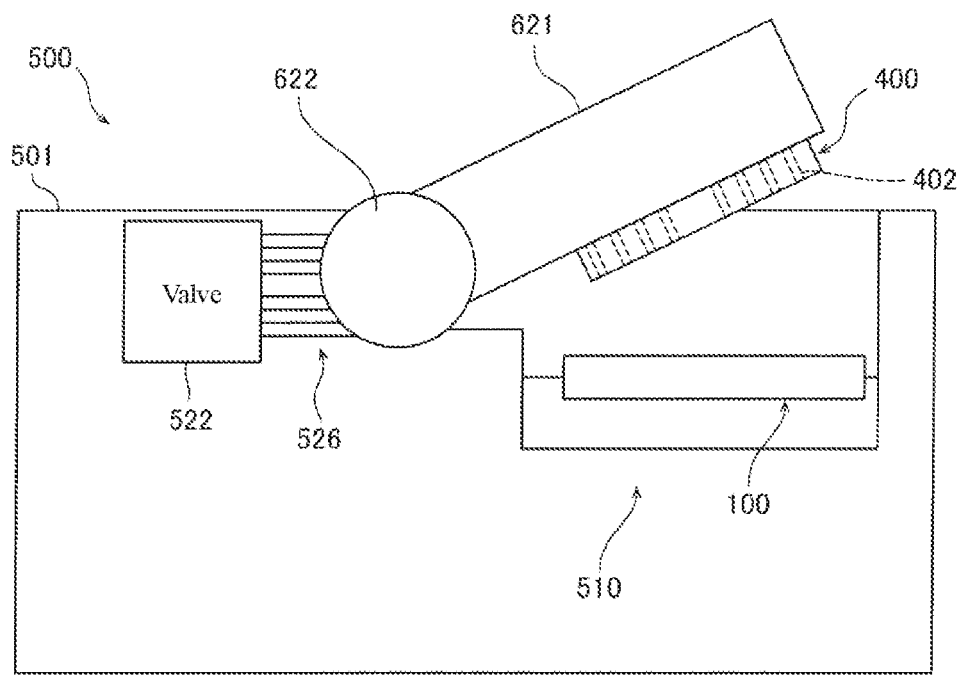
FIG. 24 is a longitudinal sectional view illustrating a first configuration example of a lid of an installation unit.
Figure 25:
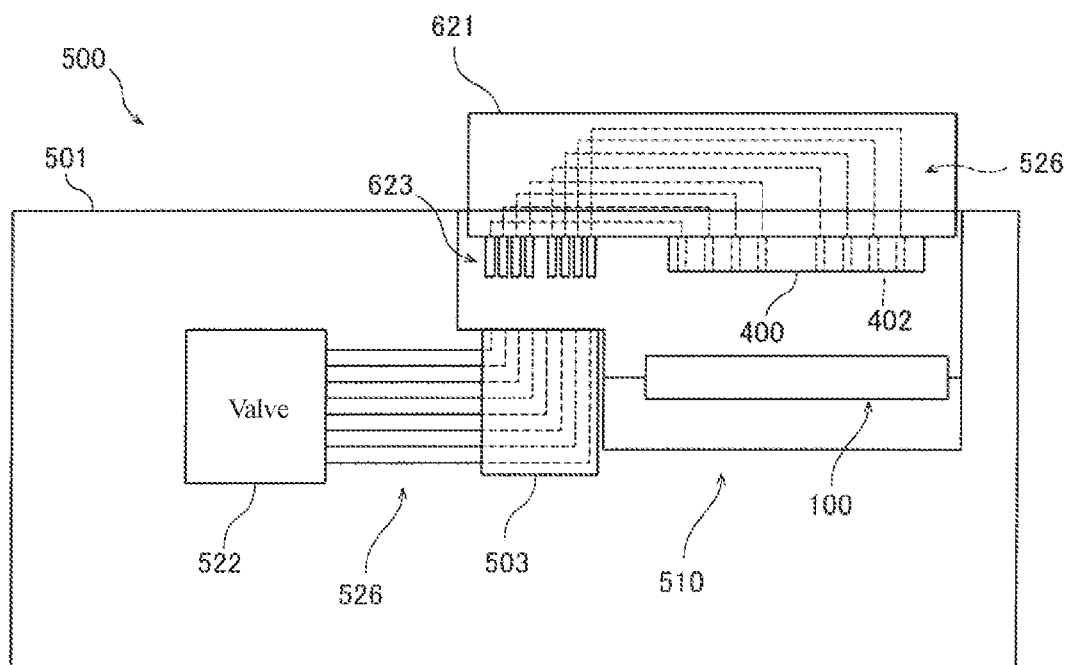
FIG. 25 is a longitudinal sectional view illustrating a second configuration example of a lid of an installation unit.

The installation unit 510 may be provided with a lid 621 corresponding to the installation unit 510. FIGS. 24 and 25 each illustrate a configuration example of the lid 621 of the installation unit 510. The lid 621 is provided so as to cover the specimen treatment chip 100 set in the installation unit 510.

The lid 621 illustrated in FIG. 24 is connected to a specimen treatment apparatus main body 501 with a hinge 622. The lid 621 is opened and closed by rotation of the hinge 622. At least some of the liquid feeding pipes 526 provided in the lid 621 are each composed of a rubber tube or the like to be deformable in response to opening and closing of the lid 621.

The lid 621 may include a connector 400 for injecting liquid into a port (110 or 120) provided at a predetermined position on the specimen treatment chip 100. The port is a substrate flow channel 310 serving as a port 110 for injecting a liquid or a reagent, or a substrate flow channel 310 serving as a port 120 for recovering a liquid, for example. The tip of each of the liquid feeding pipes 526 extending from the valve 522 is connected to the hole 402 of the connector 400. Liquid is fed between the specimen treatment chip 100 and the liquid feeding pipe 526 through the connector 400. This makes it possible to connect the specimen treatment chip 100 installed in the installation unit 510 and the connector 400 to each other only by closing the lid 621 of the installation unit 510.

The lid 621 illustrated in FIG. 25 is detachable from the specimen treatment apparatus main body 501.

When the lid 621 is attached to the specimen treatment apparatus main body 501, the connector 623 of the lid 621 and the connector 503 of the specimen treatment apparatus 500 are connected to each other, and then the liquid feeding pipes 526 between the lid 621 and the valve 522 are connected. In addition, the connector 400 of the lid 621 is connected to the port of the specimen treatment chip 100. Liquid is fed between the specimen treatment chip 100 and the liquid feeding pipe 526 through the connectors 503, 623, and 400.

When the lid 621 is configured to be detachable from the specimen treatment apparatus main body 501 as described above, maintenance of the liquid feeding pipe 526 can be performed only by replacing the lid 621 when the liquid feeding pipe 526 is deteriorated due to contamination or the like.

(Configuration Example of Connector)

Figure 26:
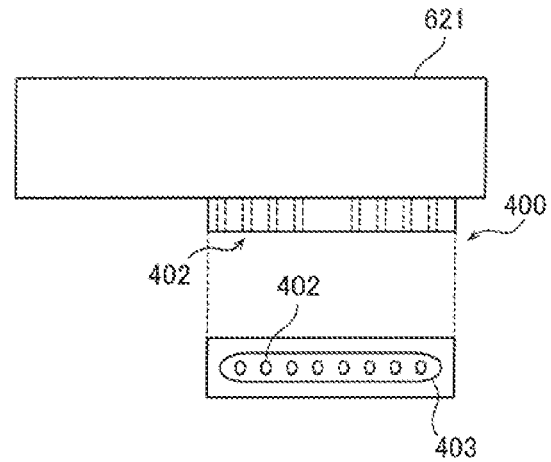
FIG. 26 is a longitudinal sectional view illustrating a first configuration example of a connector.
Figure 27:
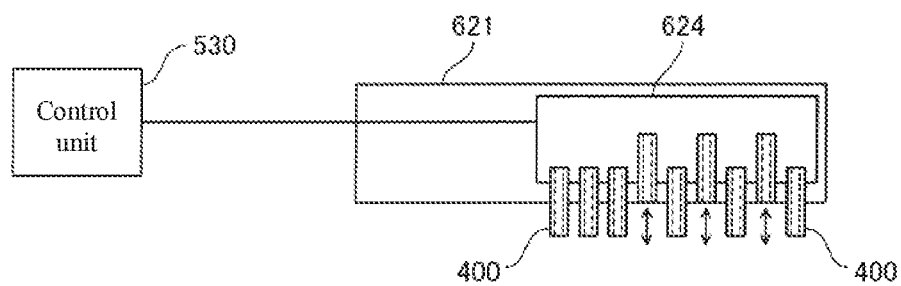
FIG. 27 is a longitudinal sectional view illustrating a second configuration example of a connector.
Figure 28:
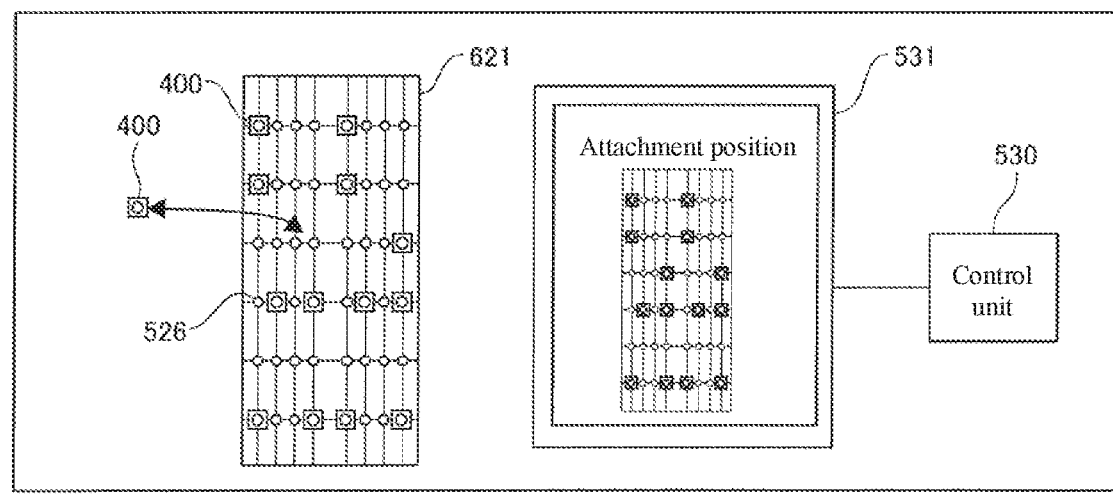
FIG. 28 is a schematic diagram illustrating a third configuration example of a connector.

FIGS. 26 to 28 each illustrate a configuration example of the connector 400.

The connector 400 is provided on the lid 621. The connector 400 has the hole 402 for connecting to the substrate flow channel 310 of the substrate 300. The connector 400 is installed at a position corresponding to the substrate flow channel 310 of the substrate 300. The connector 400 may be provided only at a position corresponding to an arbitrary substrate flow channel 310.

Liquid, such as a specimen and a reagent, is injected into the specimen treatment chip 100 from the liquid feeding pipe 526 through the hole 402. The liquid flowing through the specimen treatment chip 100 is recovered from the specimen treatment chip 100 through the hole 402. An arbitrary substrate flow channel 310 can be sealed by inserting the plug 401 (refer to FIG. 12, etc.) into the corresponding hole 402.

The connector 400 is provided with a sealing material such as a gasket 403 on its contact surface with the specimen treatment chip 100. The gasket 403 prevents liquid leakage and foreign matter contamination between the ports 110 and 120, and the holes 402.

The substrate flow channel 310 through which liquid is injected or recovered by the connector 400 varies according to a combination of the fluid modules 200 disposed in the specimen treatment chip 100. Thus, the connector 400 does not need to be disposed in all the substrate flow channels 310.

For example, the lid 621 may be capable of accommodating the connector 400 inside the lid 621. In the example of FIG. 27, the lid 621 includes a plurality of connectors 400, and a driving unit 624 for moving each of the plurality of connectors 400 inward and outward of the lid 621. Then, the control unit 530 determines the corresponding one of the connectors 400 to be accommodated inside the lid 621 on the basis of a combination of the fluid modules 200, and instructs the lid 621 to accommodate the determined connector 400. When the connector 400 specified by the control unit 530 protrudes to the outside of the lid 621, the driving unit 624 moves the connector 400 backward to the inside of the lid 621.

According to the present configuration, only the connector 400 necessary for use of the specimen treatment chip 100 can be automatically connected to the specimen treatment chip 100. In addition, it is possible to prevent the connector 400 from being installed in a wrong position.

The connector 400 may be configured to be detachable from the lid 621. In the example of FIG. 28 illustrating a lower surface of the lid 621, the lid 621 is configured such that a plurality of connectors 400 is detachable. A user of the specimen treatment apparatus 500 can mount a necessary connector 400 at a predetermined position of the lid 621 according to a combination of the fluid modules 200. In this case, the control unit 530 notifies a position where the corresponding one of the connectors 400 is to be mounted on the basis of a combination of the fluid modules 200, for example. The notification can be achieved by using a method such as for displaying a position where the connector 400 is to be mounted in the monitor 531 of the specimen treatment apparatus 500, or in a monitor (not illustrated) of a computer connected to the specimen treatment apparatus 500. This enables only the connector 400 necessary for use of the specimen treatment chip 100 to be connected to the specimen treatment chip 100 with a simple configuration, so that wrong attachment of the connector 400 by a user can be prevented.

<Configuration Example of Fixture>

Figure 29:
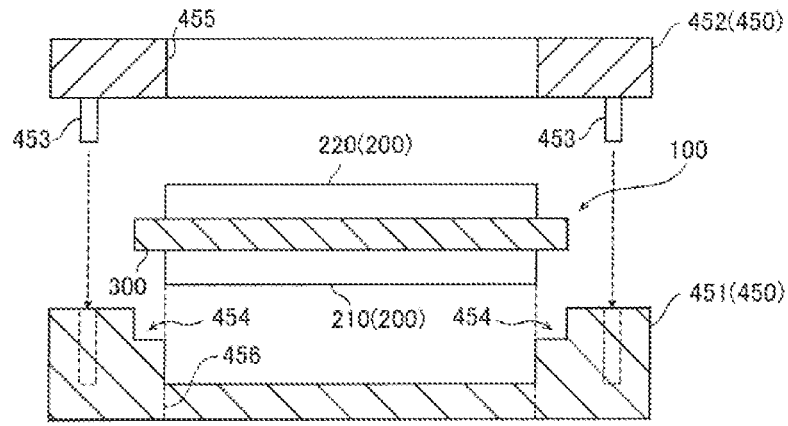
FIG. 29 is an exploded view illustrating a configuration example of a fixture.
Figure 30:
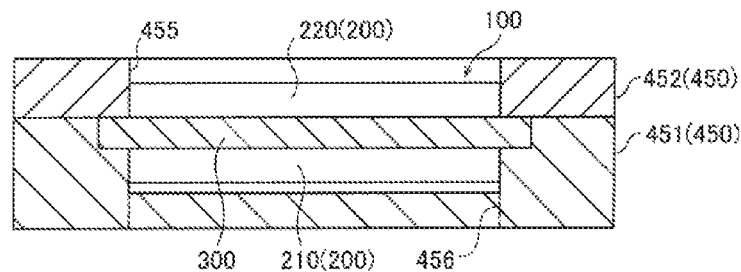
FIG. 30 illustrates a fixture in a state where a specimen treatment chip is fixed.
Figure 31A:
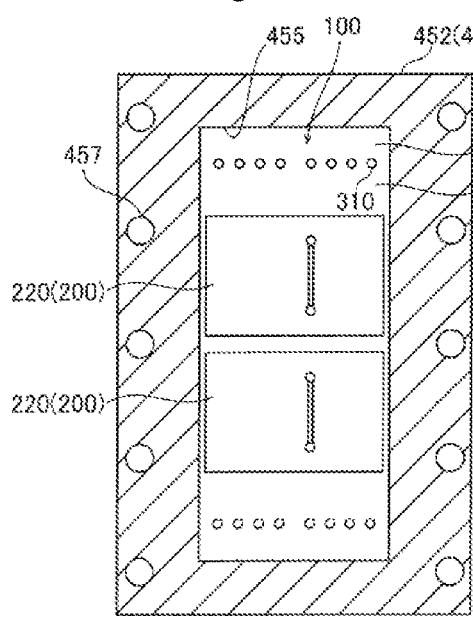
FIGS. 31A and 31B include a top view (A) and a bottom view (B) of the fixture in FIG. 30.
Figure 31B:
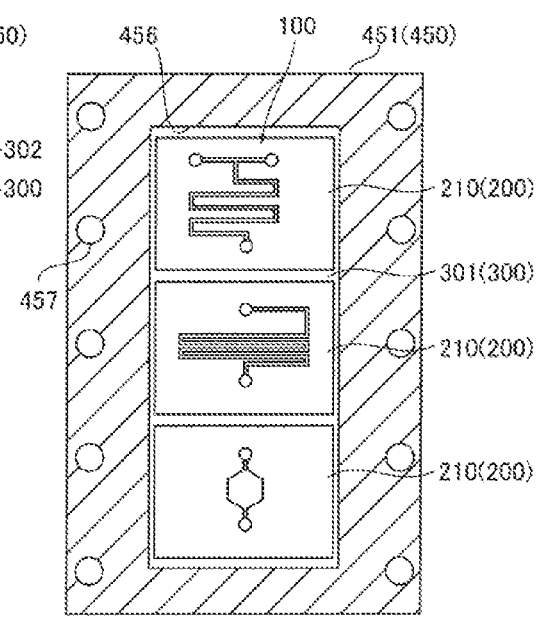

FIGS. 29 to 31 each illustrate an example of the fixture 450 used for installing the specimen treatment chip 100 in the specimen treatment apparatus 500.

As illustrated in FIG. 29, the specimen treatment chip 100 is fixed with fixtures 451 and 452, for example. The fixtures 451 and 452 are fixed with fitting members 453. For example, the specimen treatment chip 100 is horizontally positioned by a positioning portion 454 formed in the fixture 451 on a lower side. In the example of FIG. 29, the positioning portion 454 is composed of a stepped portion that is recessed. The positioning portion 454 determines a relative position between the specimen treatment chip 100 and the fixtures 451 and 452.

FIG. 30 is a side view of the specimen treatment chip 100 in a state of being fixed with the fixtures 451 and 452. The specimen treatment chip 100 composed of a substrate 300 provided on its both surfaces with respective bonded fluid modules 200 is fixed with the fixtures as illustrated in FIG. 30.

As illustrated in FIG. 31 (A), the fixture 452 has an opening 455 formed of a through hole at a position corresponding to the substrate 300. The connector 400 and the like of the specimen treatment apparatus 500 can be connected to the substrate 300 from above through the opening 455. In addition, as illustrated in FIG. 31 (B), the fixture 451 has an opening portion 456 formed of a through hole at a position corresponding to the substrate 300 and the fluid module 200, so that the substrate 300 and the fluid module 200 can be connected from below through the opening portion 456.

When the specimen treatment chip 100 held by the fixtures 451 and 452 is installed in the installation unit 510, or when the specimen treatment chip 100 is set to the fixture 451 fixed to the installation unit 510 and the fixture 452 is attached to the fixture 451, the specimen treatment chip 100 is set in the installation unit 510. The fixture 452 may be fixed to the lid 621 of the installation unit 510 so that the fixture 452 is attached to the fixture 451 at the same time when the lid 621 is installed.

As illustrated in FIG. 31, the fixtures 451 and 452 each may have attachment holes 457 for disposing various treatment units provided in the specimen treatment apparatus 500. In the example of FIG. 31, a plurality of the attachment holes 457 is provided outside the opening 455 along a long side of the fixture 452 (451).

When the fixture 450 as described above is set in the installation unit 510, or is preliminarily provided in the installation unit 510, the installation unit 510 is configured such that a treatment unit can be installed according to a placement position of the corresponding fluid module 200 in the specimen treatment chip 100. This makes it possible to replace a treatment unit with the corresponding treatment unit according to a combination of the fluid modules 200 provided in the specimen treatment chip 100. As a result, there is obtained the specimen treatment apparatus 500 capable of reconfiguring its use and function according to various specimen treatment chips 100 each with a different combination of the fluid modules 200.

(Installation Example of Various Treatment Units)

FIG. 32 illustrates an installation example of treatment units used for various treatment steps of the specimen treatment apparatus 500.

As illustrated in FIGS. 32(A) to 32(C), a heater unit (heater 541) for heating liquid in the fluid module 200, a magnet unit 542 for applying a magnetic force to liquid in the fluid module 200, a cooling unit 543 for cooling liquid in the fluid module 200, a detection unit (detector 544) for detecting an object component in the specimen treatment chip 100, a camera unit 545 for photographing a flow of liquid in the fluid module 200, and the like are attached to the fixture 451 or 452 using the attachment holes 457, for example. The connector 400 may be attached to the fixture 451 or 452. The unit may be a complex type unit having a plurality of functions among the above functions. For example, a unit having a function of heating liquid and a function of applying magnetic force to liquid may be used.

When these units and the specimen treatment chip 100 are simply attached to the fixtures 451 and 452, relative positioning between each of the units and the specimen treatment chip 100 can be easily performed with the fixture 451 (452).

For example, a plurality of the attachment holes 457 is provided at a predetermined pitch W. Thus, even when different specimen treatment chips 100 each with a different combination of fluid modules 200 are used, a combination of units and a position of each of the units can be freely changed in units of the pitch W according to a combination of the fluid modules 200. The pitch W may be equal to the pitch H of the substrate flow channel 310 of the substrate 300, or may be an integral multiple of the pitch H, for example. In this case, it is possible to easily allow a position of each of the fluid modules 200 and a position of the corresponding one of the units to coincide with each other.

<Heater Unit>

FIG. 33 illustrates a placement example of the heater 541 in the specimen treatment apparatus 500.

The heater 541 adjusts temperature of the specimen treatment chip 100. For example, the heater 541 heats the specimen treatment chip 100 to amplify DNA in the fluid module 200 by PCR.

The heater 541 is provided in the installation unit 510. For example, the heater 541 is attached to the fixture 451 on a lower surface side of the specimen treatment chip 100. The heater 541 adjusts temperature of the specimen treatment chip 100 from the lower surface side of the specimen treatment chip 100 installed in the installation unit 510. The heater 541 is disposed at a position corresponding to the fluid module 200 to be controlled for temperature.

The heater 541 may be movable. The control unit 530 of the specimen treatment apparatus 500 causes the heater 541 to be moved such that the heater 541 is disposed at a position corresponding to the fluid module 200 to be controlled for temperature among the fluid modules 200 mounted on the specimen treatment chip 100.

<Detection Unit>

Figure 34A:
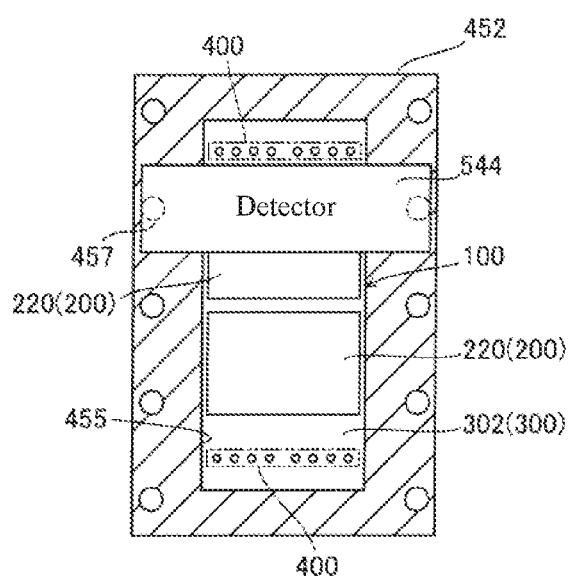
FIGS. 34A and 34B include a top view (A) illustrating a placement example of a detection unit in a fixture and a schematic sectional view (B) illustrating a placement example of a detection unit in an installation unit.
Figure 34B:
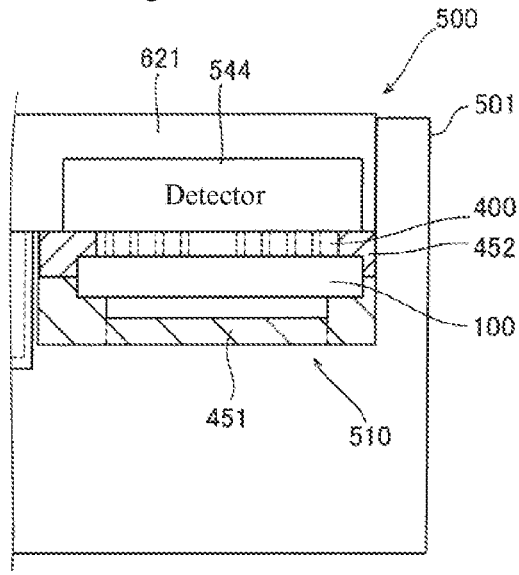

FIG. 34 illustrates a configuration example of the detector 544 of the specimen treatment apparatus 500.

The detector 544 detects fluorescence of a marking substance binding to an object component, for example. The detector 544 is a photomultiplier, for example. The detector 544 is attached to the fixture 452 on an upper surface side of the specimen treatment chip 100, for example. The detector 544 may be provided in the lid 621. The detector 544 detects fluorescence from between the connectors 400 connected to the specimen treatment chip 100. The detector 544 may be provided in the fixture 451 on the lower surface side of the specimen treatment chip 100, or in the specimen treatment apparatus main body 501. In this case, the detector 544 detects fluorescence from the lower surface side of the specimen treatment chip 100.

<Magnet Unit>

Figure 35A:
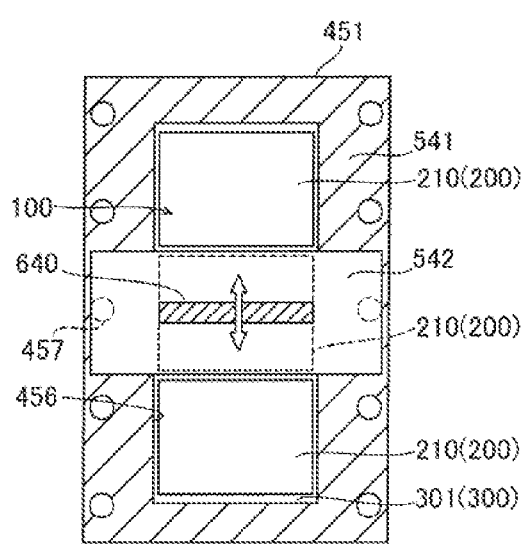
FIGS. 35A and 35B include a bottom view (A) illustrating a placement example of a magnet unit in a fixture and a schematic sectional view (B) illustrating a placement example of a detection unit in an installation unit.
Figure 35B:
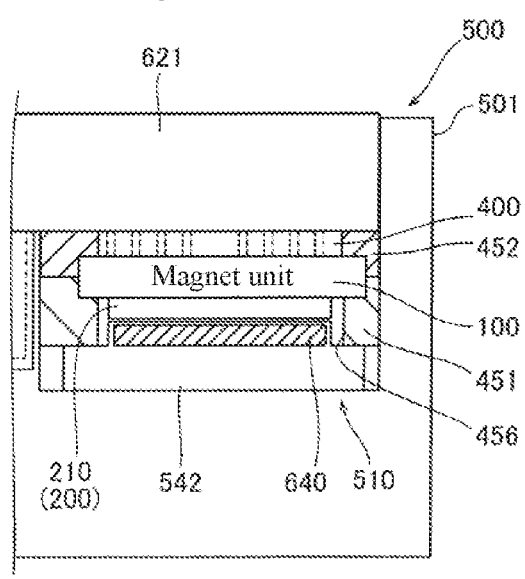

FIG. 35 illustrates a configuration example of the magnet unit 542 used for controlling magnetic particles contained in liquid in the specimen treatment chip 100.

The magnet unit 542 is attached to the fixture 451 on the lower surface side of the specimen treatment chip 100, for example. The magnet unit 542 may be provided in the specimen treatment apparatus main body 501. The magnet unit 542 includes a magnet 640. The magnet 640 applies a magnetic force to magnetic particles contained in liquid in the specimen treatment chip 100. For example, the magnet 640 fixes the magnetic particles at a predetermined position within the channel 201 of the fluid module 200 by using a magnetic force. The magnetic particles are cleaned by causing a cleaning liquid to flow to the magnetic particles fixed at a predetermined position. For example, the magnet unit 542 allows the magnet 640 to be movable in a longitudinal direction of the specimen treatment chip 100.

While illustration is eliminated, the same applies to the camera unit 545 and the cooling unit 543.

(Operation of Specimen Treatment Apparatus)

With reference to flowcharts of FIGS. 36 to 38, an example of operation of the specimen treatment apparatus 500 will be described.

<Control of Opening and Closing of Valve>

Figure 36:
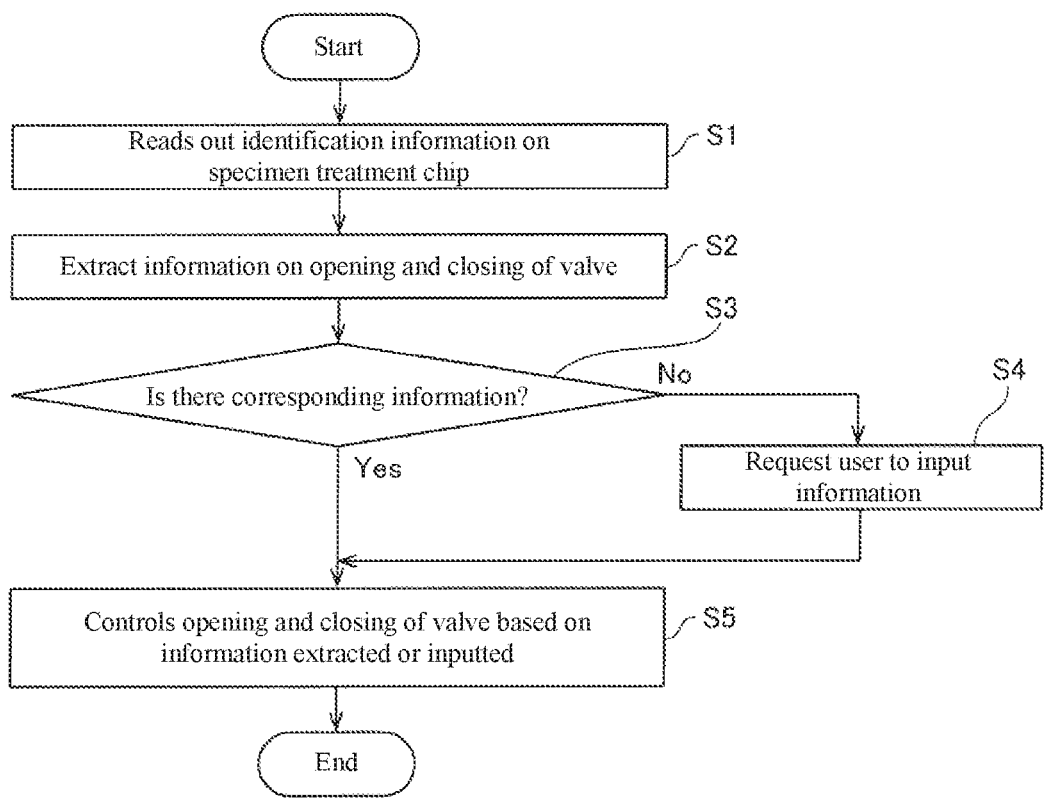
FIG. 36 is a flowchart illustrating an example of opening and closing control of a valve by a control unit.

In step S1 of FIG. 36, the specimen treatment apparatus 500 reads out identification information given to the specimen treatment chip 100. The identification information is given in the form of a bar code or QR code (registered trademark), for example, and the specimen treatment apparatus 500 reads out the identification information with the reading unit 533. The read-out information is transmitted to the control unit 530.

The identification information includes information determined according to a combination of fluid modules disposed in the specimen treatment chip 100, for example. The identification information may include information on other elements (e.g., a kind of assay method and the like) along with a combination of fluid modules. The identification information may include the following information, for example.

ID of the substrate flow channel 310 into which liquid is to be injected and positional information thereon.

ID of the substrate flow channel 310 from which liquid is to be recovered and positional information thereon.

Information indicating the order of injecting or recovering of liquid.

(e.g., the order is expressed by the placement order of the ID of the substrate flow channel 310 described above.)

Information indicating timing of injecting or recovering of liquid.

(e.g., the timing is expressed by an elapsed time from start of injection of the liquid or the amount of the injection, and the timing is set for each ID of the substrate flow channel 310 to which the liquid is to be injected.)

ID of liquid (a reagent, etc.) used for inspection.

Information indicating a position where liquid used for inspection is stored.

(e.g., the storage position is expressed by a number indicating the liquid reservoir 523 to which the liquid is to be stored, or the like.)

In step S2, the control unit 530 extracts information on opening and closing of a valve from read-out identification information. For example, the control unit 530 extracts ID of the substrate flow channel 310 related to injection or recovery of liquid and positional information thereon.

In step S3, the control unit 530 determines whether there is corresponding information. When it is determined that information on opening and closing of the valve is not included in the identification information, the control unit 530 causes processing to proceed to step S4. In this case, in step S4, the control unit 530 causes the monitor 531 of the specimen treatment apparatus 500 or a monitor (not illustrated) of a computer connected to the specimen treatment apparatus 500 to display contents prompting input of information on opening and closing of the valve.

When it is determined in step S3 that the identification information includes information on opening and closing of the valve, the control unit 530 causes the processing to proceed to step S5. In step S5, the control unit 530 controls opening and closing of each of the valves 522 of the liquid feeder 520 on the basis of the identification information read out from the specimen treatment chip 100 by the reading unit 533. When receiving information on opening and closing of the valve through the input unit 532, the control unit 530 controls the opening and closing of each of the valves 522 of the liquid feeder 520 on the basis of the received identification information.

The control unit 530 controls opening and closing of the valve 522 corresponding to the position of the substrate flow channel 310 related to injection or recovery of liquid. The control unit 530 controls the valve 522, corresponding to the position of the substrate flow channel 310 not related to the injection or recovery of the liquid, so as to be always closed during inspection.

When the control unit 530 is configured so as to control opening and closing of the valve 522 on the basis of identification information indicating a combination of the fluid modules 200, as described above, a user does not need to individually designate the valve 522 to be controlled for opening and closing every time using the specimen treatment chip 100 even in a case where the substrate flow channel 310 for injecting or recovering liquid differs according to the combination of the fluid modules 200.

In addition, when the control unit 530 is configured so as to control opening and closing of the valve 522 on the basis of the identification information received from the input unit 532, the valve 522 to be controlled for opening and closing can be changed according to the combination of the fluid modules 200 by a user who needs to only input the identification information at the time when the specimen treatment chip 100 is used. This improves convenience of the specimen treatment apparatus 500 when various kinds of specimen treatment chip 100 different in combination of the fluid modules 200 are used.

Further, when the control unit 530 is configured so as to control opening and closing of the valve 522 on the basis of the identification information read out from the specimen treatment chip 100 by the reading unit 533, the identification information does not need to be input when the specimen treatment chip 100 is used. As a result, even when various kinds of specimen treatment chip 100 different in combination of the fluid modules 200 are used, preparation work related to opening and closing of the valve 522 is unnecessary, thereby improving convenience of the specimen treatment apparatus 500.

<Control of Timing of Opening and Closing of Valve>

Figure 37:
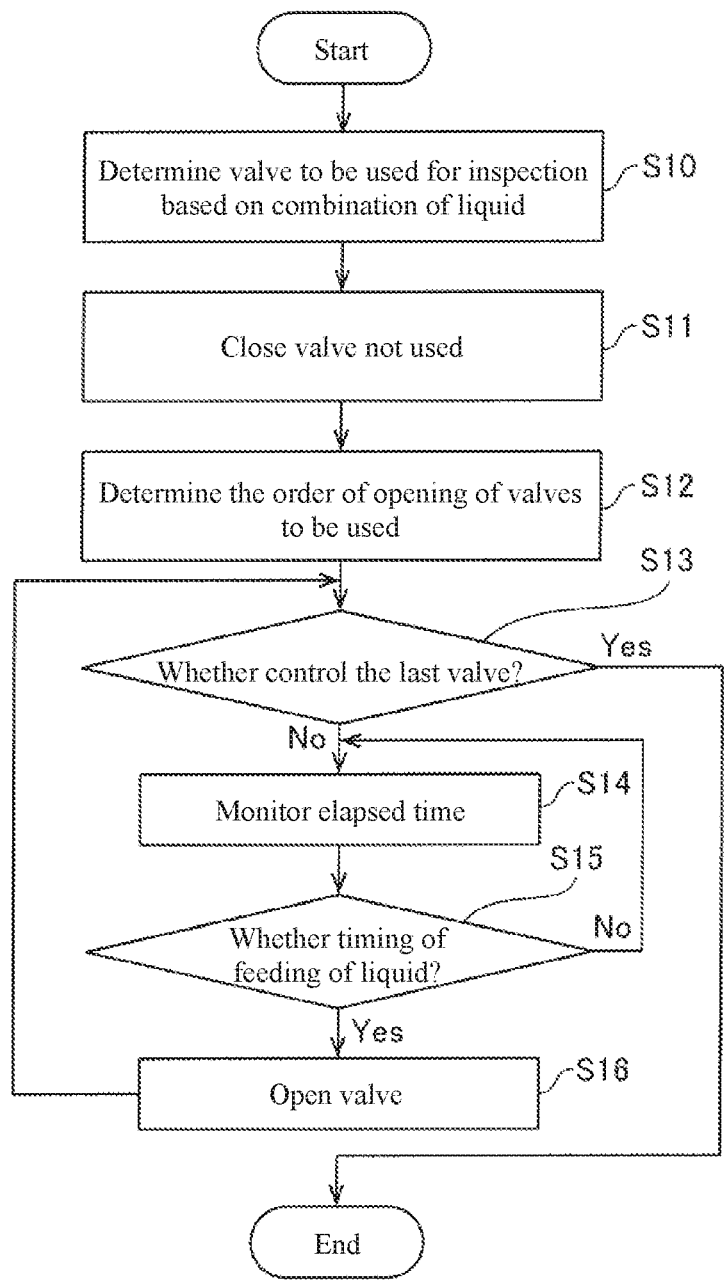
FIG. 37 is a flowchart illustrating an example of control of opening-closing timing of a valve by a control unit.

FIG. 37 illustrates an operation example when the control unit 530 controls timing of opening of the valve 522.

In step S10, the control unit 530 determines the valve 522 to be used for inspection on the basis of a combination of the fluid modules 200. The control unit 530 determines a position of the port 110 provided on the specimen treatment chip 100 to inject liquid into the fluid module 200 on the basis of a combination of the fluid modules 200, according to the operation illustrated in FIG. 36, for example. That is, the control unit 530 determines the substrate flow channel 310 serving as the port 110 for injecting the liquid. The control unit 530 controls opening and closing of each valve 522 of the liquid feeder 520 on the basis of the determined position of the port 110.

In step S11, the control unit 530 closes the valve 522 that is not used. In step S12, the control unit 530 determines the order of opening of the valves 522 used for inspection. For example, the control unit 530 determines the order of opening of the valves 522 on the basis of information (information indicating the order of injecting or recovering of liquid) included in the above-described identification information.

In step S13, the control unit 530 determines whether control of the last valve 522 in the determined order is completed. When it is determined that the control of the last valve 522 is not completed, the control unit 530 monitors an elapsed time from the start of injection of liquid into the specimen treatment chip 100 in step S14. For example, the control unit 530 monitors an elapsed time from the moment when the first valve 522 is opened.

In step S15, the control unit 530 determines whether timing of feeding of liquid into the specimen treatment chip 100 arrives. When it is determined that the timing of feeding of liquid into the specimen treatment chip 100 arrives, the control unit 530 opens the corresponding valve 522 in step S16. For example, the control unit 530 determines the timing of feeding of liquid based on whether the above-described elapsed time reaches timing extracted from the identification information. When it is determined that the elapsed time does not reach the timing of feeding of liquid, the control unit 530 causes processing to return to step S14 to monitor the elapsed time.

The control unit 530 repeats the operation of steps S14 to S16 until having performed the operation for all the valves 522 determined to be used in the inspection. When completing control of the last valve 522, the control unit 530 ends the processing.

When the control unit 530 is configured so as to determine a position of the port 110 for injecting liquid on the basis of a combination of the fluid modules 200, and to control opening and closing of each valve 522 of the liquid feeder 520 on the basis of the determined position of the port 110, as described above, it is possible to control a position of the port for injecting liquid, and to control opening and closing of the corresponding valve 522, only by designating a combination of the fluid modules 200. This improves convenience of the specimen treatment apparatus 500 when various kinds of specimen treatment chip 100 different in combination of the fluid modules 200 are used.

<Storage Process of Liquid into Liquid Reservoir>

Figure 38:
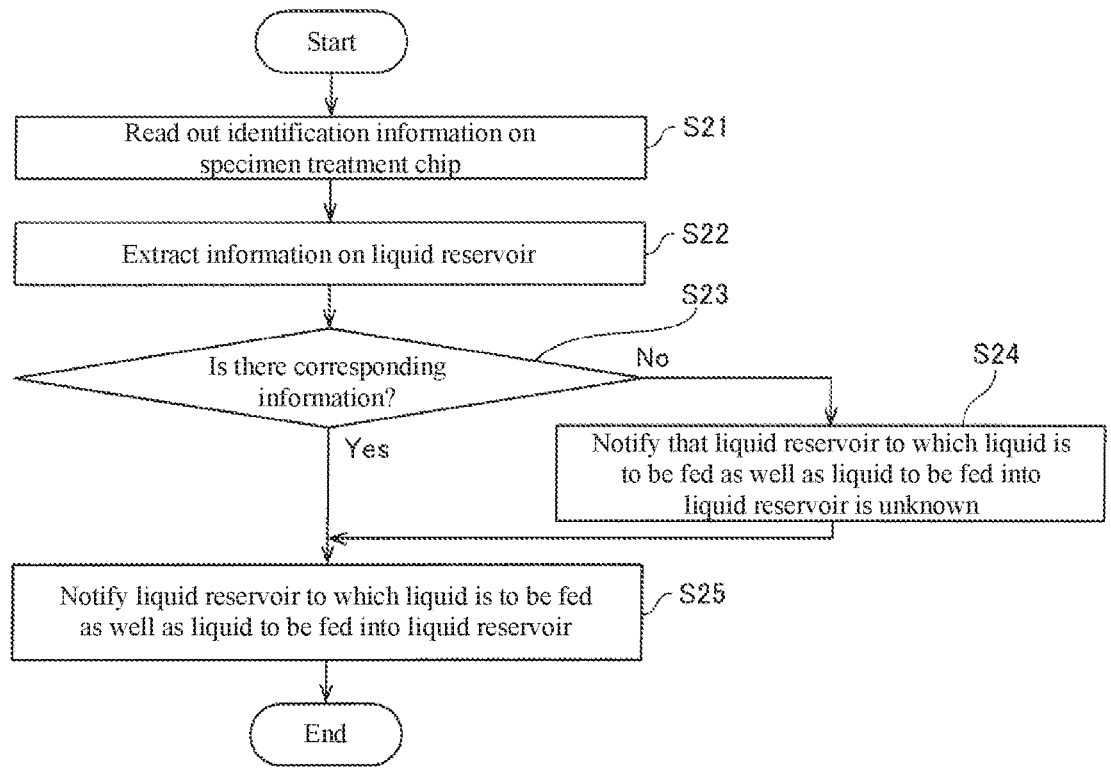
FIG. 38 is a flowchart illustrating an example of storage processing of liquid into a liquid reservoir by a control unit.

FIG. 38 illustrates an example of operation when liquid to be used for inspection is stored in a liquid reservoir.

Step S21 includes the same operation as that in step S1 in FIG. 36.

In step S22, the control unit 530 extracts information on the liquid reservoir 523 from the read-out identification information. For example, the control unit 530 extracts information indicating liquid (a reagent or the like) used for inspection, and information indicating a position storing the liquid to be used for the inspection.

In step S23, the control unit 530 determines whether there is corresponding information. When it is determined that information on the liquid reservoir 523 is not included in the identification information, the control unit 530 causes the monitor 531 to display the fact that the liquid reservoir 523 to which liquid is to be fed as well as the liquid to be fed into the liquid reservoir 523 is unknown, in step S24. The display may be performed by a monitor (not illustrated) of a computer connected to the specimen treatment apparatus 500.

When it is determined that related information is included in the identification information, the control unit 530 causes the monitor 531 to display the liquid reservoir 523 to which liquid is to be fed as well as a kind of liquid to be fed into the liquid reservoir 523, on the basis of the extracted information, in step S25. The liquid reservoir 523 as well as the kind of liquid is displayed to prevent erroneous operation by a user. The display may be performed by a monitor (not illustrated) of a computer connected to the specimen treatment apparatus 500.

[Example of Assay Using Specimen Treatment Chip]

Next, a specific example of an assay using the specimen treatment chip 100 will be described.

<Emulsion PCR Assay>

An example of performing an emulsion PCR assay using the above-described specimen treatment chip 100 will be described.

Figure 39:
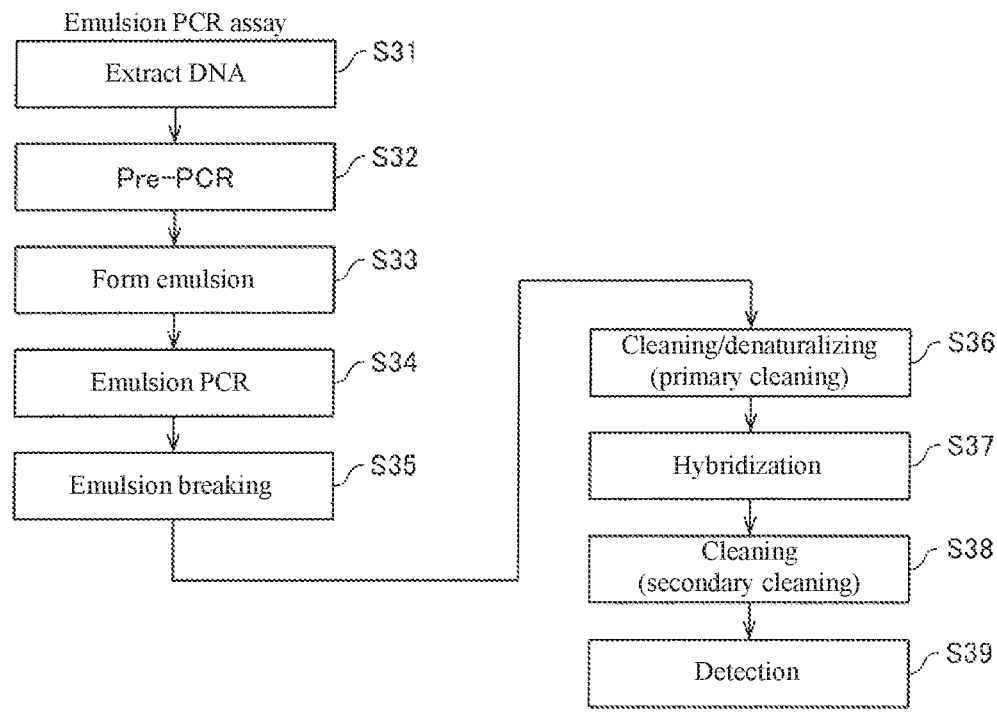
FIG. 39 is a flowchart illustrating an example of an emulsion PCR assay.
Figure 40:
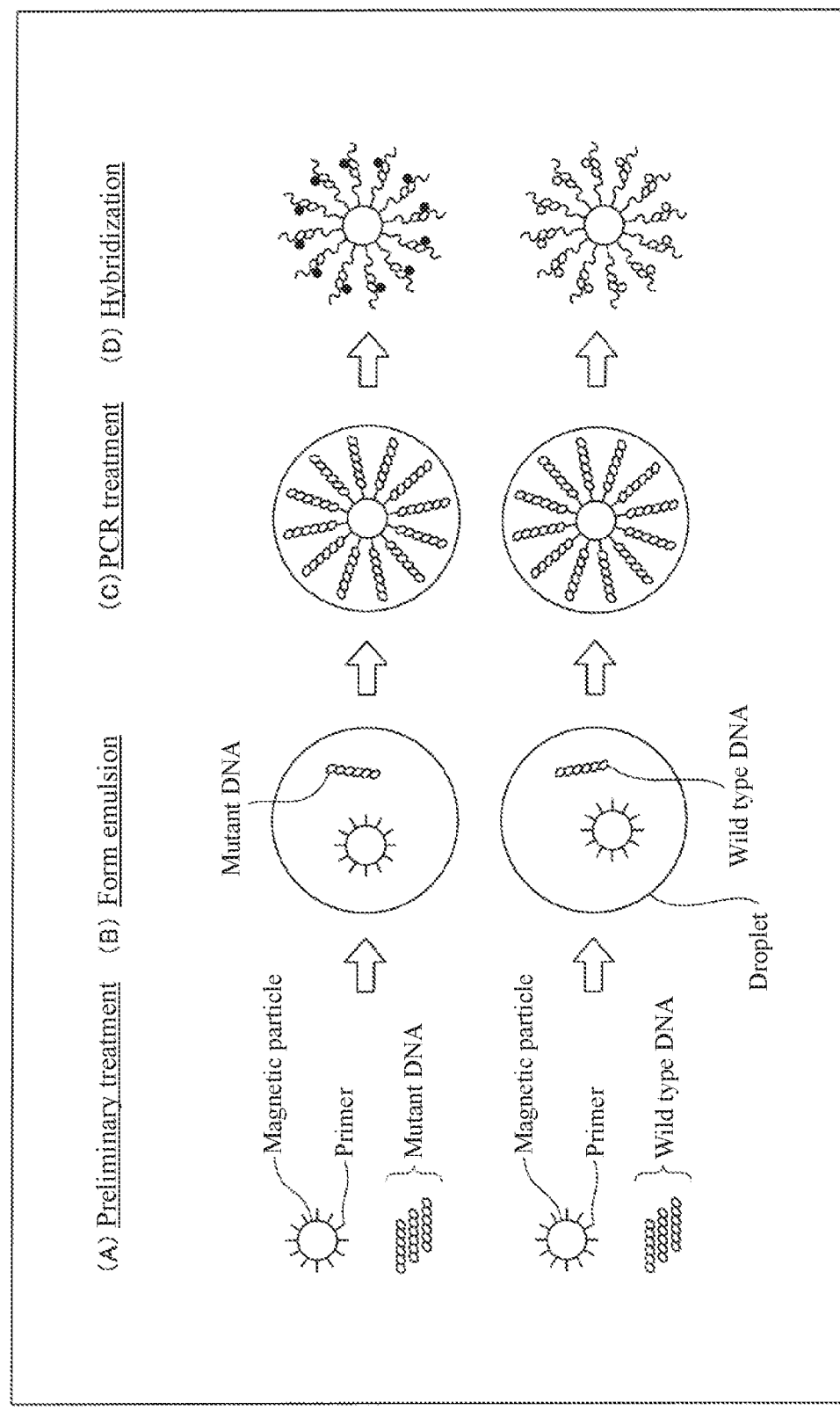
FIG. 40 illustrates progress of reaction in an emulsion PCR assay.

FIG. 39 illustrates an example of a flow of an emulsion PCR assay. FIG. 40 is a diagram for illustrating progress of reaction in the emulsion PCR assay.

In step S31, DNA is extracted from a sample such as blood by pretreatment (refer to FIG. 40 (A)). The pretreatment may be performed using a dedicated nucleic acid extraction device, or a pretreatment mechanism may be provided in the specimen treatment device 500.

In step S32, the extracted DNA is amplified by Pre-PCR treatment (refer to FIG. 40(A)). The Pre-PCR treatment is performed to preliminarily amplify the DNA contained in an extraction liquid after the pretreatment to the extent that subsequent emulsion creation treatment is possible. In the Pre-PCR treatment, the extracted DNA, and a reagent for PCR amplification, containing polymerase and primer, are mixed, and the DNA in the mixed liquid is amplified according to temperature control by a thermal cycler. The thermal cycler performs thermal cycle treatment of repeating one cycle changing temperature of the mixed liquid to a plurality of different temperatures, multiple times on the mixed liquid.

Step S33 is an emulsion forming step of forming in a dispersion medium a droplet containing a mixed liquid of nucleic acid (DNA) being an object component, a reagent for nucleic acid amplification reaction, and a carrier for nucleic acid. The reagent for nucleic acid amplification reaction contains a substance necessary for PCR such as DNA polymerase. In step S33, an emulsion containing a reagent including magnetic particles, polymerase, and the like, and DNA, is formed (refer to FIG. 40 (B)). An emulsion is a dispersion solution in which a liquid not mixed with the dispersion medium is dispersed in the dispersion medium. That is, in step S33, droplets each containing a mixed liquid of a reagent containing magnetic particles, polymerase, and the like, and DNA, are formed, and a large number of the droplets are dispersed into a dispersion medium. A primer for nucleic acid amplification is applied to a surface of each of the magnetic particles confined in the droplet. The droplet is formed such that the magnetic particle as well as a target DNA molecule is contained in the droplet to the extent of about one piece. The dispersion medium is immiscible to the mixed liquid. In the present example, the mixed liquid is water-based, and the dispersion medium is oil-based. The dispersion medium is oil, for example.

Step S34 is an emulsion PCR step of amplifying nucleic acid (DNA) in the droplet formed in the emulsion forming step. In step S34, DNA binds to the primer on the magnetic particle to be amplified in each of the droplets of the emulsion according to temperature control by the thermal cycler (emulsion PCR)(refer to FIG. 40(C)). This causes the target DNA molecule to be amplified in each of the droplets. That is, an amplification product of the nucleic acid is formed in each droplet. The amplified nucleic acid binds to a carrier through the primer in the droplet.

Step S35 is an emulsion breaking step of breaking down a droplet containing a carrier (magnetic particle) carrying an amplification product of nucleic acid (DNA) produced in the emulsion PCR step. That is, after DNA is amplified on a magnetic particle in step S34, an emulsion is broken down in step S35 and the magnetic particle containing the amplified DNA is extracted from a droplet (emulsion break). The emulsion is broken down using one or more kinds of emulsion breaking reagent containing alcohol, a surfactant, and the like.

Step S36 is a cleaning step of collecting carriers (magnetic particles) extracted from droplets broken down in the emulsion breaking step. In step S36, the magnetic particles extracted from the droplets are cleaned in a BF separation step (primary cleaning). The BF separation step is a treatment step in which the magnetic particle containing the amplified DNA is passed through a cleaning liquid while being collected by a magnetic force so that unnecessary substances adhering to the magnetic particle is removed. In the primary cleaning step, a cleaning liquid containing alcohol is used, for example. The alcohol not only removes an oil film on the magnetic particle, but also denaturalizes amplified double stranded DNA to a single strand.

Step S37 is a hybridization step in which the amplification product on the carrier (magnetic particle) collected in the cleaning step is reacted with a marking substance. After the cleaning, the DNA denaturalized to a single strand on the magnetic particle is hybridized with the marking substance for detection (hybridization) in step S37 (refer to FIG. 40 (D)). The marking substance includes a fluorescent substance, for example. The marking substance is designed to specifically bind to the DNA to be detected.

In step S38, the magnetic particle binding to the marking substance is cleaned in the BF separation step (secondary cleaning). The secondary BF separation step is performed by treatment similar to that of the primary BF separation step. In the secondary cleaning step, phosphate buffered saline (PBS) is used as a cleaning liquid, for example. The PBS removes an unreacted marking substance (including a marking substance that is nonspecifically adsorbed to the magnetic particle) that has not bound to DNA.

In step S39, the DNA is detected with a hybridized marking substance. The DNA is detected with a flow cytometer, for example. In the flow cytometer, the magnetic particle containing the DNA binding to the marking substance flows through a flow cell, and the magnetic particle is irradiated with a laser beam. Then, fluorescence emitted from the marking substance by being irradiated with the laser beam is detected.

The DNA may be detected by image processing. For example, the magnetic particles each containing the DNA binding to the marking substance are dispersed on a flat slide, and the dispersed magnetic particles are imaged by a camera unit. The number of the magnetic particles emitting fluorescence is counted on the basis of the imaged image.

(Configuration Example of Specimen Treatment Chip <Emulsion PCR Assay>)

Figure 41:
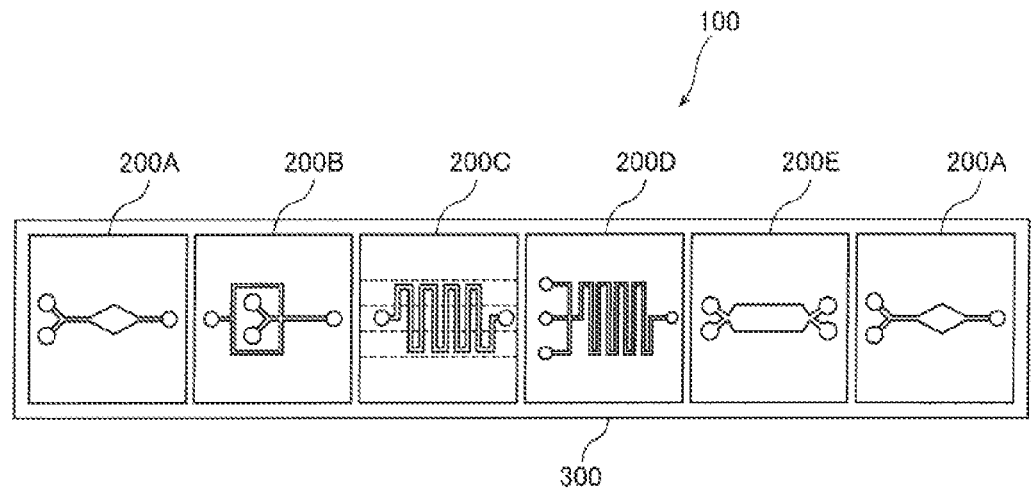
FIG. 41 illustrates a configuration example of a specimen treatment chip used in an emulsion PCR assay.

FIG. 41 illustrates a configuration example of a specimen treatment chip 100 used in an emulsion PCR assay.

The specimen treatment chip 100 of FIG. 41 is composed of a combination of a plurality of kinds of fluid module (200A to 200E) each having a different function. Liquid such as DNA being an object component, a reagent, and the like sequentially flow in each fluid module on the specimen treatment chip 100 to perform an emulsion PCR assay. The first treatment step of the first fluid module 250 and the second treatment step of the second fluid module 260 are two respective consecutive treatment steps selected from among the emulsion forming step (the first step), the emulsion PCR step (the second step), the emulsion breaking step (the third step), the cleaning step (fourth step) and the hybridization step (fifth step). This makes it possible to optimize each of fluid modules of the specimen treatment chip 100 used for the emulsion PCR assay to a structure suitable for a treatment step performed by the corresponding one of the fluid modules.

<Pre-PCR>

Figure 42:
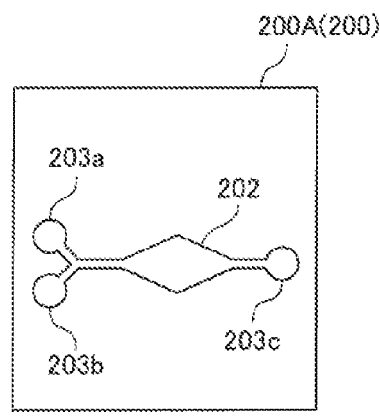
FIG. 42 illustrates a configuration example of a fluid module used for Pre-PCR.

FIG. 42 illustrates a configuration example of a fluid module 200A used for Pre-PCR. The fluid module 200A includes a channel 202, connection portions 203a and 203b for injecting a reagent and a specimen, and a connection portion 203c for discharging liquid. The channel 202 is formed in a diamond shape, for example, to control a flow rate of liquid.

The fluid module 200A is formed of a material with high heat resistance, such as polycarbonate. The channel 202 is formed with a height 50 µm to 500 µm, for example. The fluid module 200A can be molded with not only a precision Si mold but also a machined mold.

For example, DNA extracted in pretreatment is injected from the connection portion 203a, and a PCR amplification reagent is injected from the connection portion 203b. The mixed liquid of the DNA and the reagent is controlled by the heater 541 for temperature in the course of flowing through the channel 202. The DNA and the reagent react with each other with temperature control to amplify the DNA. The liquid containing the amplified DNA is fed to the adjacent fluid module 200 through the connection portion 203c.

<Forming of Emulsion>

Figure 43:
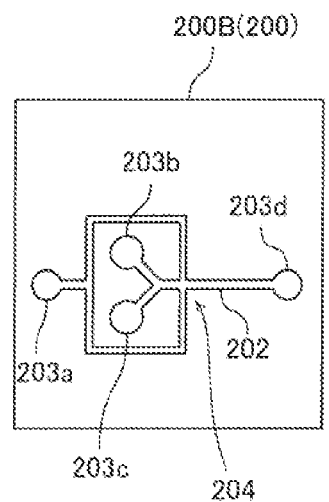
FIG. 43 illustrates a configuration example of a fluid module used for forming an emulsion.

FIG. 43 illustrates a configuration example of a fluid module 200B used for forming an emulsion. The fluid module 200B includes a channel 202, connection portions 203a, 203b, and 203c into which liquid such as a specimen or a reagent is injected, and a connection portion 203d from which a liquid is discharged. The channel 202 has an intersection 204 at which at least two channels intersect. Each channel forming the intersection 204 has a width of several tens of µm. In the present embodiment, the channel has a width of 20 µm. The fluid module 200B may include only one of the connection portions 203b and 203c.

The channel 202 of the fluid module 200B has a height of 10 µm to 20 µm, for example. Thus, the fluid module 200B is molded with a precision Si mold or the like manufactured by photolithography and etching, for example. To improve wettability to oil, the channel 202 has a wall surface treated with a hydrophobic material or fluorine, for example. The fluid module 200B is made of a material such as PDMS, PMMA, or the like, for example.

For example, liquid containing DNA amplified by Pre-PCR is injected from the connection portion 203b, and liquid containing a magnetic particle and a reagent for PCR amplification is injected from the connection portion 203c. The liquids injected from the respective connection portions 203b and 203c are mixed in the channel 202 to flow into the intersection 204. The magnetic particle has a particle diameter of 0.5 µm to 3 µm, for example. The pump 521 applies pressure P (P is 1000 mbar or more and 10000 mbar or less) to feed liquid to the connection portions 203b and 203c.

For example, oil for forming an emulsion is injected from the connection portion 203a. The injected oil is divided into a plurality of paths in the channel 202 to flow into the intersection 204 from the divided paths. The pump 521 applies pressure P (P is 1000 mbar or more and 10000 mbar or less) to feed oil to the connection portion 203a.

To increase resistance to the pressure applied by the pump 521, it is preferable that the substrate 300 has a thickness d of 2 mm or more in the present embodiment. For example, liquid under a pressure of about 8000 mbar may cause a crack in the substrate 300 when it is too thin. The substrate 300 with a thickness d of 2 mm or more prevents a crack in the substrate 300.

Figure 44:
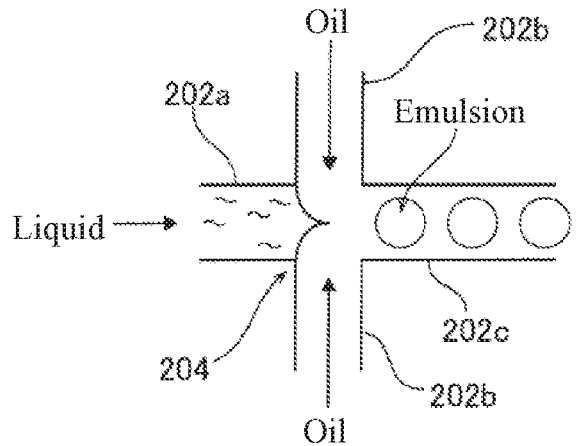
FIG. 44 is an enlarged view illustrating a first example of an intersection where an emulsion is formed.

FIG. 44 illustrates an example in which an emulsion is formed at an intersection 204. Mixed liquid of DNA and a reagent flows into the intersection 204 into which oil flows from top and bottom in FIG. 44. The mixed liquid is divided into droplets by a shear force generated by being pressed by the oil at the intersection 204. The divided droplets are surrounded by the oil flowing into the intersection 204 to form an emulsion. The emulsion formed from a flow of a specimen is fed into the adjacent fluid module 200 through the connection portion 203d.

For example, the mixed liquid of DNA and the reagent flows into the intersection 204 at a flow rate of 0.4 µL/min to 7 µL/min, and the oil flows into the intersection 204 at a flow rate of 1 µL/min to 50 µL/min. The flow rate is controlled by pressure applied by the pump 521. For example, when the mixed liquid of DNA and the reagent, and the oil are caused to flow into the intersection 204 at flow rates of 2 µL/min (about 5200 mbar) and 14 µL/min (about 8200 mbar), respectively, droplets of about 10 million pieces/min are formed. The droplets are formed at a rate of about 600,000 pieces/min to about 18 million pieces/min (about 10,000 pieces/sec to about 300,000 pieces/sec), for example. To form droplets at high speed as described above, it is necessary to apply a high pressure to the specimen treatment chip 100. As described above, the substrate 300 capable of withstanding high pressure can be easily obtained by setting the thickness d of the substrate 300 and selecting the material of the substrate 300. In addition, use of the substrate flow channel 310 provided in the substrate 300 as the liquid injection port 110 enables pressure resistance performance of the liquid injection port 110 of the specimen treatment chip 100 to be easily improved. Forming the substrate flow channel 310 in a simple shape such as a through hole in the thickness direction is also effective in improving the pressure resistance performance.

Figure 45:
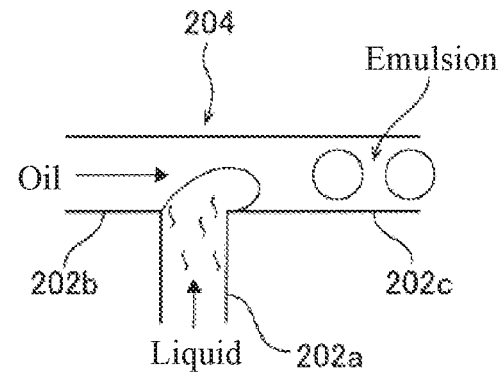
FIG. 45 is an enlarged view illustrating a second example of an intersection where an emulsion is formed.

In the example of FIG. 44, the intersection 204 is formed in a cross shape by a total of four channels 202 including one channel 202a into which mixed liquid flows, two channels 202b into which oil flows, and one channel 202c through which an emulsion flows out. The intersection 204 may be formed in a T shape by three channels 202, as illustrated in FIG. 45. In the case of FIG. 45, mixed liquid flows from the channel 202a, and oil flows from the channel 202b. Due to a shear force generated by a flow of the oil, the mixed liquid turns into droplets in the oil to form an emulsion.

<PCR>

Figure 46:
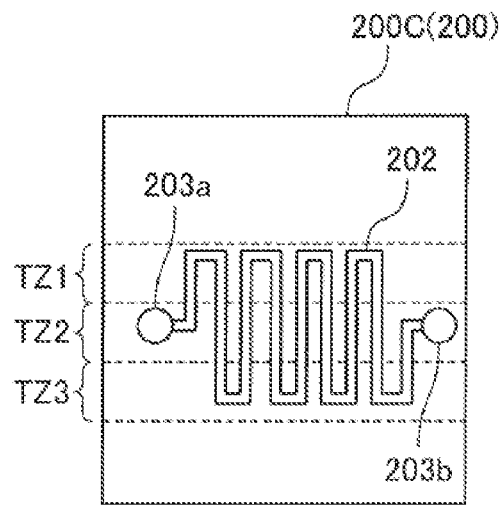
FIG. 46 illustrates a configuration example of a fluid module used for PCR.

FIG. 46 illustrates a configuration example of a fluid module 200C used for emulsion PCR. The fluid module 200C includes a channel 202, a connection portion 203a into which liquid flows, and a connection portion 203b through which liquid is discharged.

The fluid module 200C is formed of a material with high heat resistance, such as polycarbonate. The channel 202 is formed with a height 50 µm to 500 µm, for example. The fluid module 200C can be molded with not only a precision Si mold but also a machined mold.

The channel 202 has such a structure that it passes through a plurality of temperature zones TZ1 to TZ3 formed by the heater 541 multiple times. The number of temperature zones TZ may be any number other than three. The number of times that the channel 202 passes through the respective temperature zones TZ1 to TZ3 corresponds to the number of thermal cycles. That is, the channel 202 is formed according to the number of thermal cycles required for emulsion PCR. The number of thermal cycles of the emulsion PCR is set to about 40, for example. Thus, while illustrated in a simplified manner in FIG. 46, the channel 202 is formed in a reciprocating shape or meandering shape for the number of times corresponding to the number of cycles so as to traverse the temperature zones TZ1 to TZ3 about 40 times.

As illustrated in FIG. 46, DNA in each droplet is amplified in the course of flowing through the channel 202. The droplet containing the amplified DNA is fed to the adjacent fluid module 200D through the connection portion 203*b*.

<Emulsion Break>

Figure 47:
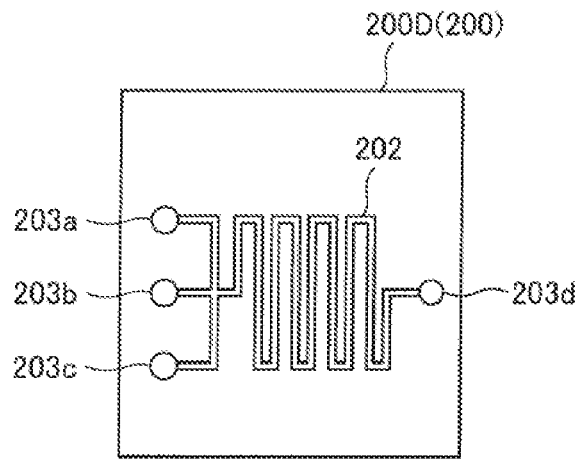
FIG. 47 illustrates a configuration example of a fluid module used for an emulsion break.

FIG. 47 illustrates a configuration example of a fluid module 200D used for breaking an emulsion. The fluid module 200D has a function of mixing a plurality of kinds of liquid. The fluid module 200D includes a channel 202, connection portions 203*a*, 203*b*, and 203*c* into each of which an emulsion or a reagent for breaking an emulsion flows, and a connection portion 203*d* through which liquid is discharged.

The fluid module 200D is formed of a material with high chemical resistance, such as polycarbonate or polystyrene, for example. The channel 202 is formed with a height of 50 μm to 500 μm, for example. The fluid module 200D can be molded with not only a precision Si mold but also a machined mold.

For example, an emulsion having undergone the emulsion PCR step flows from the connection portion 203*b*, and a reagent for breaking an emulsion flows from the connection portions 203*a* and 203*c*. The emulsion and the reagent for breaking an emulsion are mixed in the course of flowing through the channel 202 to break down droplets in the emulsion. The channel 202 is formed in such a shape that promotes mixing of liquid. For example, the channel 202 is formed such that liquid flows back and forth multiple times in a width direction of the specimen treatment chip 100. A magnetic particle extracted from a droplet is fed to the adjacent fluid module 200 through the connection portion 203*d*.

<Cleaning (Primary Cleaning)>

Figure 48:
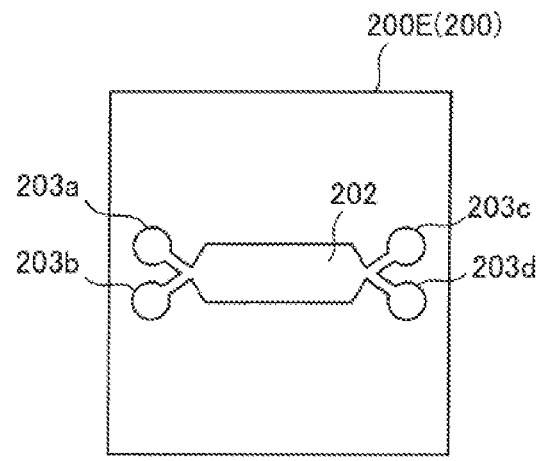
FIG. 48 illustrates a configuration example of a fluid module used in a cleaning step (primary cleaning).

FIG. 48 illustrates a configuration example of a fluid module 200E used in the cleaning step (primary cleaning). The fluid module 200E includes connection portions 203*a* and 203*b* into which liquid flows, connection portions 203*c* and 203*d* from which liquid is discharged, and a channel 202. The channel 202 has a shape extending linearly in a predetermined direction, such as a substantially rectangular shape, for example. In addition, the channel 202 has a wide shape so as to be able to sufficiently collect and disperse magnetic particles. The channel 202 is provided on its one end side with the connection portions 203*a* and 203*b* on an inflow side, and is provided on its the other end side with the connection portions 203*c* and 203*d* on a discharge side.

The fluid module 200E is formed of a material with high chemical resistance, such as polycarbonate or polystyrene, for example. The channel 202 is formed with a height of 50 μm to 500 μm, for example. The fluid module 200E can be molded with not only a precision Si mold but also a machined mold.

Figure 49:
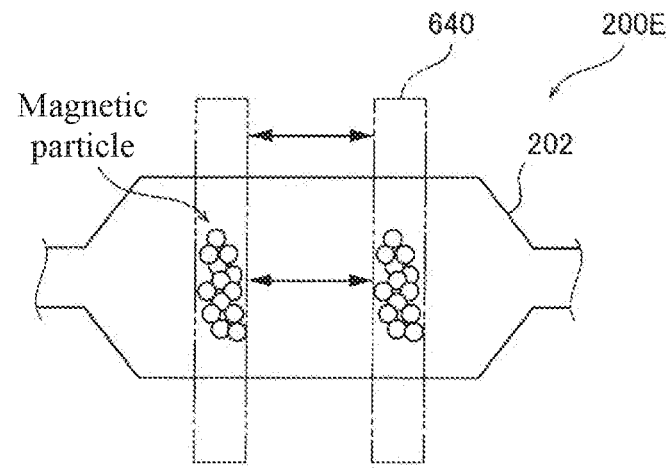
FIG. 49 illustrates an example of operation of cleaning and concentrating magnetic particles with a fluid module.

FIG. 49 illustrates an operation example of cleaning and concentrating magnetic particles by the fluid module 200E. Liquid containing magnetic particles flows from the connection portion 203*a* toward the connection portion 203*c*. The magnetic particles in the liquid are concentrated by a magnetic force of the magnet 640. The magnet 640 can reciprocate in a longitudinal direction of the channel 202. The magnetic particles are agglomerated while flowing back and forth in the channel 202 in accordance with reciprocating motion of the magnet 640.

From the connection portion 203*b*, a cleaning liquid is supplied. The cleaning liquid continuously flows from the connection portion 203*b* toward the connection portion 203*d*. The connection portion 203*d* serves as a drain for discharging the cleaning liquid. The magnetic particles flow back and forth in a flow of the cleaning liquid in the channel 202 in accordance with motion of the magnet 640 to perform cleaning treatment. The magnetic particles flow back and forth in the channel 202 in accordance with motion of the magnet 640 to be prevented from sticking to each other in a massive form.

In the primary cleaning step, a cleaning liquid containing alcohol is used. The primary cleaning using the cleaning liquid removes an oil film on the magnetic particle to denaturalize amplified double stranded DNA to a single strand. The magnetic particles having being cleaned and concentrated are discharged from the connection portion 203*b* to be fed to the adjacent fluid module 200A.

<Hybridization>

The magnetic particles are mixed with a reagent containing a marking substance in the fluid module 200A with a similar structure to that in FIG. 42 to be subjected to a thermal cycle. For example, liquid containing magnetic particles is fed from the connection portion 203*a*, and a reagent containing a marking substance is injected from the connection portion 203*b*. The thermal cycle causes DNA on the magnetic particle and the marking substance to bind to each other.

<Cleaning (Secondary Cleaning)>

The secondary cleaning step after hybridization (binding) with the marking substance may be performed by the fluid module 200A. For example, a cleaning liquid is injected from the connection portion 203*b* while magnetic particles are magnetically collected in the channel 202 by the magnet 640 (refer to FIG. 49), in FIG. 42. In the secondary cleaning step, PBS is used as the cleaning liquid. The secondary cleaning using the cleaning liquid removes an unreacted marking substance (including a marking substance nonspecifically adsorbed to a magnetic particle) that has not bound to DNA. The magnetic particle containing the marking substance after the secondary cleaning is discharged from the connection portion 203*c*. In this case, it is preferable that the fluid module 200A is also provided with a connection portion 203 on the discharge side for draining, as with the fluid module 200E (refer to FIG. 48).

The fluid module 200E that performs the secondary cleaning may be added downstream of the fluid module 200A that performs hybridization.

<Modification of Primary Cleaning, Hybridization, and Secondary Cleaning>

As another configuration example, the primary cleaning, the hybridization, and the secondary cleaning may be performed in one fluid module 200E (refer to FIG. 48). In this case, a sample after emulsion breaking is injected into the channel 202 from the connection portion 203*a* to be magnetized by the magnet 640. From the connection portion 203*b*, an alcohol-containing cleaning liquid for the primary cleaning, a marking reagent for the hybridization, and a cleaning liquid (PBS) for the secondary cleaning are sequentially injected to perform treatment processing of each step.

In this case, there is no need to provide the fluid module 200A downstream of the fluid module 200E.

<Detection>

A magnetic particle containing the marking substance after the secondary cleaning is detected by a flow cytometer, or image analysis, for example. Because a flow cytometer is used for detection, the magnetic particle containing the marking substance is recovered from the specimen treatment apparatus 500 to be fed to the flow cytometer that is separately provided, for example. In the magnetic particle containing the marking substance, fluorescence or the like based on marking is detected by the detector 544 of the specimen treatment apparatus 500. In addition, the magnetic particle containing the marking substance is photographed by the camera unit 545 of the specimen treatment apparatus 500, and then an image photographed is analyzed by the specimen treatment apparatus 500 or a computer connected to the specimen treatment apparatus 500.

<Single Cell Analysis>

Figure 50:
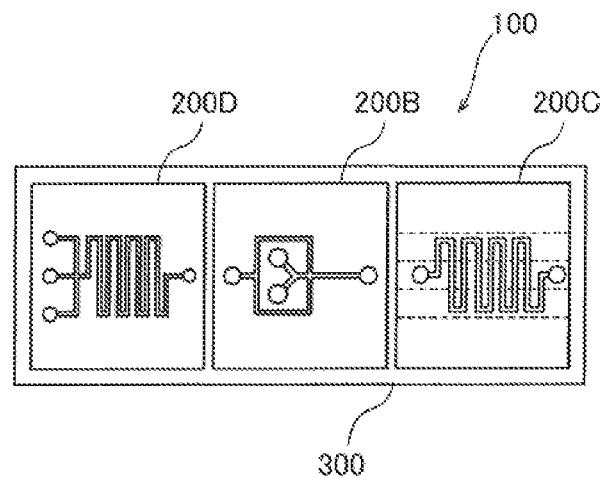
FIG. 50 illustrates a configuration example of a specimen treatment chip used for single cell analysis.

An example in which single cell analysis is performed using the above-described specimen treatment chip 100 will be described. The single cell analysis is a method for performing analysis on a cell-by-cell basis using individual cells contained in a sample, such as blood, as an analysis target. FIG. 50 illustrates a configuration example of a specimen treatment chip 100 used for the single cell analysis.

The specimen treatment chip 100 is composed of a combination of a liquid module 200D for mixing liquid, a fluid module 200B for forming an emulsion, and a fluid module 200C for PCR amplification, for example.

The single cell analysis includes a step (first step) of mixing a cell as an object component with a reagent for amplification reaction of a nucleic acid in a cell, a step (second step) of forming a droplet containing a mixed liquid of the liquid mixed in the first step and a cell lysis reagent in a dispersion medium, and a step (third step) of amplifying the nucleic acid eluted from the cell in the droplet in the second step, in the droplet. The first treatment step of the first fluid module 250 and the second treatment step of the second fluid module 260 are two respective consecutive treatment steps selected from among the first step, the second step, and the third step. This makes it possible to optimize each of fluid modules of the specimen treatment chip 100 used for the single cell analysis to a structure suitable for the treatment step performed by the corresponding one of the fluid modules.

The configuration (material, channel height, etc.) of the fluid module 200D is similar to that illustrated in FIG. 47, so that a detailed description thereof is eliminated.

A specimen such as blood is injected from the connection portion 203b of the fluid module 200D, and the PCR amplification reagent is injected from the connection portions 203a and 203c. Cells contained in the specimen and the PCR amplification reagent are mixed in the course of flowing through the channel 202. The mixed liquid is fed to the adjacent fluid module 200B through the connection portion 203c.

The configuration (material, channel height, etc.) of the fluid module 200B is similar to that illustrated in FIG. 43, so that a detailed description thereof is eliminated.

A mixed liquid of a cell, a reagent for PCR amplification, and a fluorescent dye is injected from the connection portion 203b of the fluid module 200B. A cell lysis reagent is injected from the connection portion 203c. Oil for forming an emulsion is injected from the connection portion 203a. The mixed liquid of the cell, the PCR amplification reagent, and the cell lysis reagent becomes droplets wrapped in oil at the intersection 204 to form an emulsion. Each of the droplets enclosing the mixed liquid is fed to the adjacent fluid module 200C through the connection portion 203c. A cell in each of the droplets is dissolved by the cell lysis reagent in the course of feeding of the emulsion to the fluid module 200C from the dissolved cell, intracellular DNA is eluted into a droplet containing the PCR amplification reagent.

The configuration (material, channel height, etc.) of the fluid module 200C is similar to that illustrated in FIG. 46, so that a detailed description thereof is eliminated.

The emulsion fed to the fluid module 200C is subjected to a thermal cycle in the course of flowing through the channel 202 of the fluid module 200C. The thermal cycle causes the DNA eluted from the cell in the droplet to be amplified. A protein eluted from the cell in the droplet may be detected by enzyme reaction, substrate reaction, or the like.

(Immunoassay <Digital ELISA>)

Figure 51:
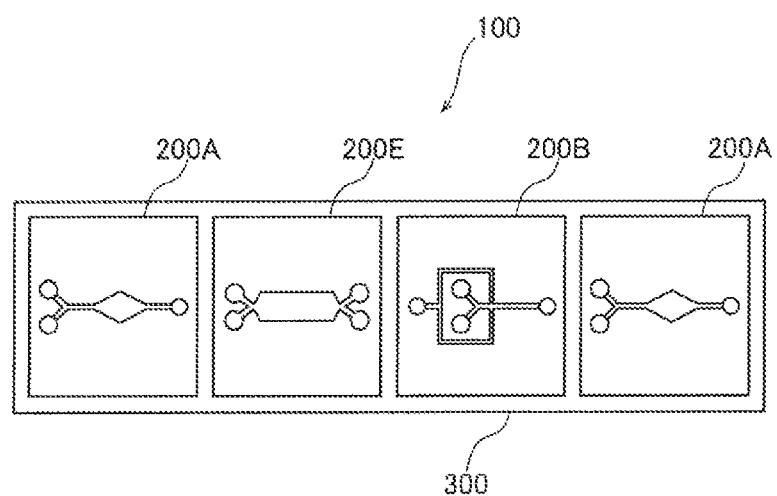
FIG. 51 illustrates a configuration example of a specimen treatment chip used for immunoassay.

An example of performing immunoassay using the above-described specimen treatment chip 100 will be described. In the immunoassay, a protein such as an antigen and an antibody contained in blood or the like is an object component. FIG. 51 illustrates a configuration example of a specimen treatment chip 100 used in Digital ELISA (Enzyme-Linked ImmunoSorbent Assay).

The specimen treatment chip 100 is composed of a combination of a fluid module 200A for temperature control, a fluid module 200E for BF separation, a fluid module 200B for forming an emulsion, and a fluid module 200A for temperature control.

Figure 52:
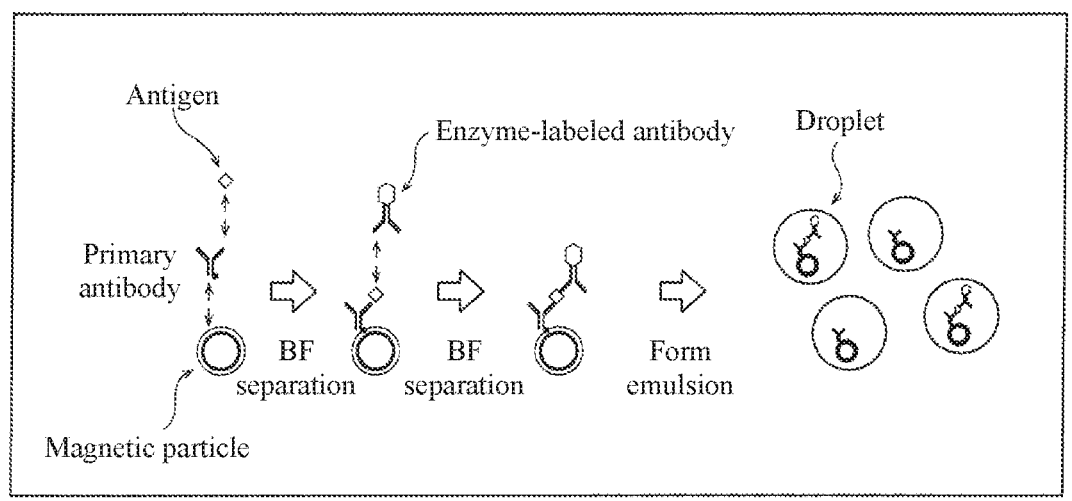
FIG. 52 illustrates progress of reaction in immunoassay.

FIG. 52 illustrates an outline of Digital ELISA. The ELISA is a method in which an antigen (that may be an antibody) to be an object component and a marking substance are supported on a magnetic particle to form an immunocomplex so that the object component is detected on the basis of a mark in the immunocomplex. The Digital ELISA is a method in which a sample subjected to limiting dilution (diluted so that each microsection includes one or zero object component) is dispersed so that the number of microsections in which a signal based on a mark is positive is directly counted to absolutely measure concentration of the object component in the sample. In the case of FIG. 52, each individual droplet in an emulsion is a microsection. The assay illustrated in the example of FIG. 52 is performed using the specimen treatment chip 100.

More specifically, the Digital ELISA assay includes a step (first step) of forming an immunocomplex in which an object component (antigen or antibody) is caused to bind to a carrier by antigen-antibody reaction, a step (second step) of causing the immunocomplex formed in the first step to react with a marking substance, a step (third step) of forming a droplet containing the immunocomplex binding to the marking substance in the second step and a substrate for detecting the marking substance in a dispersion medium, and a step (fourth step) of causing the substrate to react with the marking substance in the droplet formed in the third step. The first treatment step of the first fluid module 250 and the second treatment step of the second fluid module 260 are two respective consecutive treatment steps selected from among the first step, the second step, the third step, and the fourth step. This makes it possible to optimize each of fluid modules of the specimen treatment chip 100 used for the Digital ELISA assay to a structure suitable for a treatment step performed by the corresponding one of the fluid modules.

The configuration (material, channel height, etc.) of the fluid module 200A is similar to that illustrated in FIG. 42, so that a detailed description thereof is eliminated.

A specimen containing an antigen is injected from the connection portion 203a of the fluid module 200A, and a reagent containing a primary antibody and a magnetic particle is injected from the connection portion 203b. The specimen and the reagent are mixed in the channel 202. The mixed liquid is subjected to temperature control in the channel 202 so that an immunocomplex including the antigen, the primary antibody, and the magnetic particle is produced. Then, temperature is controlled from about 40° C. to about 50° C., more preferably about 42° C. The liquid containing the complex produced is fed to the adjacent fluid module 200E through the connection portion 203c.

The configuration (material, channel height, etc.) of the fluid module 200E is similar to that illustrated in FIG. 48, so that a detailed description thereof is eliminated.

In the channel 202 of the fluid module 200E, the complex containing the magnetic particle is collected by the magnet 640 and cleaned (primary BF separation). After the primary BF separation, influence of a magnetic force by the magnet 640 is eliminated so that the immunocomplex is dispersed. The dispersed immunocomplex is caused to react with an enzyme-labeled antibody. After the reaction, the immunocomplex is collected again by the magnet 640 and cleaned (secondary BF separation). After being cleaned, the immunocomplex is fed to the adjacent fluid module 200B.

The configuration (material, channel height, etc.) of the fluid module 200B is similar to that illustrated in FIG. 43, so that a detailed description thereof is eliminated.

The complex is injected from the connection portion 203b of the fluid module 200B, and a reagent containing a fluorescent and luminescent substrate is injected from the connection portion 203c. Oil for forming an emulsion is injected from the connection portion 203a. The liquid containing the immunocomplex, and the reagent containing the fluorescent and luminescent substrate, are wrapped in oil at the intersection 204 to form a droplet to form an emulsion. The emulsion is fed to the adjacent fluid module 200A from the connection portion 203c.

The emulsion fed to the fluid module 200A is heated in the channel 202, so that the substrate and the immunocomplex react with each other in each individual droplet to generate fluorescence. The detector 544 of the specimen treatment apparatus 500 detects fluorescence. As a result, it is possible to detect an object component contained in each droplet in units of one molecule.

(PCR Assay)

An example of performing a PCR assay using the above-described specimen treatment chip 100 will be described.

Figure 53:
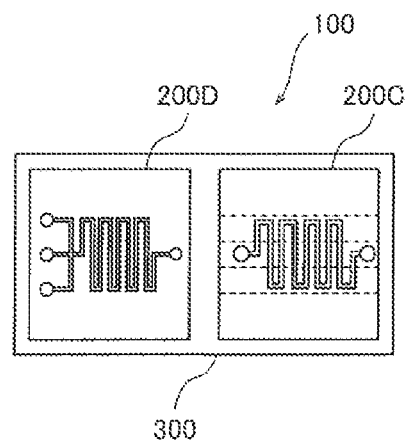
FIG. 53 illustrates a configuration example of a specimen treatment chip used in a PCR assay.

FIG. 53 illustrates a configuration example of a specimen treatment chip 100 used in a PCR assay.

In the fluid module 200D, a nucleic acid being an object component and a reagent for amplifying a gene are mixed. For example, in amplification of a displaced gene by a clamp PCR method, a reagent for amplifying a gene, containing a probe that selectively binds to a mutant gene, is mixed with an object component. The mixed sample is fed to the adjacent fluid module 200C from the connection portion 203d. In the fluid module 200C, PCR is performed in a continuous fluid under temperature control by the heater 541. In the example of FIG. 53, a simple real time PCR using a small specimen treatment chip 100 becomes possible, so that it is possible to achieve a small chip for a point of care (POC) for performing inspection and diagnosis at a patient's treatment site.

An assay using the specimen treatment chip 100 is not limited to the above example, and the specimen treatment chip 100 may be configured for any other assay by combining fluid modules 200.

(Reservoir of Specimen Treatment Chip)

Figure 54:
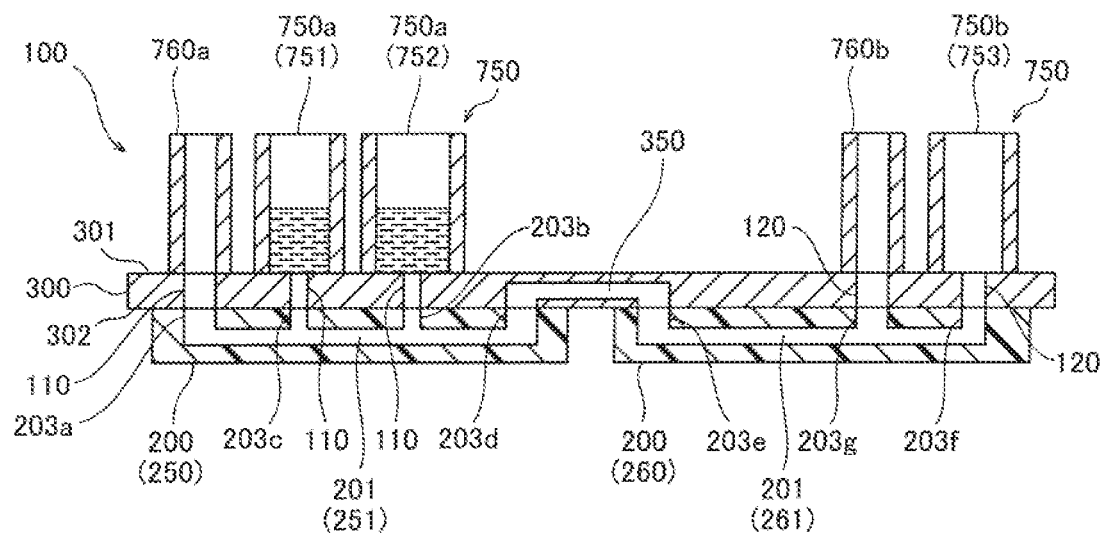
FIG. 54 illustrates a configuration example of a specimen treatment chip provided with a reservoir.

FIG. 54 illustrates an example in which a reservoir for storing liquid is provided in a specimen treatment chip 100.

In the configuration example of FIG. 54, a substrate 300 includes ports 110 and 120 connected to a flow channel 201 of a fluid module 200, and the specimen treatment chip 100 includes a reservoir 750 that is provided on a surface of the substrate 300 so as to be connected to the ports 110 and 120. The reservoir 750 includes a reservoir 750a for storing liquid to be injected into the fluid module 200 or a reservoir 750b for storing liquid to be fed out from the fluid module 200. In the configuration example of FIG. 54, the reservoir 750 is provided on a first surface 301 that is an upper surface of the substrate 300.

The reservoir 750 is configured to store liquid such as a specimen and a reagent to be supplied to the fluid module 200, or to store liquid fed from the fluid module 200 after being treated in the flow channel 201. When the reservoir 750a for storing liquid to be injected into the fluid module 200 is provided, the liquid to be used in the fluid module 200 can be easily poured into the reservoir 750 by using a pipetter due to the reservoir 750a disposed on the surface of the substrate 300. The reservoir 750a is disposed on a surface of the specimen treatment chip 100, so that a user using a pipetter can easily pipet the liquid into the reservoir 750a. When the reservoir 750b for storing liquid to be fed out from the fluid module 200 is provided, the liquid after being treated in the flow channel can be stored until proceeding to the next treatment. Work of extracting the liquid from the reservoir 750b for the next treatment can also be easily performed using a pipetter.

When the reservoir 750 for storing a specimen containing an object component is provided in the specimen treatment chip 100, a specimen can be fed to the fluid module 200 from the reservoir 750 without using a path for feeding liquid, such as the liquid feeding pipe 526 of the specimen treatment apparatus 500 or the like. When a specimen is fed to the fluid module 200 by using the liquid feeding pipe 526 of the specimen treatment apparatus 500, the specimen remaining in the liquid feeding pipe 526 may mix with another specimen to be subjected to next treatment. Thus, when a specimen is fed to the fluid module 200 by using the liquid feeding pipe 526 of the specimen treatment apparatus 500, it is desirable to perform a process of cleaning the inside of the liquid feeding pipe 526 or to replace the liquid feeding pipe 526, every time specimen treatment is performed. In a configuration in which the specimen treatment chip 100 includes the reservoir 750, a specimen does not need to be fed from a specimen treatment apparatus 500 side. As a result, contamination at the time of feeding a specimen to the specimen treatment chip 100 can be prevented without cleaning the liquid feeding pipe 526 or replacing the liquid feeding pipe 526. Even when liquid containing a specimen after being treated in the fluid module 200 is recovered, the liquid containing the specimen can be stored in the reservoir 750 of the specimen treatment chip 100 without being fed using the liquid feeding pipe 526 of the specimen treatment apparatus 500. Thus, it is possible to prevent contamination when a specimen is recovered from the specimen treatment chip 100 without cleaning the liquid feeding pipe 526 or replacing the liquid feeding pipe 526.

In a configuration in which the reservoir 750 is provided in the specimen treatment chip 100, a movement distance of liquid between a structure storing liquid to be supplied to the fluid module 200 and the fluid module 200 can be reduced as much as possible. For example, in a configuration in which a specimen is fed from the specimen holding unit 524 (refer to FIG. 19) of the specimen treatment apparatus 500 through the liquid feeding pipe 526, the specimen holding unit 524 and the fluid module 200 are connected to each other through the liquid feeding pipe 526 and the connector 400. As a result, a movement distance of liquid increases as compared with the configuration in which the reservoir 750 is provided in the specimen treatment chip 100. Thus, in a configuration in which the reservoir 750 is provided in the specimen treatment chip 100, as a movement distance of liquid decreases, responsiveness to control of feeding liquid by the specimen treatment apparatus 500 can be improved.

The reservoir 750 is bonded to the substrate 300 on a port. As a bonding method of the reservoir 750, a bonding method such as solid phase bonding, or using an adhesive, similar to the bonding method of the substrate 300 and the fluid module 200 can be used. The reservoir 750 may be formed integrally with the substrate 300.

The reservoir 750a for storing liquid to be injected into the fluid module 200 is formed on the port 110 for injecting liquid to the fluid module 200. The reservoir 750b for storing liquid to be fed out from the fluid module 200 is formed on the port 120 for feeding out liquid from the fluid module 200.

The reservoir 750 has a volume suitable for liquid to be stored. The reservoir 750 is connected at its one end in a tubular shape to a port, and has the other end that is open. In FIG. 54, the reservoir 750 can store liquid supplied from the open other end.

The reservoir 750 is provided in its upper portion with an opening larger than a diameter of the port. This facilitates access to the inside of the reservoir 750 by the pipetter. As a result, a user can extremely easily dispense liquid to be used in the fluid module 200 into the reservoir 750a by using a pipetter. Likewise, a user can extremely easily suck liquid after being treated from the reservoir 750b by using a pipette.

In the configuration example of FIG. 54, a reservoir 751 serves as the reservoir 750a that stores a reagent for treating a specimen, and a reservoir 752 serves as the reservoir 750a that stores a specimen containing an object component, for example. A reservoir 753 serves as the reservoir 750b for recovering a sample that is fed out through a plurality of fluid modules 200 (the first fluid module 250 and the second fluid module 260).

The specimen treatment chip 100 is provided on its port with an injection pipe 760a for injecting liquid into the specimen treatment chip 100, or a feeding-out pipe 760b for feeding out liquid from the specimen treatment chip 100. The injection pipe 760a is joined to the substrate 300 on the port 110 for injecting liquid, and the feeding-out pipe 760b is joined to the substrate 300 on the port 120 for feeding out liquid. In the configuration example of FIG. 54, liquid such as various kinds of reagent and cleaning liquid to be used for specimen treatment is supplied through the injection pipe 760a. The liquid after passing through the flow channel 201 of the plurality of fluid modules 200 is discharged through the feeding-out pipe 760b.

<Configuration Example of Flow Channel of Specimen Treatment Chip>

Figure 55:
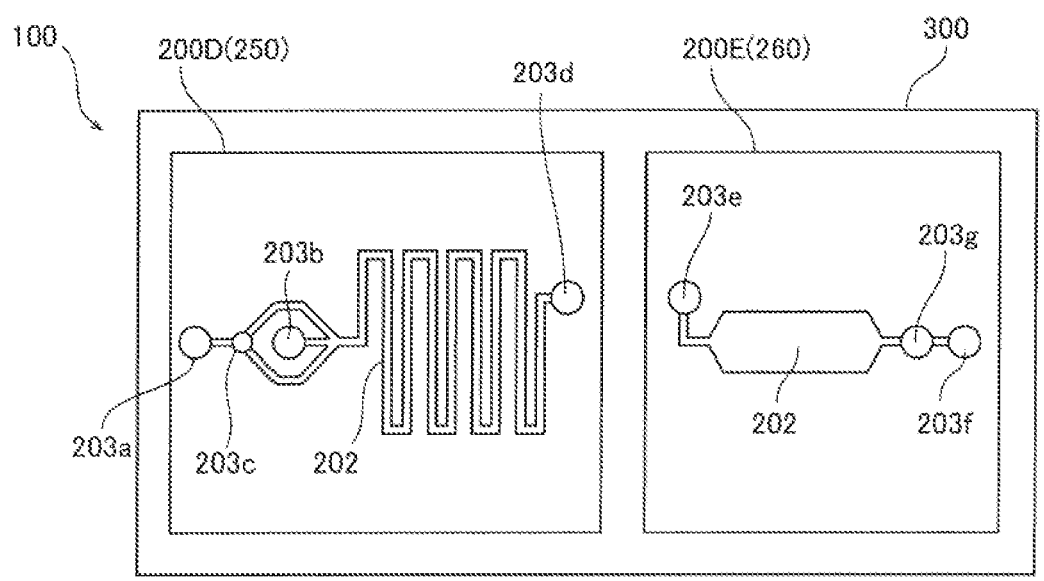
FIG. 55 illustrates a configuration example of a fluid module of the specimen treatment chip illustrated in FIG. 54.

FIG. 55 illustrates a configuration example of a fluid module 200 provided in a specimen treatment chip 100 provided with a reservoir 750. The specimen treatment chip 100 of FIG. 55 includes a fluid module 200D used for emulsion break, and a fluid module 200E used for primary cleaning, hybridization, and secondary cleaning, for example.

The fluid module 200D and the fluid module 200E are connected in series in this order from an inflow side of liquid containing DNA through a connection flow channel 350 of a substrate 300 illustrated in FIG. 54.

In the configuration example of FIG. 55, a connection portion 203b of the fluid module 200D is connected to a reservoir 752 (refer to FIG. 54), so that an emulsion containing DNA flows into the fluid module 200D from the connection portion 203b, for example. The connection portion 203a is connected to an injection pipe 760a (refer to FIG. 54), so that a reagent for breaking an emulsion, cleaning liquid used for primary cleaning in the fluid module 200E, and cleaning liquid used for secondary cleaning flow into the fluid module 200D from the connection portion 203a. The connection portion 203a serves as a common connection portion through which a plurality of kinds of liquid is supplied. A connection portion 203c is connected to a reservoir 751 (refer to FIG. 54), so that a reagent containing a marking substance to be used in the fluid module 200E is supplied therethrough. The cleaning liquid and the marking substance flow into the fluid module 200E through a connection portion 203d on the other end side of the fluid module 200D.

Liquid after being subjected to the emulsion breaking step, the cleaning liquid, and a reagent containing the marking substance each flow into a connection portion 203e of the fluid module 200E through the connecting flow channel 350 of the substrate 300. A connection portion 203f is connected to a reservoir 753 (refer to FIG. 54), so that liquid after being subjected to the primary cleaning, the hybridization, and the secondary cleaning, is fed out through the connection portion 203f. A connection portion 203g is connected to a feeding-out pipe 760b (refer to FIG. 54), so that the cleaning liquid to be used in the first cleaning and the second cleaning is discharged through the connection portion 203g.

(Specimen Treatment Apparatus)

Figure 56:
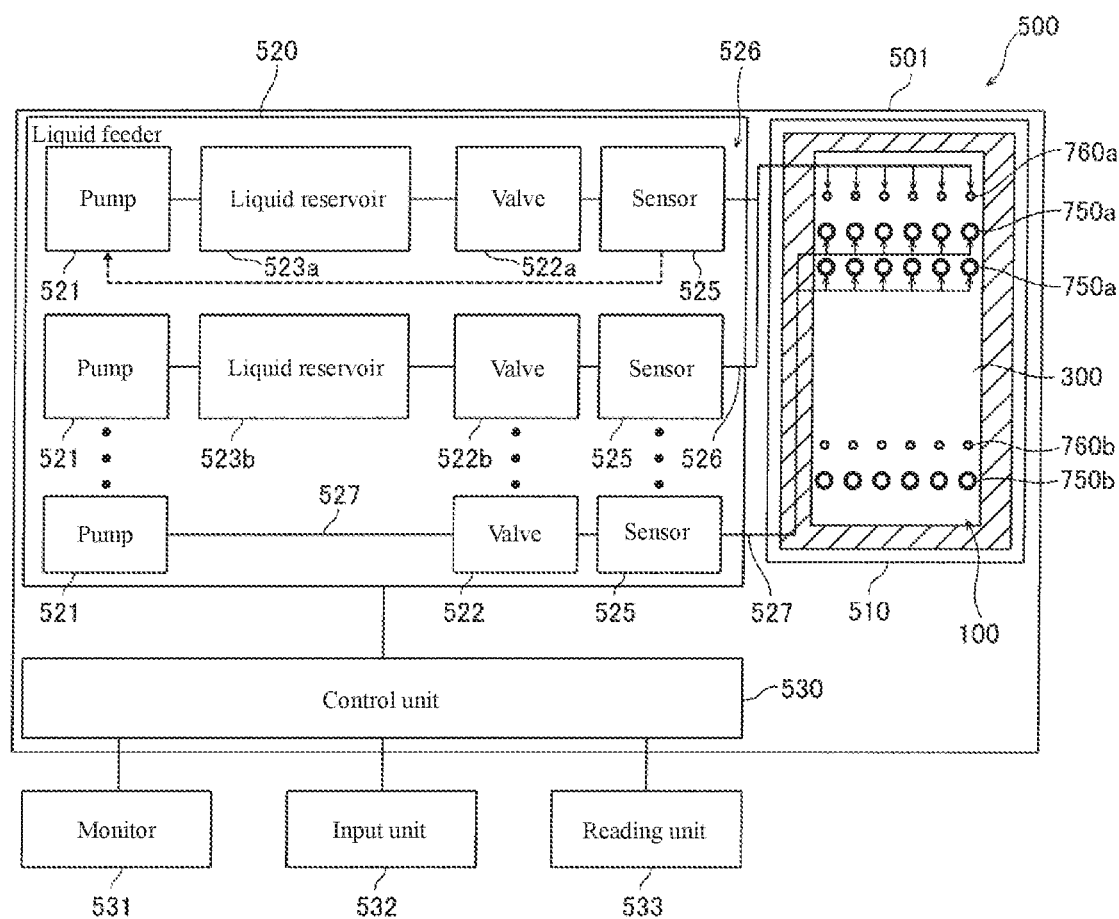
FIG. 56 is a block diagram illustrating a configuration example of a specimen treatment apparatus using the specimen treatment chip illustrated in FIG. 54.

FIG. 56 illustrates a configuration example of a specimen treatment apparatus 500 using the specimen treatment chip 100 illustrated in FIG. 54.

Each of liquid reservoirs 523a, 523b, . . . of the specimen treatment apparatus 500 stores a reagent and cleaning liquid to be supplied to the corresponding one of a plurality of fluid modules 200. In the present configuration example, instead of providing the specimen holding unit 524 (refer to FIG. 19) that holds a specimen in the specimen treatment apparatus 500, a reservoir 750 serving as a specimen holding unit is provided on a port 110 of the specimen treatment chip 100.

In addition to the specimen holding unit 524, the reservoir 750 may be disposed on the port 110 of the specimen treatment chip 100 in place of a liquid reservoir 523 for another reagent. This enables a specimen and a reagent to be directly injected into the fluid module 200 from above the port 110.

A liquid feeder 520 is provided on a surface of the specimen treatment chip 100, and is configured to be connectable to the reservoir 750 connected to a flow channel 201 of the fluid module 200. A control unit 530 controls the liquid feeder 520 so as to supply pressure to the reservoir 750 to feed liquid contained in the reservoir 750 to the fluid module 200. As a result, a specimen can be fed to the fluid module 200 from the reservoir 750 without using a path for feeding liquid such as a liquid feeding pipe 526 of the specimen treatment apparatus 500. When a specimen is fed to the fluid module 200 by using the liquid feeding pipe 526 of the specimen treatment apparatus 500, the specimen remaining in the liquid feeding pipe 526 may mix with another specimen to be subjected to next treatment. Thus, when a specimen is fed to the fluid module 200 by using the liquid feeding pipe 526 of the specimen treatment apparatus 500, it is desirable to perform a process of cleaning the inside of the liquid feeding pipe 526 or to replace the liquid feeding pipe 526, every time specimen treatment is performed. In a configuration in which the specimen treatment chip 100 includes the reservoir 750, a specimen does not need to be fed from a specimen treatment apparatus 500 side. As a result, contamination at the time of feeding a specimen to the specimen treatment chip 100 can be prevented without cleaning the liquid feeding pipe 526 or replacing the liquid feeding pipe 526.

In a configuration in which the liquid feeder 520 feeds liquid contained in the reservoir 750 of the specimen treatment chip 100 to the fluid module 200, a movement distance of liquid between a structure storing liquid to be supplied to the fluid module 200 and the fluid module 200 can be reduced as much as possible. For example, in a configuration in which a specimen is fed from the specimen holding unit 524 (refer to FIG. 19) of the specimen treatment apparatus 500 through the liquid feeding pipe 526, the specimen holding unit 524 and the fluid module 200 are connected to each other through the liquid feeding pipe 526 and the connector 400. As a result, a movement distance of liquid increases as compared with the configuration in which the reservoir 750 is provided in the specimen treatment chip 100. Thus, as a movement distance of liquid decreases, responsiveness to control of feeding liquid by the specimen treatment apparatus 500 can be improved.

In FIG. 56, the specimen treatment apparatus 500 includes an air passage 527 between a pump 521 and a valve 522, as well as between the valve 522 and the reservoir 750. The pump 521 can cause liquid to flow into the fluid module 200 from the reservoir 750 by applying pressure to the reservoir 750 through the air passage 527.

<Connection Structure to Specimen Treatment Chip>

Figure 57:
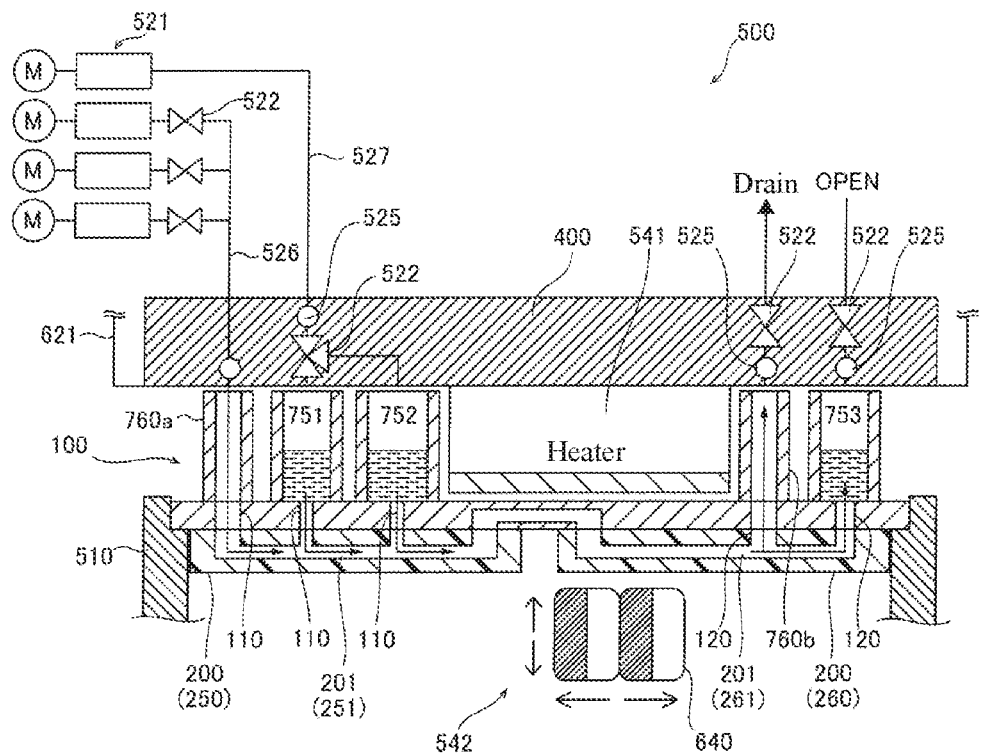
FIG. 57 is a longitudinal sectional view illustrating a connector to be connected to a specimen treatment chip.

FIG. 57 illustrates a specimen treatment chip 100 installed in an installation unit 510, and a connector 400 provided in a lid 621 corresponding to the installation unit 510. The connector 400 may be configured as a manifold in which a plurality of liquid feeding pipes 526 and air passages 527 are formed. It is possible to form the connector 400 capable of individually connecting all reservoirs 750, an injection pipe 760a, and a feeding-out pipe 760b, of the specimen treatment chip 100, to the corresponding air passages 527 and liquid feeding pipes 526. When the lid 621 is closed, the liquid feeding pipes 526 and the air passages 527 are collectively connected to the corresponding portions of the specimen treatment chip 100 with the connector 400.

The connector 400 may include a valve 522 or a flow rate sensor 525. The connector 400 of FIG. 57 is provided in its inside with valves 522 and flow rate sensors 525. This enables a path between each of the valves 522 and the flow channel 201 of the specimen treatment chip 100 to be shortened, so that it is possible to improve responsiveness of control of feeding liquid by opening and closing of each of the valves 522.

The connector 400 includes one of the valves 522, connected to a reservoir 751 that stores a reagent, one of the valves 522, connected to a reservoir 752 that stores a specimen containing an object component, and the flow rate sensors 525 each of which is disposed in a path to the corresponding one of the valves 522. In FIG. 57, each of the valves 522 is a three-way valve, so that pressure from the pump 521 can be selectively supplied to the reservoir 751 or the reservoir 752.

The connector 400 includes one of the flow rate sensors 525, for the liquid feeding pipes 526 connected to the injection pipe 760a. The connector 400 is connected to the plurality of liquid feeding pipes 526. The connector 400 is connected to the injection pipe 760a while integrating the plurality of liquid feeding pipes 526 into one system. The specimen treatment apparatus 500 can selectively supply each liquid to the injection pipe 760a by opening and closing the corresponding one of the valves 522 of the respective liquid feeding pipes 526.

In addition, the connector 400 includes one of the valves 522 as well as one of the flow rate sensors 525, connected to a reservoir 753 for recovering a sample collection, and one of the valves 522 as well as one of the flow rate sensors 525, connected to the feeding-out pipe 760b. The specimen treatment apparatus 500 can selectively discharge liquid in the flow channel 201 into the reservoir 753 or the discharge pipe 760b by selecting the valve 522 to be opened and closed.

<Treatment Unit>

In FIG. 57, treatment units are provided on both the installation unit 510 and the lid 621 corresponding to the installation unit 510.

The lid 621 includes a treatment unit different from a treatment unit installed in the installation unit 510, provided corresponding to a placement position of the corresponding fluid module 200 in the specimen treatment chip 100. This enables a treatment unit to be installed in each of the lid 621 and the installation unit 510 so as to correspond to any one of the plurality of fluid modules 200. For example, when a plurality of treatment units is disposed side by side only in the installation unit 510, a space for disposing the plurality of treatment units is required to increase an installation area of the specimen treatment apparatus 500. When a treatment unit is installed in each of the lid 621 and the installation unit 510, each treatment unit can be disposed at a position overlapping with the corresponding one of fluid modules 200 as viewed vertically, whereby it is possible to prevent the specimen treatment apparatus 500 from increasing in installation area. In addition, the treatment unit provided in the installation unit 510 can be disposed close to a lower surface of the specimen treatment chip 100, and the treatment unit provided in the lid 621 can be disposed close to an upper surface of the specimen treatment chip 100. This enables a plurality of treatment units to be brought close to the corresponding fluid modules 200. As a result, when each treatment unit applies treatment, such as heating or collection using magnetism, to the fluid module 200 from the outside, for example, heat or a magnetic force can be efficiently applied to the fluid module 200. Thus, the specimen treatment chip 100 can be efficiently treated.

For example, the lid 621 includes a heater 541 for heating liquid in the fluid module 200. In the installation unit 510, a magnet unit 542 for applying a magnetic force to liquid in the fluid module 200 is installed. Combination of treatment units is not limited to the illustrated example. For example, any one of the heater 541, the magnet unit 542, the cooling unit 543, the detector 544, and the camera unit 545, described above, may be installed in the installation unit 510, and any one of the others may be provided in the lid 621.

In the configuration example of FIG. 57, the heater 541 and the magnet unit 542 are each disposed at a position overlapping with at least one of the fluid modules 200 of the specimen treatment chip 100. That is, the heater 541 is disposed on an upper surface side of the specimen treatment chip 100, and the magnet unit 542 is disposed on a lower surface side of the specimen treatment chip 100.

For example, in the specimen treatment chip 100 including the fluid module 200D and the fluid module 200E illustrated in FIG. 55, each of the heater 541 and the magnet unit 542 is disposed at a position overlapping with the fluid module 200E. As a result, primary cleaning, hybridization, and secondary cleaning can be performed while magnetic particles in the fluid module 200E are magnetically collected by the magnet unit 542. Then, the fluid module 200E is heated to a predetermined temperature by the heater 541 in the hybridization, so that DNA on each of the magnetic particles and a marking substance bind to each other.

The marking substance is acquired by causing a fluorescent substance to bind to a probe composed of DNA complementary to DNA being an object component, for example. The DNA to be detected is denaturalized into a single strand while being heated to a predetermined temperature. The predetermined temperature when the hybridization is performed is typically about 70° C. Single-stranded DNA and the probe bind to each other by lowering temperature to about 40° C. to 50° C., from about 70° C. For example, the heater 541 heats liquid in the fluid module 200E to about 70° C., and then stops heating to lower temperature of the liquid. In the course of lowering the temperature of the liquid to room temperature, for example, the DNA and the marking substance bind to each other.

In FIG. 57, the heater 541 is installed on the lid 621 directly or through the connector 400. The heater 541 is provided on its lower surface side with a heat generating portion to adjust temperature of the fluid module 200 from an upper surface side of the specimen treatment chip 100. The magnet unit 542 includes a movable magnet 640 on a lower surface side of the specimen treatment chip 100 installed in the installation unit 510, for example.

Figure 58:
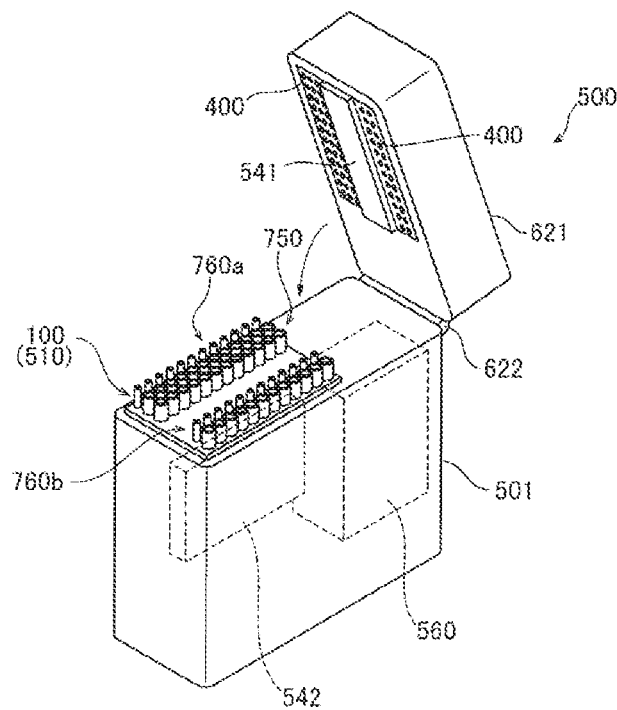
FIG. 58 is a perspective view illustrating a configuration example of a specimen treatment apparatus.

FIG. 58 is a schematic diagram illustrating appearance of the specimen treatment apparatus 500. The specimen treatment apparatus 500 includes a specimen treatment apparatus main body 501 and a lid 621 connected to the specimen treatment apparatus main body 501 with a hinge 622.

In the configuration example of FIG. 58, the installation unit 510 is disposed on an upper surface of the specimen treatment apparatus main body 501 in the shape of a box. The installation unit 510 is provided in its lower portion with a magnet unit 542. The specimen treatment apparatus main body 501 is provided in its inside with a pump unit 560 including a plurality of pumps 521. While a detailed illustration is eliminated in FIG. 58, a specimen treatment chip 100 provided with a 12-channel flow channel 201 including a first fluid module 250 and a second fluid module 260 is set in the installation unit 510.

The lid 621 is provided on its lower surface with a connector 400 and a heater 541. When the lid 621 is closed, a reservoir 750, an injection pipe 760a, and a feeding-out pipe 760b provided in the respective channels of the 12-channel flow channel 201 are collectively connected to the connector 400.

(Modification of Reservoir Installation Position)

Figure 59:
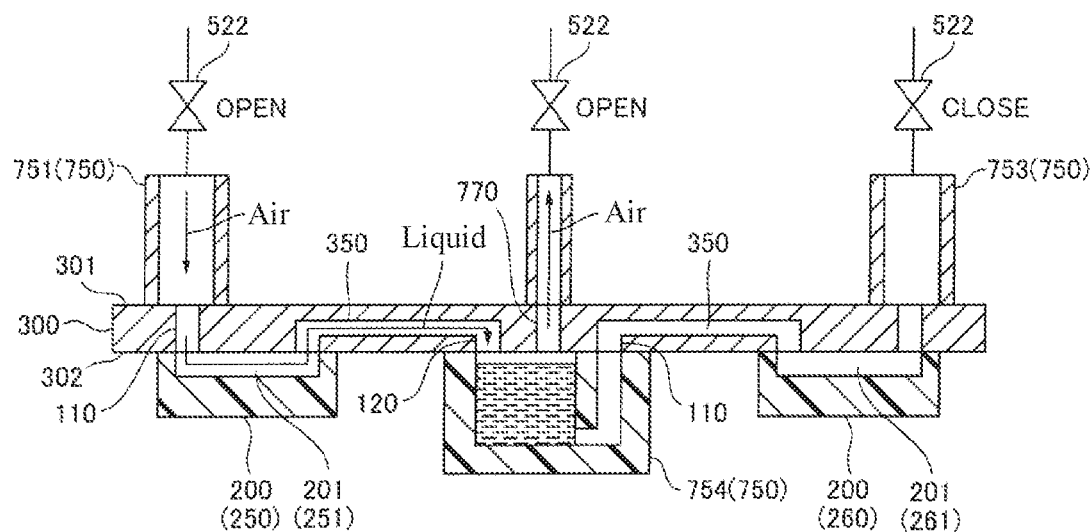
FIG. 59 illustrates a configuration example of a specimen treatment chip having a reservoir provided on a lower surface of a substrate.

In the configuration example of FIG. 54, while the reservoir 750 is provided on the first surface 301 of the substrate 300, the reservoir 750 may be provided on the second surface 302 being the lower surface of the substrate 300. FIG. 59 illustrates a configuration example in which the reservoir 750 is provided on the second surface 302 of the substrate 300.

In FIG. 59, the reservoir 750 includes a reservoir 754 provided on the second surface 302 of the substrate 300. The reservoir 754 is connected to a port 120 for feeding out liquid from a fluid module 200, a port 110 for injecting liquid into the fluid module 200, and a port 770 serving as an air passage.

As illustrated in FIG. 59, the reservoir 750 can be installed not only at an inlet port or an outlet port of the specimen treatment chip 100, but also at an intermediate position of the specimen treatment chip 100. That is, the reservoir 750 may be disposed between the plurality of fluid modules 200. In this case, after liquid flowing out from the fluid module 200 on an upstream side is temporarily stored, the liquid can be supplied to the fluid module 200 on a downstream side. In the present example, the reservoir 754 is installed between the first fluid module 250 and the second fluid module 260.

This enables liquid in the first fluid module 250 to be different from liquid in the second fluid module 260 in flow rate. For example, when the first flow channel 251 of the first fluid module 250 is continuously connected to the second flow channel 261 of the second fluid module 260, liquid at the tail end is discharged from the first flow channel 251 of the first fluid module 250, and then liquid at the leading end may flow through the second flow channel 261 of the second fluid module 260. In that case, a flow rate in the second fluid module 260 cannot be freely controlled until all liquid is discharged from the first flow channel 251 of the first fluid module 250. When liquid is temporarily recovered into the reservoir 754 between the first fluid module 250 and the second fluid module 260, a flow rate of liquid in the second fluid module 260 can be freely set.

In each of the fluid modules 200, a flow rate of liquid varies depending on contents of treatment performed by the fluid module 200, shape and size of a flow channel 201, and the like. When the reservoir 750 is disposed between the plurality of fluid modules 200, it is preferable that the reservoir 750 is disposed between two fluid modules 200 that are largely different in a flow rate range of liquid. For example, in the emulsion PCR assay illustrated in FIG. 39, droplets are formed by a mixed liquid of DNA and a reagent, and a dispersion medium, in the emulsion forming step. Thus, in the fluid module 200B used for forming an emulsion, a flow rate of liquid in the flow channel is increased by adding a flow rate of each of the mixed liquid and the dispersion medium.

Meanwhile, in the emulsion breaking step, it is preferable to make a flow rate of an emulsion in which droplets are dispersed lower than a flow rate of a reagent for breaking an emulsion to efficiently break down the droplets. That is, in the fluid module 200D used for breaking an emulsion, it is preferable to make a flow rate of an emulsion relatively low. An emulsion increased in a flow rate in the fluid module 200B passes through the fluid module 200C used for emulsion PCR to flow into the fluid module 200D. As a result, when the fluid modules 200B, 200C, and 200D are connected in series, it may be difficult to lower a flow rate of the emulsion in the fluid module 200D. Thus, it is preferable to provide a reservoir 750 between the fluid module 200B and the fluid module 200C, or between the fluid module 200C and the fluid module 200D. This enables a flow rate in the fluid module 200B and a flow rate in the fluid module 200D to be independently controlled, so that treatment can be performed at a flow rate suitable for each treatment.

In FIG. 59, when pressure is supplied to a reservoir 751 on an inlet side to open a valve 522 connected to a port 770 serving as an air passage, liquid in the reservoir 751 is supplied to a first fluid module 250. When pressure to be supplied to the reservoir 751 is controlled, a flow rate of liquid in the first fluid module 250 is controlled. When a valve 522 connected to a reservoir 753 on an outlet side is closed, liquid having passed through the first fluid module 250 is recovered in a reservoir 754 and is not fed to a second fluid module 260 side.

Figure 60:
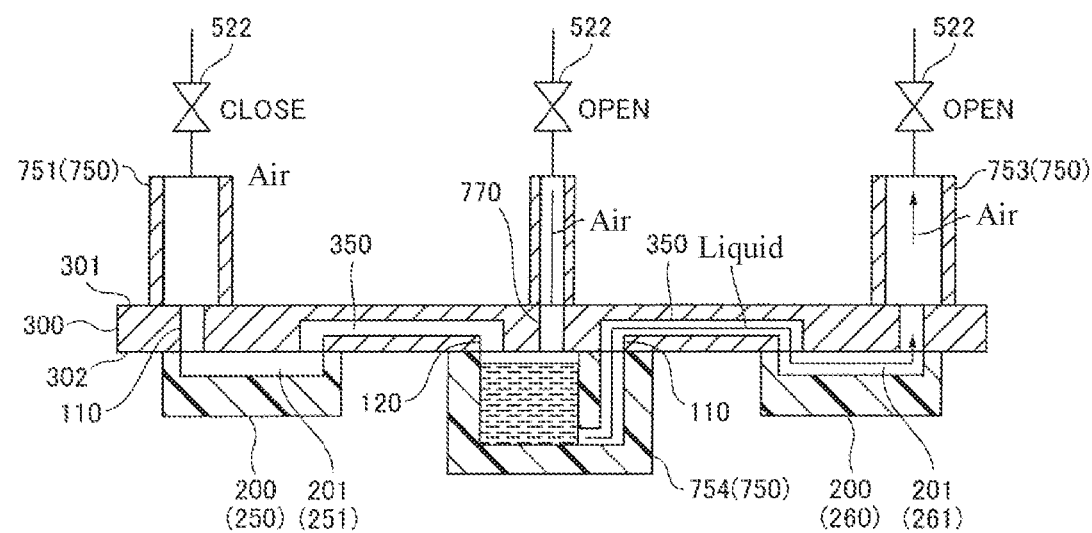
FIG. 60 illustrates a flow of liquid in the specimen treatment chip in FIG. 59.

As illustrated in FIG. 60, when the valve 522 connected to the reservoir 751 on the inlet side is closed and the valve 522 connected to the reservoir 753 on the outlet side is opened to supply pressure to the reservoir 754 from the port 770 serving as an air passage, liquid in the reservoir 754 is supplied to a second fluid module 260. When pressure to be supplied to the reservoir 754 is controlled, a flow rate of liquid in the second fluid module 260 is controlled. The liquid having passed through the second fluid module 260 is recovered in the reservoir 753.

Figure 61:
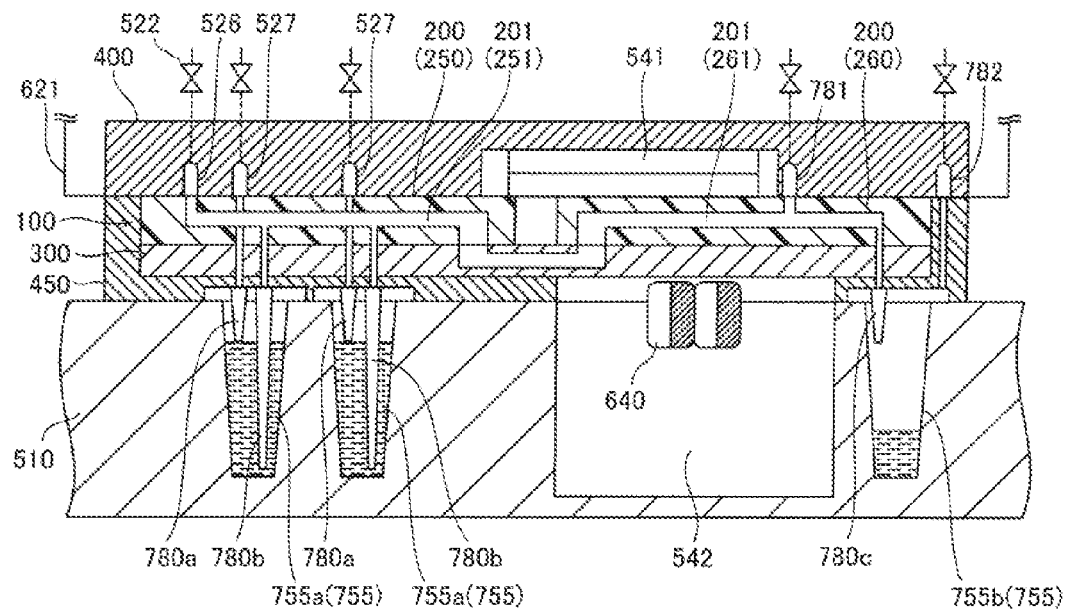
FIG. 61 illustrates an example in which a reservoir is provided in an installation unit on a lower side of a specimen treatment chip.
Figure 62:
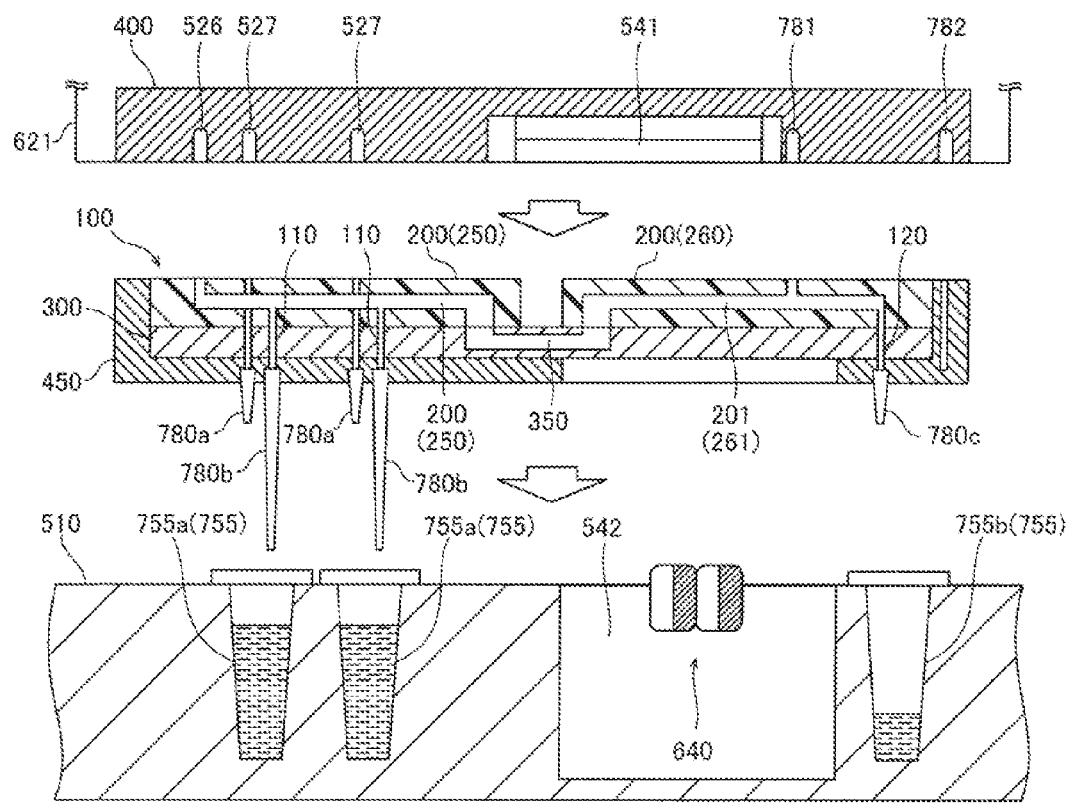
FIG. 62 is an exploded view of the lid, the specimen treatment chip, and the installation unit, of FIG. 61, which are separated from each other.

While FIGS. 54 and 59 each illustrate an example in which the reservoir 750 is provided on the surface of the specimen treatment chip 100, FIGS. 61 and 62 each illustrate an example in which a reservoir 755 is provided in an installation unit 510 on a lower surface side of a specimen treatment chip 100. FIG. 61 illustrates a state where the specimen treatment chip 100 is installed on the installation unit 510 and a lid 621 is closed, and FIG. 62 illustrates the installation unit 510, the specimen treatment chip 100, and the lid 621 separately.

The reservoir 755 opens upward, and an opening thereof is closed when being brought into contact with a lower surface of the specimen treatment chip 100 or a lower surface of a fixture 450. In a reservoir 755*a* for storing liquid to be injected into a fluid module 200, there are disposed a connecting pipe 780*a* connected to an air passage 527, and a connecting pipe 780*b* connected to a flow channel 201 of the fluid module 200 through a port 110. When a liquid feeder 520 supplies pressure through the air passage 527, it is possible to push out liquid in the reservoir 755*a* from the connection pipe 780*b* into the fluid module 200.

In a reservoir 755*b* for storing liquid fed out from the fluid module 200, there is disposed a connection pipe 780*c* connected to the flow channel 201 of the fluid module 200 through a port 120. Pressure from the liquid feeder 520 causes liquid having passed through the fluid module 200 to flow into the reservoir 755*b* through the connecting pipe 780*c*. Air in the reservoir 755*b* is discharged into an air passage 782 of a connector 400.

As with FIG. 57, the valve 522 is opened and closed to enable liquid supply from the liquid feeding pipe 526 to be turned on and off, and to enable the air passage 527 for supplying pressure to be selected. In addition, the valve 522 is opened and closed to enable liquid to be fed out to any one of a drainage path 781 for cleaning liquid and the like, and the reservoir 755*b*.

In the configuration example of FIGS. 61 and 62, the reservoir 755 is provided separately from the specimen treatment chip 100, and is installed in the installation unit 510, so that it is possible to handle only the reservoir 755 alone. A user injects liquid to be injected into the fluid module 200 into the reservoir 755*a*, and sets the reservoir 755*a* in the installation unit 510. Then the user sets the specimen treatment chip 100 in the installation unit 510 after setting an empty reservoir 755*b* in the installation unit 510. When the specimen treatment chip 100 is removed from the installation unit 510 after treatment by the specimen treatment apparatus 500 is finished, the reservoir 755*b* containing a treated sample can be independently removed to be set in another detector or treatment apparatus, or the like.

It is to be understood that the embodiments disclosed this time are examples in all respects, and are not restrictive. The scope of the present invention is indicated not by the description of the above embodiments but by the scope of claims, and includes meanings equivalent to the scope of claims and all changes (modifications) within the scope.

What is claimed is:

1. A specimen treatment chip configured to be provided in a specimen treatment apparatus to apply specimen treatment including a plurality of treatment steps to an object component in a specimen supplied by the specimen treatment apparatus, the specimen treatment chip comprising:
   a substrate;
   a first fluid module provided on a first surface of the substrate, the first fluid module including a first flow channel for applying a first treatment step to the object component in the specimen supplied by the specimen treatment apparatus, wherein the first flow channel is integrally formed in the first fluid module;
   a second fluid module that is provided separately from the first fluid module, the second fluid module including a second flow channel for applying a second treatment step to the object component to which the first treatment step has been applied, wherein the second fluid module is provided on the first surface of the substrate, and the second flow channel is integrally formed in the second fluid module;
   a third fluid module that is provided separately from the first fluid module and the second fluid module, the third fluid module including a third flow channel in fluid connection with at least one of the first flow channel and the second flow channel and configured to apply a third treatment step to the object component, wherein the third fluid module is provided on a second surface of the substrate opposite the first surface, and the third flow channel is integrally formed in the third fluid module, wherein the third fluid module also includes a connection flow channel configured to connect the first fluid module and the second fluid module to each other to move the object component from the first flow channel to the second flow channel, wherein the connection flow channel is integrally formed in the third fluid module;
   a first connection port configured to be connected to the specimen treatment apparatus to receive an injection of an inspection liquid to be used in the first treatment step, the first connection port provided on the second surface of the substrate and in fluid connection with the first flow channel through a first substrate flow channel integrally formed at least in part in the substrate; and
   a second connection port configured to be connected to the specimen treatment apparatus and configured to receive and injection of a reagent to be used in the second treatment step, the second connection port provided on the second surface of the substrate and in fluid connection with the second flow channel through a second substrate flow channel integrally formed at least in part in the substrate.

2. The specimen treatment chip according to claim 1, wherein the first fluid module is configured to apply the first treatment step that is different from the second treatment step applied by the second fluid module to the object component in the specimen.

3. The specimen treatment chip according to claim 1, wherein the first fluid module and the second fluid module are further configured to apply, to the object component in the specimen, the plurality of treatment steps including:

a first step of forming in a dispersion medium a droplet containing a mixed liquid of nucleic acid as the object component, a reagent for an amplification reaction of the nucleic acid, and a carrier for the nucleic acid;

a second step of amplifying the nucleic acid in the droplet formed in the first step;

a third step of breaking down the droplet containing the carrier carrying an amplification product of the nucleic acid, acquired in the second step;

a fourth step of collecting the carrier extracted from the droplet by breaking in the third step; and a fifth step of causing the amplified product on the carrier collected in the fourth step to react with a marking substance, wherein the first fluid module is configured to apply the first treatment step and the second fluid module is configured to apply the second treatment step, and the first treatment step and the second treatment step are two respective consecutive treatment steps selected from among the first step, the second step, the third step, the fourth step, and the fifth step.

4. The specimen treatment chip according to claim 1, wherein the first fluid module and the second fluid module are further configured to apply, to the object component in the specimen, the plurality of treatment steps including:

a first step of forming an immunocomplex in which the object component is caused to bind to a carrier by antigen-antibody reaction;

a second step of causing the immunocomplex formed in the first step to react with a marking substance;

a third step of forming in a dispersion medium a droplet containing the immunocomplex to which the marking substance binds in the second step and a substrate for detecting the marking substance; and a fourth step of causing the substrate to react with the marking substance in the droplet formed in the third step, wherein the first fluid module is configured to apply the first treatment step and the second fluid module is configured to apply the second treatment step, and the first treatment step and the second treatment step are two respective consecutive treatment steps selected from among the first step, the second step, the third step, and the fourth step.

5. The specimen treatment chip according to claim 1, wherein the first fluid module and the second fluid module are further configured to apply, to the object component in the specimen, the plurality of treatment steps including:

a first step of mixing a cell as the object component with a reagent for amplification reaction of a nucleic acid in the cell;

a second step of forming in a dispersion medium a droplet containing a mixed liquid of liquid mixed in the first step and a cell lysis reagent; and a third step of amplifying the nucleic acid eluted from the cell in the droplet in the second step, in the droplet by, wherein the first fluid module is configured to apply the first treatment step and the second fluid module is configured to apply the second treatment step, and the first treatment step and the second treatment step are two respective consecutive treatment steps selected from among the first step, the second step, and the third step.

6. The specimen treatment chip according to claim 1, wherein the first substrate flow channel or the second substrate flow channel is a through hole that is provided at a position corresponding to the first flow channel or the second flow channel, and that passes through the substrate in its thickness direction.

7. The specimen treatment chip according to claim 6, wherein a plurality of the through holes is formed in the substrate at a predetermined pitch.

8. The specimen treatment chip according to claim 1, wherein
at least the first flow channel or the second flow channel includes at least two connection portions.

9. The specimen treatment chip according to claim 1, wherein
the first flow channel is formed integrally in the first fluid module for feeding liquid between the first fluid module and another fluid module or the specimen treatment apparatus, and
the second flow channel is formed integrally in the second fluid module for feeding liquid between the second fluid module and another fluid module or the specimen treatment apparatus.

10. The specimen treatment chip according to claim 1, wherein at least the third fluid module includes a first layer in which the third flow channel is formed, and a second layer in which the connection flow channel is formed.

11. The specimen treatment chip according to claim 1, wherein the first connection port for injecting the inspection liquid is a through hole that passes through the substrate in its thickness direction, and that is connected from the second surface of the substrate to the first flow channel of the first fluid module disposed on the first surface of the substrate.

12. The specimen treatment chip according to claim 1, wherein
the substrate includes a third connection port for recovering liquid from the specimen treatment chip for quality monitoring of the specimen treatment chip, and
the third connection port is in fluid connection with at least one of the first flow channel of the first fluid module or the second flow channel of the second fluid module.

13. The specimen treatment chip according to claim 12, wherein the third connection port is a through hole that passes through the substrate in its thickness direction.

14. The specimen treatment chip according to claim 1, wherein the first fluid module and the second fluid module are each made of a different material.

15. The specimen treatment chip according to claim 14, wherein the first fluid module and the second fluid module are each made of a material suitable for the corresponding one of the first treatment step and the second treatment step.

16. The specimen treatment chip according to claim 1, wherein the first flow channel and the second flow channel have shapes different from each other.

17. The specimen treatment chip according to claim 16, wherein the first flow channel and the second flow channel each have a different height in the thickness direction of the substrate.

18. A specimen treatment apparatus configured to treat an object component in a specimen using a specimen treatment chip, the specimen treatment apparatus comprising:

an installation unit for installing a specimen treatment chip in which a first fluid module for applying a first treatment step to an object component in a specimen, and a second fluid module provided separately from the first fluid module for applying a second treatment step to the object component to which the first treatment step has been applied, are installed on a first surface of a substrate, and in which a third fluid module provided separately from the first fluid module and the second fluid module for applying a third treatment step to the object component is installed on a second surface of the substrate, wherein the third fluid module includes a third flow channel in fluid connection with at least one of the first flow channel and the second flow channel, and a connection flow channel configured to connect the first fluid module and the second fluid module to each other to move the object component from the first flow channel to the second flow channel, wherein the connection flow channel is integrally formed in the third fluid module;

a lid that is provided to be openable for a specimen treatment chip set in the installation unit, and that has a connector to be connected to a connection port provided on the second surface of the substrate, wherein the connection port is in fluid connection with the first fluid module through a substrate flow channel that is integrally formed at least in part in the substrate;

a liquid feeder that supplies a specimen containing an object component to a specimen treatment chip through the connector to feed the specimen; and a control unit that controls the liquid feeder so as to feed liquid in the specimen treatment chip to the first fluid module and the second fluid module in order through the connection flow channel.

19. The specimen treatment apparatus according to claim 18, wherein the third fluid module includes:

a first layer in which the third substrate flow channel is formed; and a second layer in which the connection flow channel is formed.

20. A specimen treatment method for treating an object component in a specimen using a specimen treatment chip, the specimen treatment method comprising:

performing a first treatment step of supplying a specimen containing an object component to a specimen treatment chip in which a first fluid module for applying the first treatment step to the object component in the specimen, and a second fluid module provided separately from the first fluid module for applying a second treatment step to the object component to which the first treatment step has been applied, are installed on a first surface of a substrate, through a first connection port provided on a second surface of the substrate, to feed the specimen in the specimen treatment chip to the first fluid module, wherein the first connection port is connected to the first fluid module through a substrate flow channel that is integrally formed at least in part in the substrate; and performing the second treatment step on the object component to which the first treatment step has been applied by feeding the object component in the first fluid module to the second fluid module through a connection flow channel, wherein the connection flow channel is integrally formed in a third fluid module installed on the second surface of the substrate and provided separately from the first fluid module and the second fluid module; and performing a third treatment step on the object component by feeding the object component to the third fluid module.

21. The specimen treatment method according to claim 20, further comprising:

performing the third treatment step on the object component by passing the object component through a flow channel formed in a first layer of the third fluid module; and feeding the object component in the first fluid module to the second fluid module through the connection flow channel formed in a second layer of the third fluid module.

* * * * *